United States Patent
Hopper

(10) Patent No.: US 9,913,751 B2
(45) Date of Patent: Mar. 13, 2018

(54) LENS AID AND LENS AID SYSTEM AND TECHNIQUES FOR THE INSERTION AND REMOVAL OF CONTACT AND SCLERAL LENSES

(71) Applicant: Thomas P. Hopper, Concord, NH (US)

(72) Inventor: Thomas P. Hopper, Concord, NH (US)

(\*) Notice: Subject to any disclaimer, the term of this patent is extended or adjusted under 35 U.S.C. 154(b) by 0 days.

(21) Appl. No.: 15/392,921

(22) Filed: Dec. 28, 2016

(65) Prior Publication Data

US 2017/0281410 A1   Oct. 5, 2017

Related U.S. Application Data

(60) Provisional application No. 62/318,458, filed on Apr. 5, 2016.

(51) Int. Cl.
 *A61F 9/00* (2006.01)
(52) U.S. Cl.
 CPC .................. *A61F 9/0061* (2013.01)
(58) Field of Classification Search
 CPC .................................... A61F 9/0061
 USPC ........................................ 294/1.2
 See application file for complete search history.

(56) References Cited

U.S. PATENT DOCUMENTS

| | | | | |
|---|---|---|---|---|
| 3,129,971 A | * | 4/1964 | Kobler | A61F 9/0061 206/5 |
| 3,304,113 A | * | 2/1967 | Hutchison | A61F 9/0061 294/1.2 |
| 3,743,337 A | * | 7/1973 | Crary | A61F 9/0061 294/1.2 |
| 3,910,618 A | * | 10/1975 | Massenz | A61F 9/0061 294/1.2 |
| 4,113,297 A | * | 9/1978 | Quinn | A61F 9/0061 294/1.2 |
| 4,123,098 A | | 10/1978 | Shoup | |
| 4,387,921 A | * | 6/1983 | Licata | A61F 9/0061 294/1.2 |
| 4,600,003 A | | 7/1986 | Lopez | |
| 5,695,049 A | * | 12/1997 | Bauman | A45C 11/005 206/5.1 |
| 5,788,706 A | * | 8/1998 | Deminski | A61F 9/0061 606/107 |
| 5,879,038 A | * | 3/1999 | Morgan | A61F 9/0061 294/1.2 |
| 6,398,277 B1 | | 6/2002 | McDonald | |

(Continued)

FOREIGN PATENT DOCUMENTS

| | | | |
|---|---|---|---|
| FR | 2716108 | * | 8/1995 |
| WO | WO 01/10367 | * | 2/2001 |
| WO | 2008-149795 | | 11/2008 |

OTHER PUBLICATIONS

Insertion and Removal Devices ("Plungers"); https://www.dryeyeshop.com/mobile/insertion-removal-devices-plungers-c140.aspx; Mar. 7, 2016.

(Continued)

*Primary Examiner* — Dean J Kramer
(74) *Attorney, Agent, or Firm* — Z IP Law PLLC; Claire Zopf

(57) ABSTRACT

A lens aid, lens aid system and powered light source combined with a mirror that uses a lens cup of soft pliable material providing an improved visual method including a hands-free or one hand method for the insertion of a contact lens and more preferably a scleral lens into the eye.

18 Claims, 38 Drawing Sheets

(56) References Cited

U.S. PATENT DOCUMENTS

| | | | | |
|---|---|---|---|---|
| 6,401,915 B1* | 6/2002 | Faxe | .................... | A45C 11/005 |
| | | | | 206/210 |
| 6,572,165 B2* | 6/2003 | Faxe | .................... | A61F 9/0061 |
| | | | | 206/5.1 |
| 7,163,245 B2* | 1/2007 | Wallock | ................ | A61F 9/0061 |
| | | | | 294/1.2 |
| 2007/0164576 A1* | 7/2007 | Kim | .................... | A61F 9/0061 |
| | | | | 294/1.2 |

OTHER PUBLICATIONS

How to Insert Your Device with a Plunger; Boston Foundation for Sight; Feb. 2012—v. 20, p. 7.

PROSE Accessory Buying Guide; Boston Foundation for Sight; Feb. 2012—v. 20, p. 15.

* cited by examiner

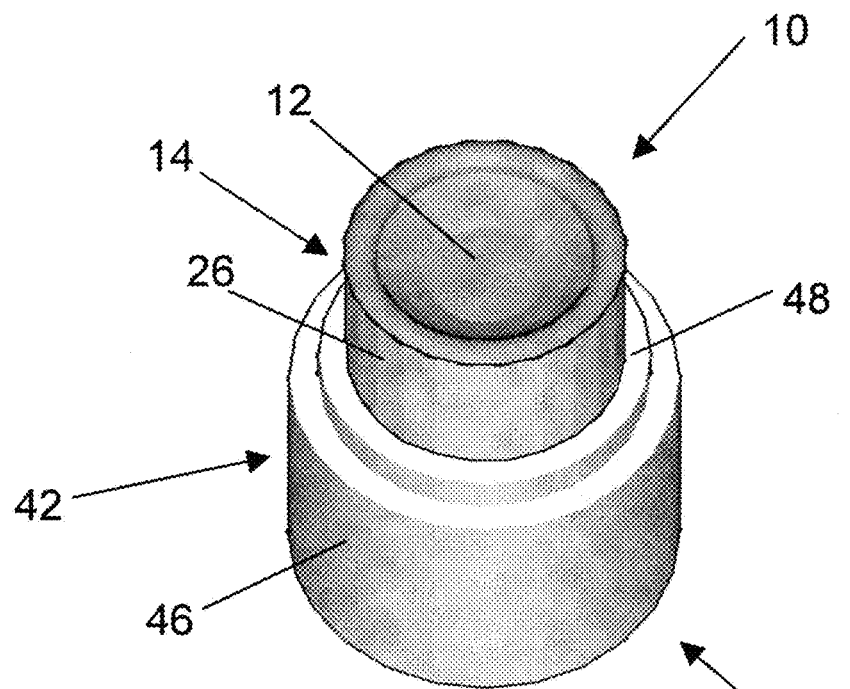
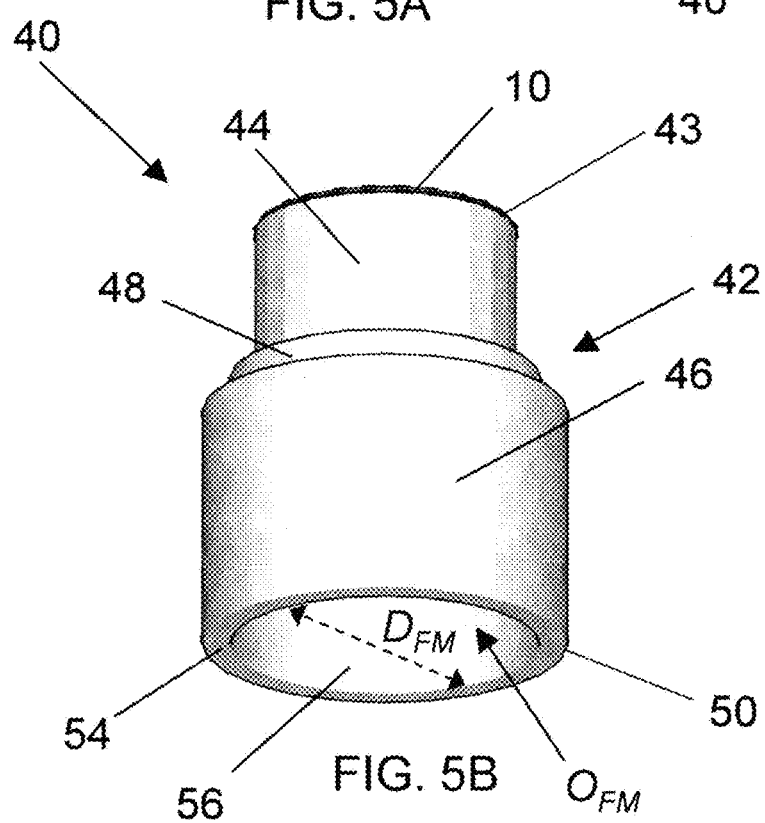

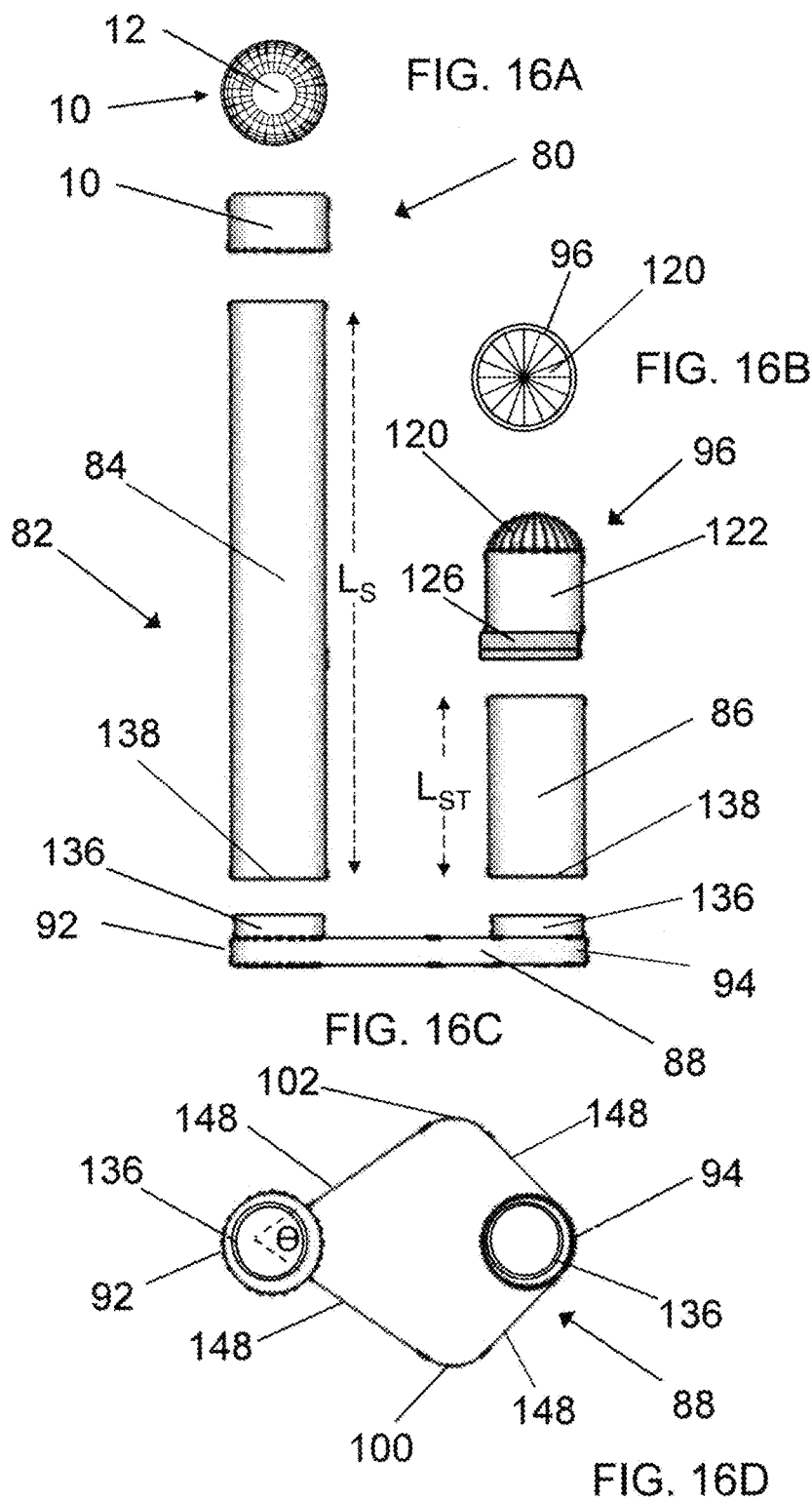

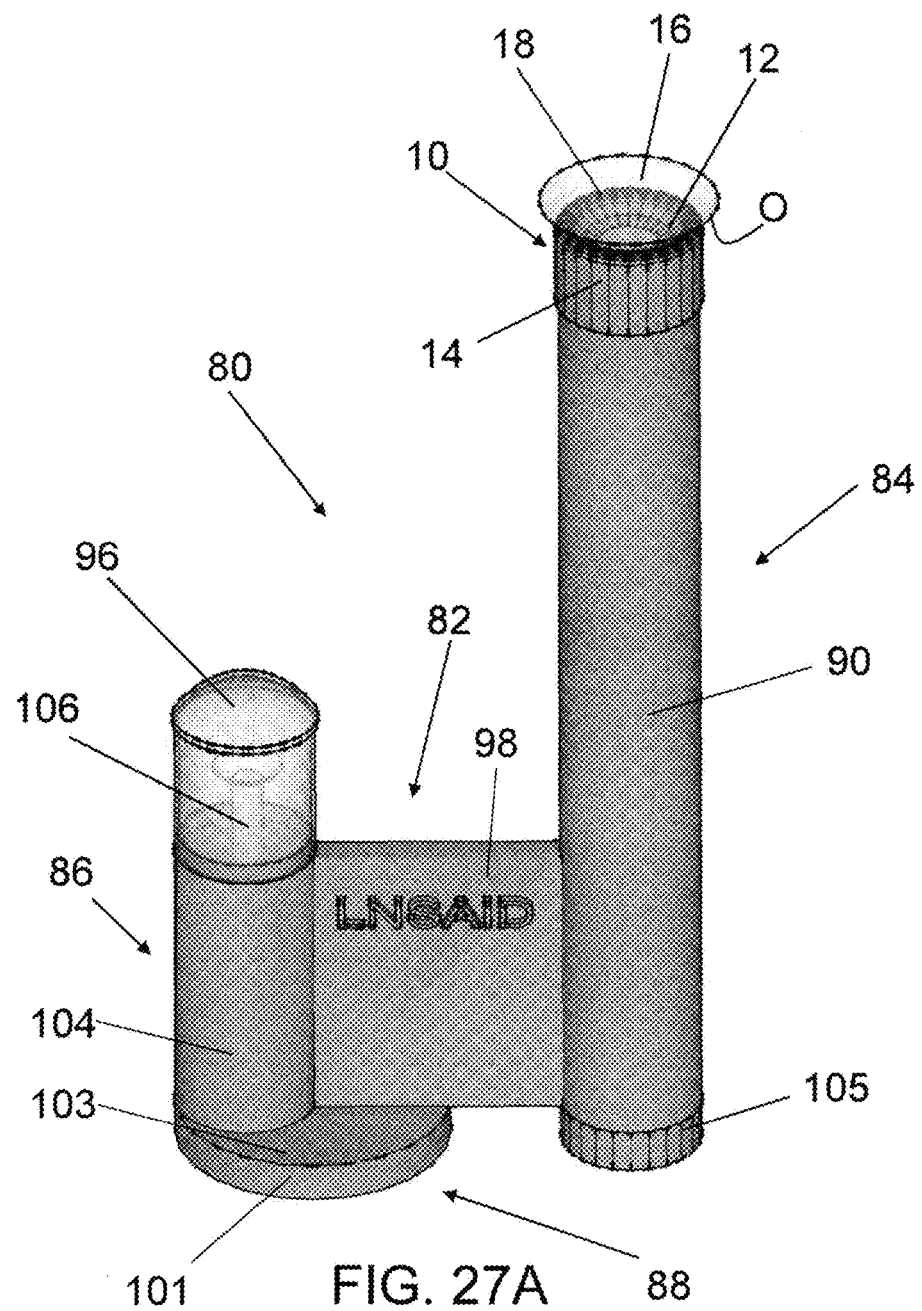

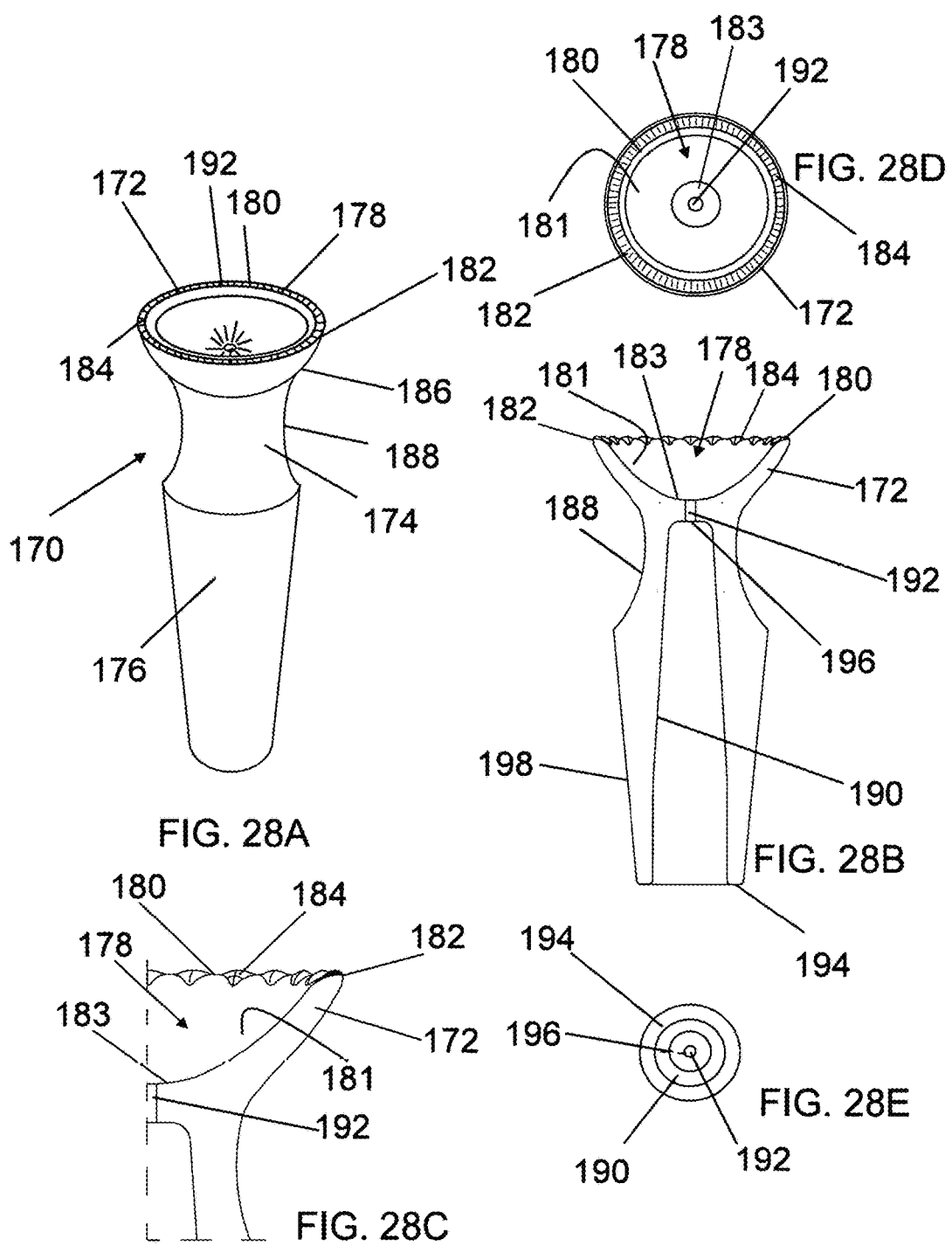

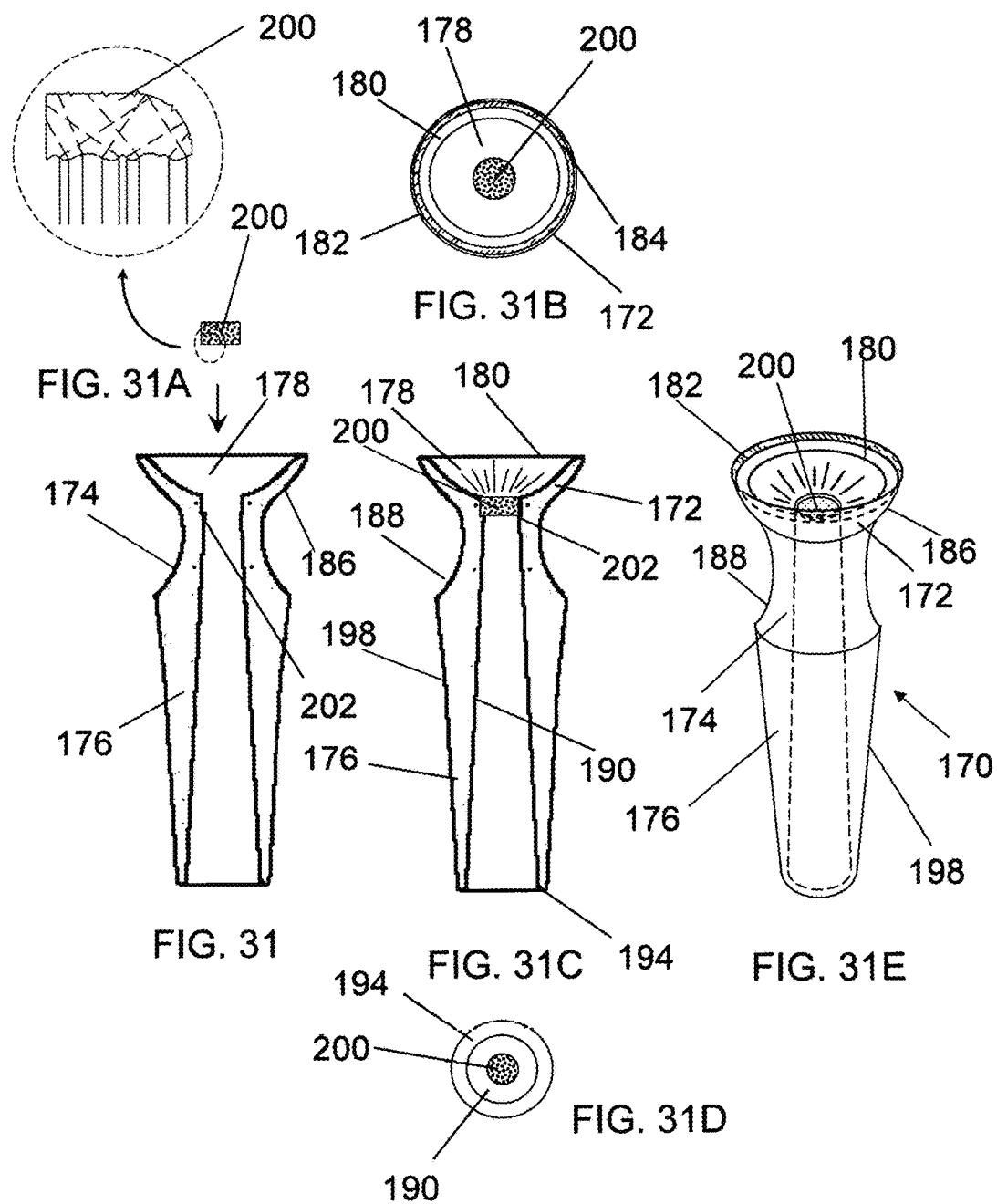

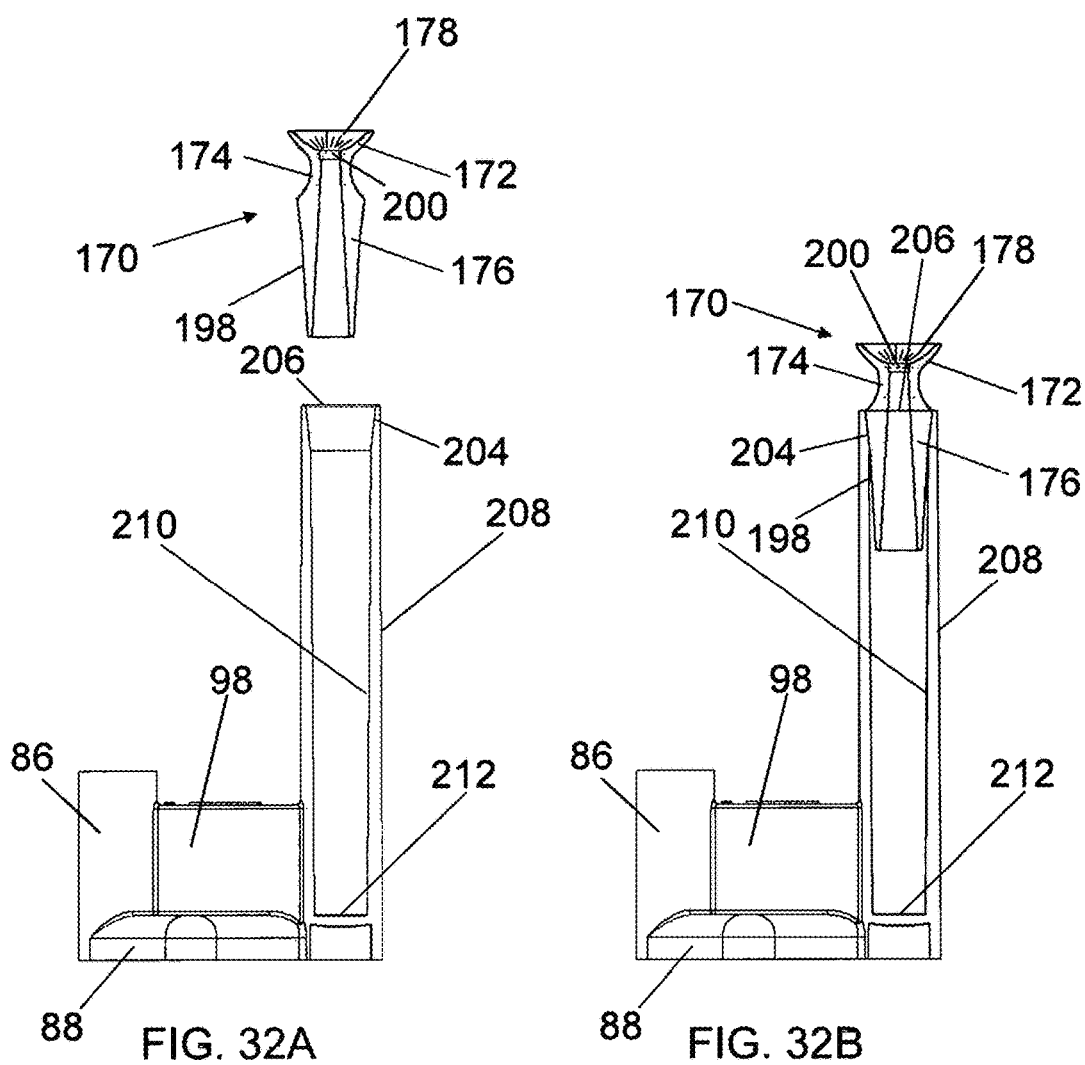

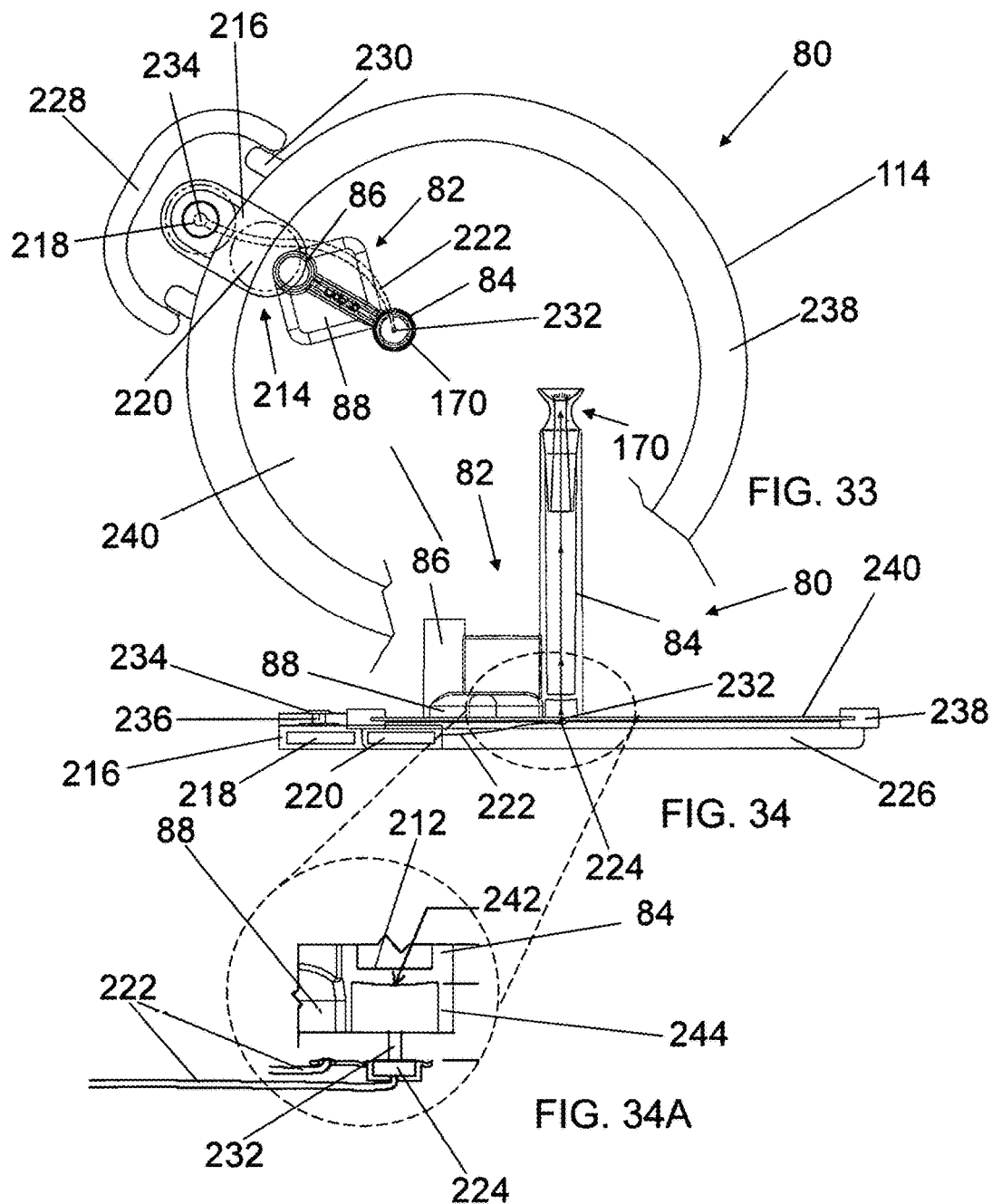

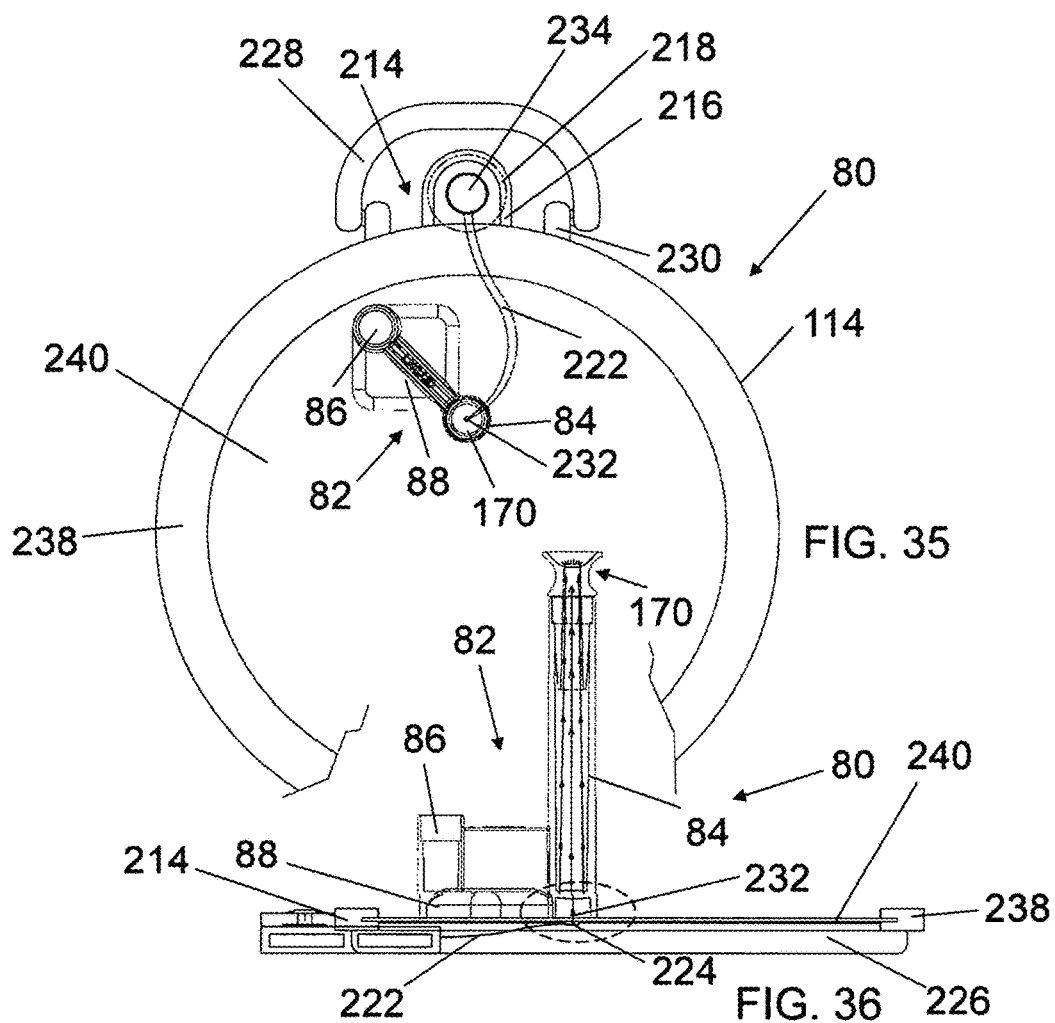
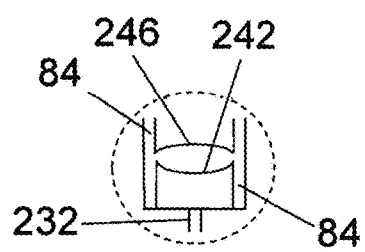 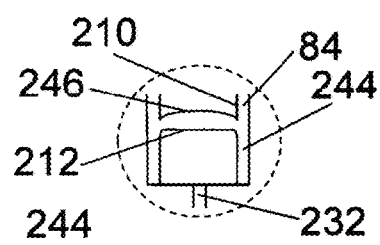

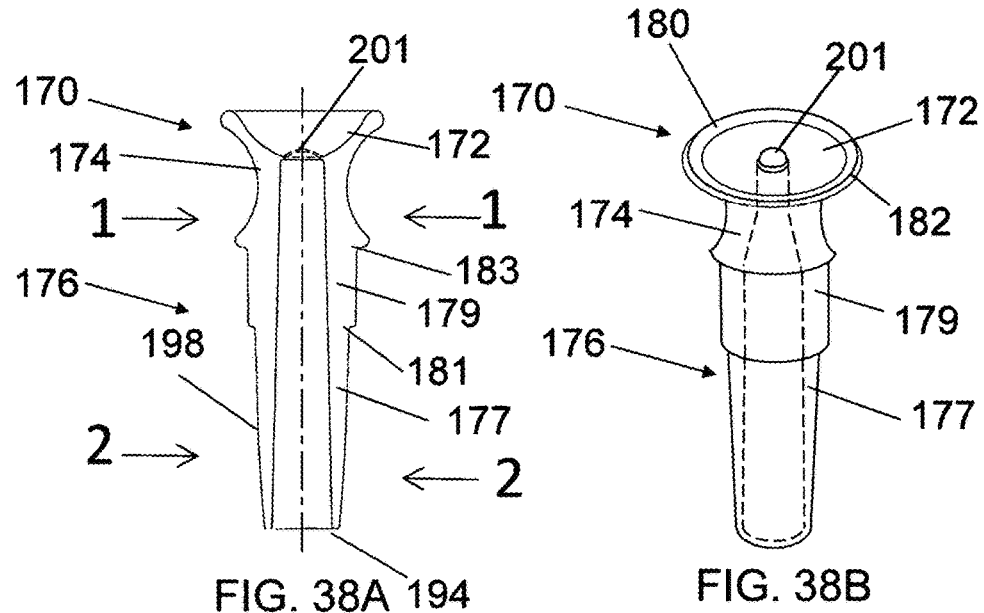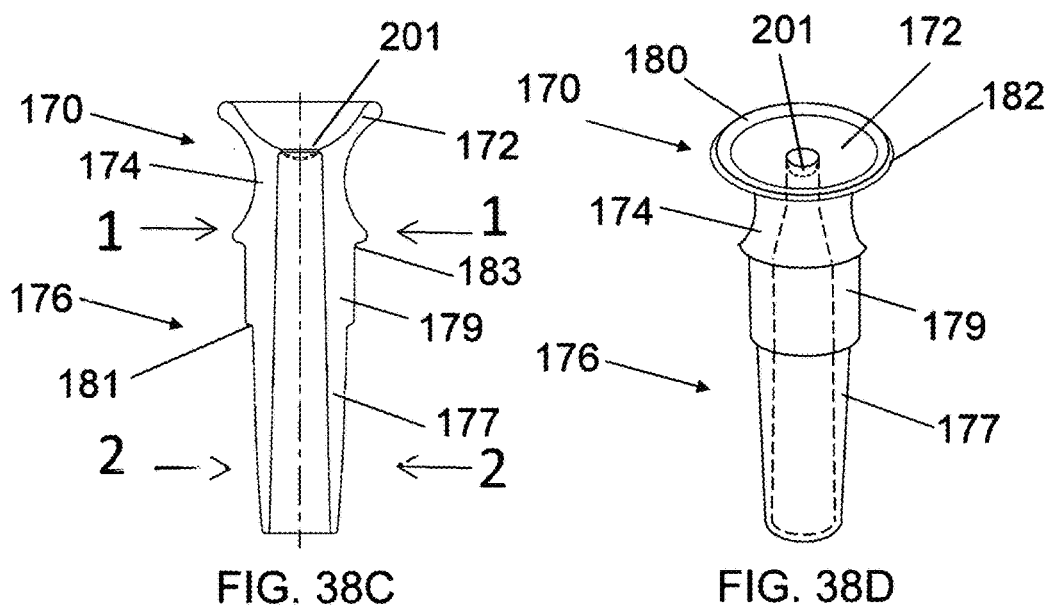

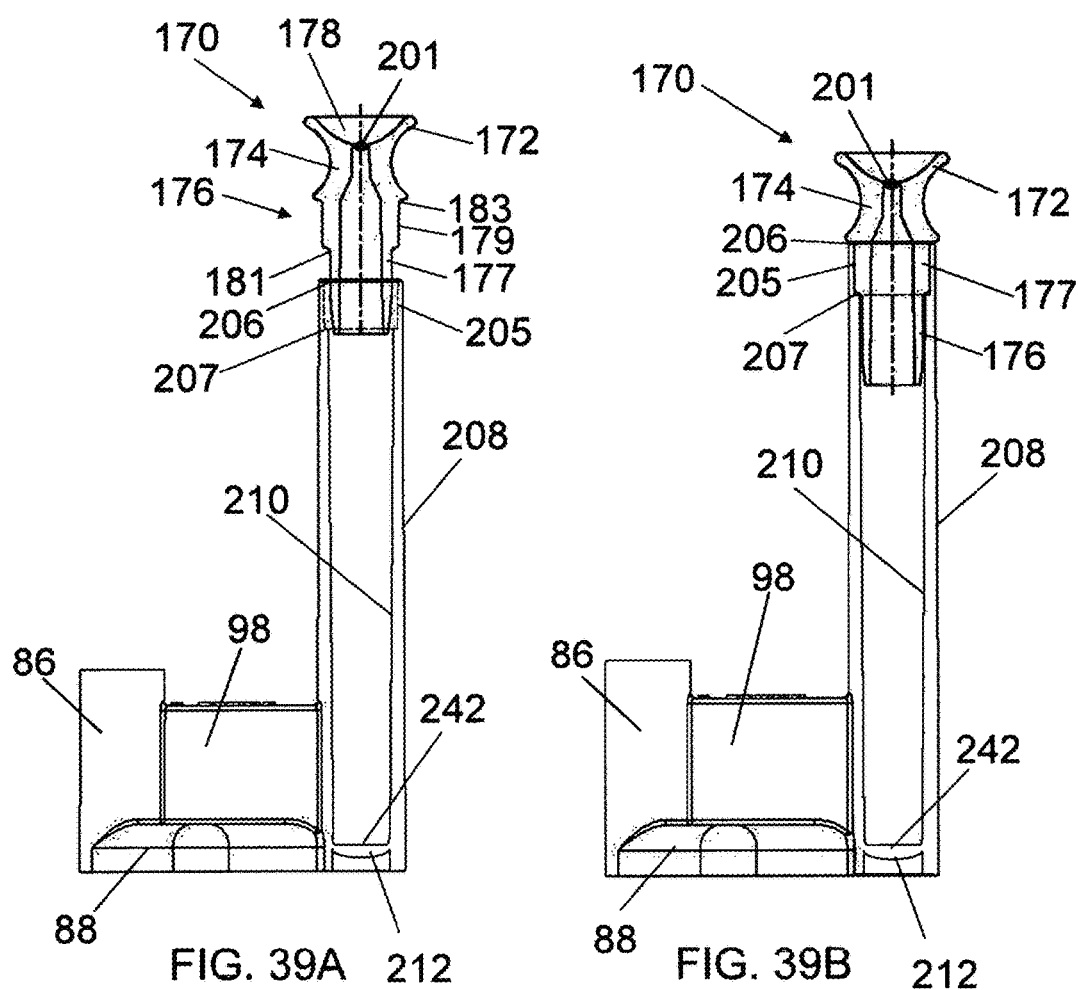

LENS AID AND LENS AID SYSTEM AND TECHNIQUES FOR THE INSERTION AND REMOVAL OF CONTACT AND SCLERAL LENSES

RELATED PATENT APPLICATION

This application claims the benefit of U.S. Provisional Patent Application No. 62/318,458 filed Apr. 5, 2016 entitled LENS AID AND LENS AID SYSTEM AND TECHNIQUES FOR THE INSERTION AND REMOVAL OF CONTACT AND SCLERAL LENSES which is hereby incorporated herein by reference in the entirety.

FIELD OF THE INVENTION

The present invention is related to a lens aid for the particular insertion of a large scleral lens, and/or contact lens into the eye. The lens aid of the present invention is referred to herein as a LNSAID™ with LNSCUP™ lens aid system and this lens aid system also referred to as the LNSAID™ Kit.

BACKGROUND OF THE INVENTION

For some people the wearing of smaller conventional contact lenses that only cover a portion of the cornea of the eye may not adequately improve vision and may cause irritation and complications. Therefore, for some, a larger scleral lens that extends over the entire corneal surface and rests on a portion of the sclera (the white portion of the eye) may provide sharper vision especially if damage to the cornea has occurred. The scleral lens can span over the damaged area because of its greater stiffness and durability, and be safe for the eye due to its porosity for oxygen to reach the eye surface. While these larger lenses are more stable in the eye and less likely to accidentally dislodge from the eye, they require additional training and patience to gain comfort to reliably insert the larger diameter scleral lens into the eye. This is of concern because the incorrect insertion of these larger lenses may cause an air bubble or eyelash entrapment between the lens and eye which may irritate and adversely affect the wearer's vision. Incorrect insertion, requires removal of the lens and another try to properly insert the lens which can be discouraging if repeated over and over.

Currently, one common procedure to insert a scleral lens is performed by supporting the lens on one fingertip of one hand, filling the lens with a saline type solution, tilting the head downward by tucking the chin toward the chest and then holding the eyelids open with the other hand and inserting the lens. The eyelids are then released to capture the lens and the fingertip holding the lens is removed. Another method of insertion requires putting two or three fingertips together to form a bipod or tripod to support the lens, adding the saline solution and then inserting the lens with the one hand into the eye while the other hand holds the eyelids open with two fingers spread apart in a "V" shape. For some, these procedures require a level of coordination that is very difficult to attain particularly because the eye has a normal aversion to having anything inserted and making contact with it. Also, the spreading "V" shape is hard to learn so that you do not contaminate your own eyelids with your fingers. In these methods, the fingers are often in the way of a clear view looking down into a mirror; they tend to block a clear view by their required location to hold the scleral lens level with saline filled under the eye just prior to insertion, just when the person inserting the lens needs the best viewing.

There are some insertion tools available such as a lens holder formed as a small cup on the tip of an extended base that may be held in one hand to draw the lens level so saline can be added and held near the eye to insert the lens while the other hand holds the eyelids open. One other type of insertion tool is formed like an O-ring that is placed on top of the fingertip in a horizontal position and the lens is then placed in the O-ring to a level where saline can be added into the lens. The lens on the O-ring is then brought up to the eye for insertion with one hand while the other hand is holding the eyelids open. Another insertion tool uses a ring that may be put around the fingertip. The ring has a small cup to hold the lens and when held level, saline can be added and brought toward the eye for insertion of the lens while the other hand is holding the eyelids open. Another tool is an insertion plunger that allows a user to, if needed, create a small suction through a tubular handle of the plunger to hold the lens on the plunger and then by squeezing the handle force air to release the lens into the eye. One problem with this technique is that the cup supporting the scleral lens can move laterally disturbing the insertion, as you squeeze the base. Also, each of these methods has the fundamental problem of requiring one hand to hold the lens steady and one hand to hold the eyelids open. They all also interfere with a clear view to a mirror due to how the lens is being supported by the hand and fingers. Also, any flinching of either the eyelids or fingertips can result in the lens being dropped, damaged and even lost. The lens must then be retrieved, cleaned, add saline solution again, and the procedure repeated. Another insertion tool of the prior art uses a plunger stand that is in the shape of an upside-down rounded cup made of an opaque material and having a large diameter base. The opaque material and large diameter base block a clear view to a mirror to see the axis of the lens and substantially prevents satisfactory mirror use to assist in the alignment of the lens to the eye. The rounded upper portion of the plunger base stand also will send an accidently falling lens off in a lateral direction possibly off the table to the floor making it difficult to retrieve. The present invention addresses the limitations of these current procedures and provides for a scleral lens to be inserted by a remote one-hand method or a hands-free method so that the eyelids may be held open using both hands while simultaneously providing a clear view to a mirror for optimal vision to align the scleral lens axis with the eye for its proper insertion. This significantly reduces the risk of flinching and dropping of the lens from an unstable fingertip or handheld insertion tool or similar device with view blocking fingers or a large base support.

The added patience and dexterity required to insert a scleral lens using these procedures of the prior art, can be uncomfortable for a user and may deter a user from choosing a scleral lens regardless of the added benefits of improved vision and greater durability. The LNSCUP™ lens aid and LNSAID™ System of the present invention provide safe and effective procedures for a user to much more quickly and easily insert a large diameter contact or large diameter scleral lens.

SUMMARY OF THE INVENTION

The present invention is related to a lens aid referred to herein as a LNSCUP™ and a lens aid support system referred to herein as a LNSAID™ System and/or LNSAID™ Kit. Embodiments of the LNSAID™ lens aid comprise a lens cup and a podium support for the lens being inserted. The lens cup may be of antibacterial material or be treated with an antibacterial coating and be removable from the podium or LNSAID™ System for cleaning or replacement. The LNSCUP™ lens aid provides an upper surface to hold a lens and is preferably of a soft pliable material to apply minimal point pressure against the eye and importantly to flex to conform to the exact position of the eye to help to correctly align and position the lens being inserted within the eye as the eye is brought against the lens and is captured by the eyelids when they are released by the user's fingers. Embodiments of the lens cup may have a softer pliable rim and a more rigid body which can be achieved by the variable thickness or gauge of material, and by a varied density of the materials used to form the lens cup, and by the shape of the lens cup as described herein. Within the center of the upper surface in embodiments of the lens cup, there may be an opening of variable diameters or a thin transparent membrane to allow light up and through the lens cup to glow and assist a user in centering their eye over the lens. In some embodiments, a transparent membrane may be a thin, flexible diaphragm that can also flex inward and outward to adjust pressure on the lens when the lens cup is used as a handheld applicator and maneuvered to insert the lens in the eye. In other embodiments, the center portion may have a clear, warm or tinted colored etched disk configured to scatter light through it to provide an illuminated glowing target for the user to center their eye on the lens during the insertion process. The etched disk may also be of other colors and be diffused so that light is scattered in multiple random directions to cause the disk to appear to glow with light as a very-close-to-eye light-source. The glowing of the etched disk may be especially important for a person with sight in only one eye or for a person with cornea damage or distortion due to disease or a genetic error at birth.

In other embodiments, the lens cup may be constructed with a solid podium that has an opening at its base for the insertion of a finger. In this way, a lens may be easily inserted in the eye by using one finger, such as the longer middle finger so that the other fingers on that hand can be closed out of the way to enhance the mirror view, to maneuver the lens supported on the LNSCUP™ lens aid to the eye. When inserting, the eye is held open with the remaining fingers and/or by using the other hand and the lens is captured in the eye by closing the eyelids. The lens cup may be formed having a diameter that is slightly smaller than the diameter of the lens so that when the lens is positioned and supported on the lens cup the overhang of the lens can be easily grasped by the eyelids. The lens cup may also have smoothly formed radial ridges at the outer edge along the perimeter of the lens cup on which the lens is supported to help eliminate any suction that might be present at the moment of the eyelids grasping of the lens. The slightly raised smoothly formed radial ridges may be included to provide for air to more easily pass between the surface of the lens and the surface of the lens cup, reducing and preventing any significant suction from occurring between the two surfaces at the moment of grasping the lens with the eyelids. The radial ridges are formed as a continuous ripple on the surface of the lens cup without edges or crevices that could trap dirt and germs and facilitates easier cleaning. In some embodiments, a finger-podium has an angled support cylinder to further comfort the hands natural position and assist more easily in positioning the lens for insertion in the eye.

Embodiments of the present invention include a LNSAID™ System that comprises a lens cup, a support podium tube, and a support podium platform base. The LNSAID™ System provides for this support podium platform device that may be held by remotely located fingers that are out of the way of a clear view of the podium tube supporting the lens to be inserted, to assist in inserting the lens positioned on the lens cup in the eye without any visual obstruction by the grasping hand or fingers when looking into a mirror. Alternatively, the LNSAID™ System support platform provides for hands-free insertion of the lens as described herein. Additional features of the lens aid system of the present invention may provide for a support tube that extends as a podium from the support platform and one or more additional storage tubes to be used for holding for example a lens removal tool, saline or other cleansing solution, such as protein cleaner solution vials. In embodiments, a second storage tube may extend to a height that is lower than the first support tube and be positioned on the support platform at a distance that is away from the first support tube. In this manner, the first taller support tube may support the lens cup and lens and the second shorter storage tube may be used to easily grasp and hold the lens aid system with the fingers grasping the shorter storage tube well clear of the face allowing the user to look down the taller support tube without being obscured by the hand which is grasping the shorter storage tube providing for easy positioning of the system for lens insertion using one hand. The shorter support tube makes it easy for the hand to not interfere with the necessary careful movements required to bring the lens up towards the eye carefully and accurately for insertion of the lens using this one-handed technique. In preferred embodiments, the support tube is hollow and transparent with a smooth, polished finish inside and out that has at its base as a convex shape to allow for natural light to be focused as it is directed up and through the support tube to assist in illuminating an opening, membrane or mini-lens that can be within the center portion of a lens cup. The support tube may further have a convex shaped lens at the base of the tube to direct and better focus a powered light source up through the support tube, and to allow placement of the LNSAID™ Kit on a mirror that has a built-in powered light source, referred to as the LNSLITE™ to direct light up through the glass mirror into the tube to illuminate the center of the lens cup, as described herein.

The lens support podium tube is affixed to the stable LNSAID™ System support base platform with the support podium tube extending between 5.08 cm (2 in) to 15.24 cm (6 in) and more preferably around 7.62 cm (3 in) from the platform. The antibacterial lens cup is removable from the support tube for cleaning and replacement due to natural concerns for its physical condition with use and cleanliness. It is apt to have a shorter life than the lens aid system support stand and may need to be replaced on a more frequent basis. The two support tubes may provide storage and may have removable tops and for storage of a possible lens removal tool, saline solution and protein cleaner solution vials making the LNSAID™ System a complete kit that has everything necessary to insert and remove a lens. In some embodiments, the shorter support or storage tube may be of a length to hold a lens removal tool that extends above the top of the tube to make it easier and cleaner to grasp the lens removal tool below the cup and to use it to remove the lens from the eye, while not soiling the top cup portion that comes in contact with the eye.

In some embodiments, the LNSAID™ System comprises a lens cup, a support platform with the support and storage tubes, a mirror referred to as the LNSLITE™ that may include a operable light source. The support platform may be placed on this mirror on a table to provide for a user to more easily maneuver their head when in a sitting position over the support tube by looking directly down the podium tube at their reflection in the mirror to position their eye over the support tube. In some embodiments, the mirror may have a towel under or affixed along its edges that may be spread out with turned up edges on the table to capture a lens that is accidently dislodged and has fallen from the lens cup. In preferred embodiments, a light source is integrally attached below the mirror of the LNSAID™ System with the mirror having a small clear opening through the mirrored surface so that the glass top of the mirror is still in one piece able to hold water above it. The light source and batteries are below and enclosed within a base of the glass mirror referred to herein as the LNSLITE. The LNSAID can be correctly positioned on the mirror with a circular indicator mark to identify the correct location for the light source to be aligned with the base of the podium support tube to allow direct light from the light source up through the mirror glass up the podium support tube and through the opening, membrane or etched disk of the lens cup. The light source may be a low power LED light that is battery powered to provide for easy portability of the mirror. The LNSLITE mirror has a built-in push button on/off switch that allows for easy and proper positioning of the LNSAID podium support tube on any table with the person in a comfortable sitting position to lean a bit forward and align their eye with the podium support tube holding the scleral lens ready for insertion. The light source, batteries and wiring are completely protected from any naturally spilled saline that results from the insertion process, and that is captured by the mirror framed surface for easy wipe up. The light source may have one or more filters such as of a warm color for example green or gray clear tinted plastic to reduce brightness from the LED light. The filters are preferably fixed but may be removable for a user to select the proper tint to adjust the brightness based on their preference, eyesight and personal needs.

It is a feature and advantage of the present invention to provide a lens aid system having a support stand that may standalone without requiring a user to hold the support stand, the support stand holding preferably a scleral lens or contact lens within a lens cup to allow for a safe hands-free insertion technique of the lens by looking down on the top with a clear view down or surface on which on the LNSAID™ system is sitting, letting a person's neck muscles control the insertion of the lens into the eye, and freeing both hands to have one hand hold the upper eyelid open and the second hand to hold the lower eyelid open. Because a scleral lens has a larger diameter than a typical soft lens, using both hands may significantly aid in the insertion of the lens particularly where even if a few eyelashes being captured under the lens will result in failure of proper insertion.

In embodiments of the lens aid system a soft pliable lens cup applies minimal pressure against the eye, and importantly flexes at the immediate point of contact with the eye to correctly align the position of the lens within the eye as the eye is brought against the lens and is captured by the eyelids as they are released by the user's fingers.

In embodiments, the lens cup may have smooth continuous ripples or ridges that allow the lens to be removed from the lens cup more easily by allowing air to enter under the edge of the lens and between the ridges to reduce the chances of any suction between the lens and lens cup that may occur.

Embodiments of the lens cup are made of antibacterial material such as a medical grade polypropylene, a soft pliable plastic silicone, closed cell waterproof foam, or rubber like material with soft near forty (40) durometer qualities or be treated with an antibacterial coating.

Embodiments of the lens cup may be removable from the lens aid system for cleaning or replacement.

In embodiments, the lens cup may have crosshair lines along the curved surface of the cup to assist the user in determining the proper positioning and centering of their eye over the lens aid and support tube of the lens aid system for proper alignment of the lens for insertion.

In embodiments, the lens aid system may provide tools for both the insertion and removal of the scleral lens with storage compartments for the lens removal tool and two vials one of saline, the other of a cleansing fluid to keep them all easily accessible.

In embodiments, the lens support stand or podium of the lens aid system may be vertically straight up long and narrow as a podium tube base to enhance an ideal clear view of the axis of this support podium tube with its lens cup and lens and be transparent so that the lens aid system may be placed on a mirror to aid in looking down, seeing the podium axis as a double length with the mirror and seeing quickly and clearly the exact and proper axis for positioning the eye over the lens for insertion of the scleral lens.

Embodiments of the lens aid system may provide a mirror that has a built-in powered light source, referred to as the LNSLITE™ to direct light up through the glass mirror into the tube to illuminate the center of the lens cup, as described herein.

Embodiments of the lens insertion aid comprise a lens cup of a pliable material; and wherein a lens is placed on the lens cup and an eye is brought forward against the lens compressing the pliable lens cup material which in moving adjusts the axis of the lens as the lens is slightly inserted into the eye to provide exact proper alignment of the lens within the eye just before the moment of insertion. The pliable material of the lens cup of the lens insertion aid is antibacterial, antimicrobial, polypropylene, a soft pliable plastic silicone or rubber like material with soft durometer qualities. The lens cup material also meets biocompatible requirements and certifications under for example the United States Pharmacopeia (USP) Class VI standards or under other similar regulatory guidelines for biological reactivity for materials in contact with human tissue. The lens cup of the lens insertion aid may have a channel forming a column shaped lower surface for the insertion of the column into a podium.

The present invention is related to a lens insertion aid, comprising a lens cup of a pliable material having a parabolic curvature configured to flex to adjust the axis of the lens at the immediate point of contact of a lens with the eye to correctly align the position of the lens within the eye as the eye is brought against the lens and is captured by the eyelids. The pliable material of the lens cup of the lens insertion aid is from a group consisting of antibacterial, antimicrobial, soft, pliable type plastic, polymer, silicone, and other medical grade material, with soft durometer qualities. The lens insertion aid comprises greater stiffness at a base of the parabolic curvature that transitions to greater flexibility at the top of the parabolic curvature to rapidly flex to rotate the lens on its axis to have the lens make complete contact and full surround contact to the sclera of the eye when using a scleral lens. The lens cup of the lens insertion aid comprising a rim at the top of the parabolic curvature configured to flex and a central portion at the base of the parabolic curvature configured to be rigid. The lens cup comprising interior surfaces of one parabolic curvature and exterior walls of a different parabolic curvature, the exterior walls configured to decrease in stiffness and increase in flexibility from the central portion to the rim of the lens cup. The lens insertion aid may comprise an opening through the central portion at the base of the of the parabolic curvature and the opening may have tapered walls. The lens insertion aid may comprise a filter sealing the opening in the central portion, the filter having etching configured to scatter light and glow from ambient light or from light from a powered light source. The lens insertion aid may comprise a membrane sealing the opening in the central portion, the membrane configured to flex up or down and glow from ambient light or from light from a powered light source. The rime of the lens cup of the lens insertion aid may comprise smooth rounded ridges that do not have crevices or creases. The lens cup of the lens insertion aid may be disposable. The lens cup may comprise an upper portion having the parabolic curvature and a base, the upper portion configured to have a diameter that is less than the diameter of a lens to provide an overhang to assist the eyelids in more easily capturing the lens. The base of the lens cup may comprise a diameter that is smaller than the diameter of a support tube, the base configured for attachment to a support tube for hands-free insertion of a lens. The base of the lens cup may comprise a conical slope and the support tube may comprise a conical taper formed at the top of the support tube. The lens insertion aid may comprise a podium and the base of the lens cup is configured for insertion into the podium. The lens insertion aid wherein the base is of a standard size configured for insertion into a podium of a standard size. The lens insertion aid wherein the podium having a lens cup support and finger-mount, the finger-mount configured to be of a diameter to accommodate different sized fingers. The lens insertion aid wherein the lens cup support is at an angle from the vertical axis of the finger-mount and the angle is in a range of between 120° and 150° and more preferably 135°.

The present invention is also related to a lens insertion system, comprising a platform; a support tube affixed to the platform; a lens cup affixed to the support tube, and the lens insertion system configured for hands-free insertion of a lens within the eye allowing for the eyelids to be opened using one or both hands for easier insertion of the lens. The platform of the lens insertion system may be a transparent material and may have a convex lens in its base to focus light through the support tube to the lens cup. The lens cup of the lens insertion system may be removably attached to the support tube. In embodiments of the tens insertion system, a corner of the platform extends at an angle that is 90 degrees or less and the support tube is attached to the corner of the platform providing for a user to place the lens insertion aid on a mirror and have a double length clear view down and around a large portion of the vertical axis support tube using one or both eyes to properly align the eye over the lens. In other embodiments of the lens insertion system the platform has a circular shape under the storage tube and a stabilizer brace that extends to the support tube providing a viewing area of up to 358 degrees for a user to place the lens insertion aid on a mirror and have a double length clear view down into a mirror of the vertical axis of the support tube using one or both eyes to properly align the eye over the lens. The lens insertion system may comprise a storage tube, one of at least a lens removal tool, saline solution, and protein cleanser, a stabilizer brace and/or a mirror. The lens insertion system may comprise a powered light source enclosed within a mirror with light from the light source passing through the glass of the mirror through a hole in the reflective material of the mirror.

The present invention is further related to a method for the handsfree insertion of a lens into an eye, comprising attaching a lens cup to a support tube; supporting a lens on a lens cup, the lens cup of a soft pliable, material having a parabolic curvature configured to flex to adjust the axis of the lens at the immediate point of contact of a lens with the eye to correctly align the position of the lens within the eye as the eye is brought against the lens and is captured by the eyelids; adding saline solution; grasping the eyelid with two hands to open the eye; moving the head down to a horizontal position of the eyes; moving the eye to the lens; pressing the eye against the lens thereby flexing the lens cup to adjust the axis of the lens and align the lens within the eye in the proper position on the eye to have the lens make complete contact and full surround contact to the sclera of the eye when using a scleral lens; releasing the two hands from holding the eyelids; and grasping the lens with the eyelids.

These and other features, advantages and improvements according to this invention will be better understood by reference to the following detailed description and accompanying drawings.

BRIEF DESCRIPTION OF THE DRAWINGS

The invention, together with further objects, features, aspects and advantages thereof will be more fully understood and appreciated by consideration of the following description in conjunction with the accompanying drawings in which the respective elements bear the same reference numerals throughout the various views.

FIG. 5A is a top perspective view of an embodiment of the LNSCUP™ lens aid of the present invention;

FIG. 5B is a bottom perspective view of an embodiment of the LNSCUP™ lens aid of the present invention;

FIG. 16A is a top view of an embodiment of the lens cup in the embodiment of the LNSAID™ System shown in FIG. 16C;

FIG. 16B is a top view of an embodiment of a storage tube cap in an embodiment of the LNSAID™ System shown in FIG. 16C;

FIG. 16C is an exploded view of an embodiment of the LNSAID™ System with the lens cup, lens cup podium, comprising the support tube, storage tube and platform and the cap for the storage tube;

FIG. 16D is a top view of an embodiment of the platform of the lens cup podium in the embodiment of the LNSAID™ System shown in FIG. 16C;

FIG. 27A is a perspective view of a further embodiment of the LNSAID™ System of the present invention with a lens removal tool in a storage tube;

FIG. 28A is a perspective view of an embodiment of a lens cup with an extended tapered base in a multi-portioned applicator;

FIG. 28B is a cross-sectional view of an embodiment of a lens cup applicator of FIG. 28A;

FIG. 28C is a cross-sectional view of the embodiment of the lens cup of the lens cup applicator of FIG. 28B;

FIG. 28D is a top view of the embodiment of a lens cup applicator of FIG. 28A;

FIG. 28E is a bottom view of the embodiment of a lens cup applicator of FIG. 28A;

FIG. 31 is a cross-sectional view of a further embodiment of a lens cup applicator in an embodiment of the present invention;

FIG. 31A is an inset of a filter used in the further embodiment of a lens cup applicator shown in FIG. 31;

FIG. 31B is a top view of the further embodiment of the lens cup applicator of FIG. 31;

FIG. 31C is a cross-sectional view of the further embodiment of the lens cup applicator of FIG. 31;

FIG. 31D is a bottom view of the further embodiment of the lens cup applicator of FIG. 31;

FIG. 31E is a perspective view of the further embodiment of the lens cup applicator of FIG. 31;

FIG. 32A is a cross-sectional view of a further embodiment of a lens cup applicator of FIG. 31 for insertion into a further embodiment of the lens cup podium with a support tube having a conical sloping inner wall in an embodiment of the present invention;

FIG. 32B is a cross-sectional view of a further embodiment of a lens cup applicator of FIG. 31 inserted into a further embodiment of the lens cup podium with a support tube having a conical sloping inner wall in an embodiment of the present invention;

FIG. 33 is a top view of a further embodiment of a LNSAID System of the present invention with a mirror and powered light source;

FIG. 34 is an elevation view of the further embodiment of a LNSAID System of FIG. 33;

FIG. 34A is an inset of the lamp of the powered light source of the further embodiment of a LNSAID System of FIG. 33;

FIG. 35 is a top view of the further embodiment of a LNSAID System of the present invention of FIG. 33;

FIG. 36 is an elevation view of the further embodiment of a LNSAID System of FIG. 33;

FIG. 36A is an inset of an embodiment of a lens in the base of the support tube in the further embodiment of a LNSAID System of FIG. 33;

FIG. 36B is an inset of an embodiment of a lens in the base of the support tube in the further embodiment of a LNSAID System of FIG. 33;

FIG. 38A is a cross-sectional view of an embodiment of a lens cup applicator with a membrane in a raised position;

FIG. 38B is a perspective view of the embodiment of a lens cup applicator of FIG. 38A with the membrane in a raised position;

FIG. 38C is a cross-sectional view of the embodiment of a lens cup applicator of FIG. 38A with the membrane in a lowered position;

FIG. 38D is a perspective view of the embodiment of a lens cup applicator of FIG. 38A with the membrane in a lowered position;

FIG. 39A is a cross-sectional view of a further embodiment of a lens cup applicator of FIGS. 38A-38D for insertion into a further embodiment of the lens cup podium with a support tube having a ledge in an embodiment of the present invention; and FIG. 39B is a cross-sectional view of a further embodiment of a lens cup applicator of FIGS. 38A-38D inserted into the further embodiment of the lens cup podium with a support tube having a ledge in an embodiment of the present invention.

DETAILED DESCRIPTION OF THE PREFERRED EMBODIMENTS

Figure 1A:
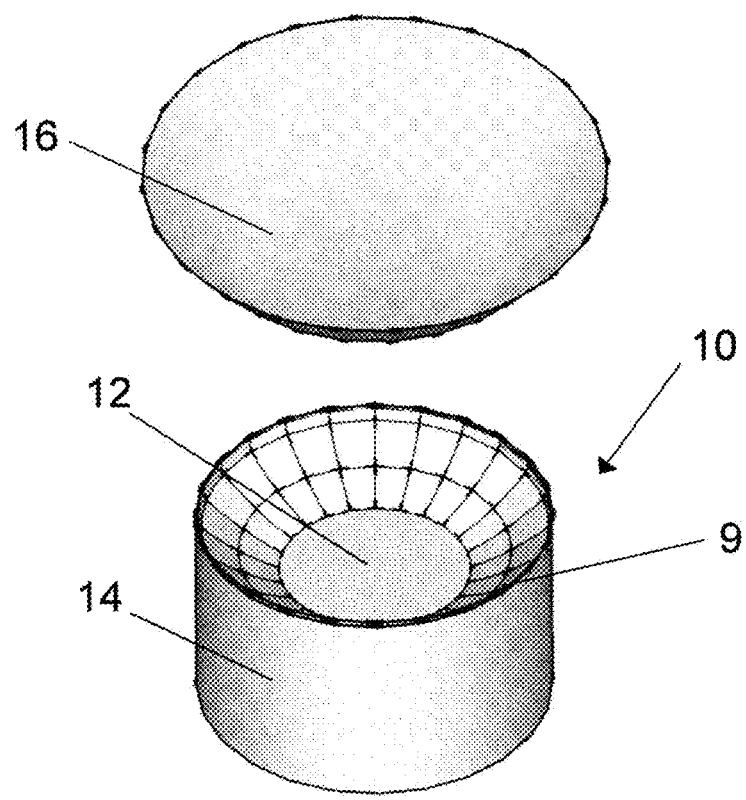
FIG. 1A is a perspective view of an embodiment of the lens cup of the present invention and a lens.
Figure 1B:
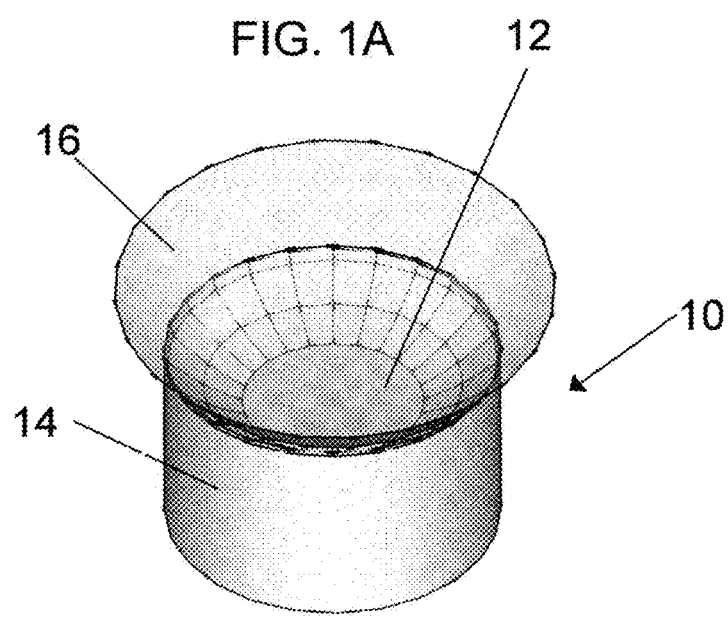
FIG. 1B is a perspective view of an embodiment of the lens cup of the present invention with a lens positioned and supported on the lens cup.

An embodiment of a lens cup 10 of the present invention is shown in FIG. 1A. Embodiments of the lens cup 10 have an upper surface 12 and a cylindrical body 14. The upper surface 12 is formed with parabolic curved walls and a center portion providing for a large diameter scleral or contact lens 16 to be placed and supported along the edge 9 of the upper surface 12 as shown in FIG. 1B. The lens cup 10 is made from antibacterial, antimicrobial material such as a medical grade polypropylene, a soft pliable plastic silicone, closed cell foam, or rubber like material with soft near forty (40) durometer qualities or another type of material that will compress and allow its form to be altered easily as the lens 16 sitting on top is brought against the eye. This edge flexibility feature is to allow and provide for the absolute correct precision and final alignment of the axis of the lens 16 at the immediate point where the lens 16 initially makes contact with the eye. The soft and pliable lens cup 10 material also prevents damage to the eye and/or scratching of the lens 16. The lens cup 10 may be formed, cut, or molded with a variety of shapes from a shallow curvature to a deeply cut elliptically shaped or preferably parabolic curvature as described herein to cradle the lens 16 in the lens cup 10 providing safety to the eye of the user and a personal precision fitting experience of the lens 16 to the eye's surface. The soft pliable material allows the lens cup 10 to readily compress and comfortably locates the lens 16 in the eye in a unique and very different manner from the hard-plastic shaped insertion tools of the prior art that may fail to easily adjust the placement of the lens 16 within the eye and provide no comfort to the eye when the eye is pressed against the lens 16 as the lens 16 is inserted, especially with the hands free method of moving the eye down for insertion when both hands can be used to more easily open the eye.

Figure 2:
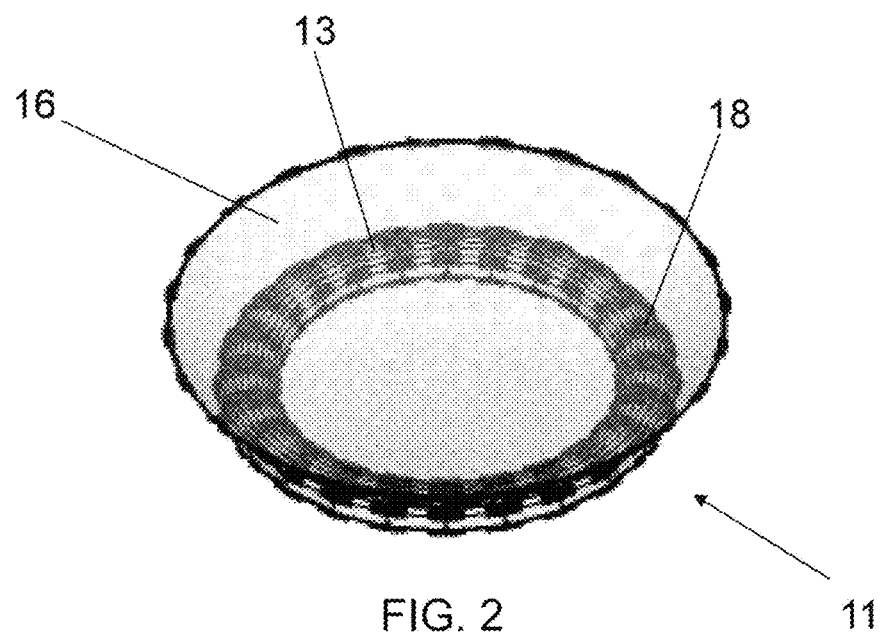
FIG. 2 is a perspective view of another embodiment of the lens cup of the present invention with a lens.
Figure 3:
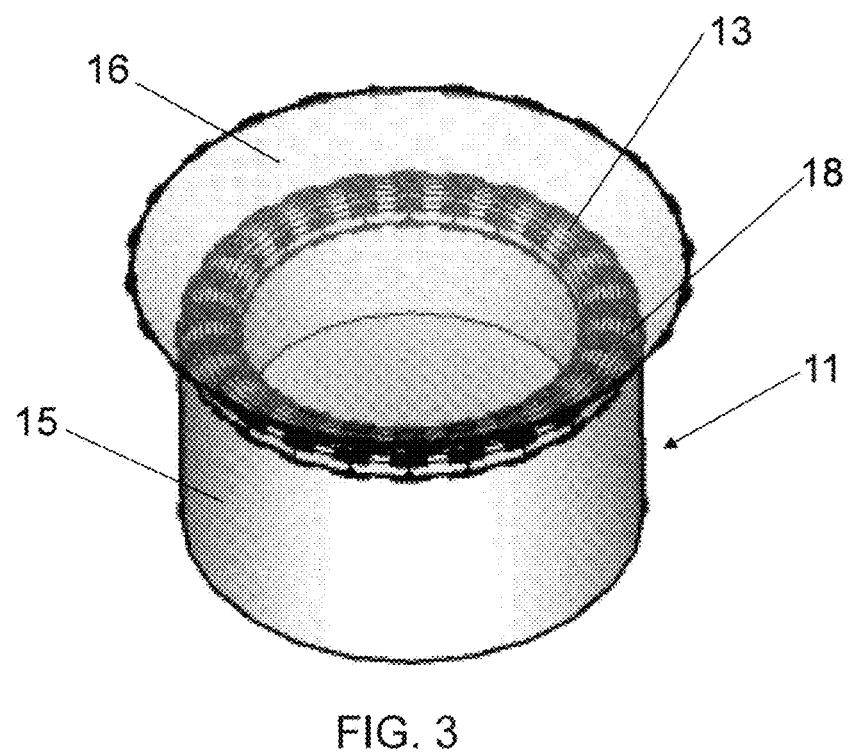
FIG. 3 is a perspective view of a further embodiment of the lens cup of the present invention with a lens.

In other embodiments, a lens support may simply be formed as a lens ring 11 using the soft pliable material. The lens ring 11 may be supported on the middle or index finger to maneuver the lens 16 for insertion in the eye, as shown in FIG. 2. The upper surface 13 of the ring 11 may be smooth or preferably have a series of tiny smoothly formed rounded ridges 18 extending radially around the ring's upper surface 13. In other embodiments, the lens ring 11 may have a cylindrical wall 15 providing a region for the user to grip the lens ring 11 and place it on a fingertip, as shown in FIG. 3. The supple surface of the lens cup 10 or lens ring 11 of the present invention provides a distinct advantage of allowing the lens 16 when pressed against the eye to slightly adjust its axis in the soft lens cup 10 or lens ring 11 an adjustment made within the soft pliable material that facilitates exact proper alignment of the lens 16 against the eye. Diminishing or removing the risk of misalignment or capture of air bubbles or eyelashes that can cause irritation and blurriness and require the user to remove the lens and start the insertion process again. The lens cup 10 or lens ring 11 of the present invention therefore provides improvements over the insertion tools of the prior art.

Figure 4:
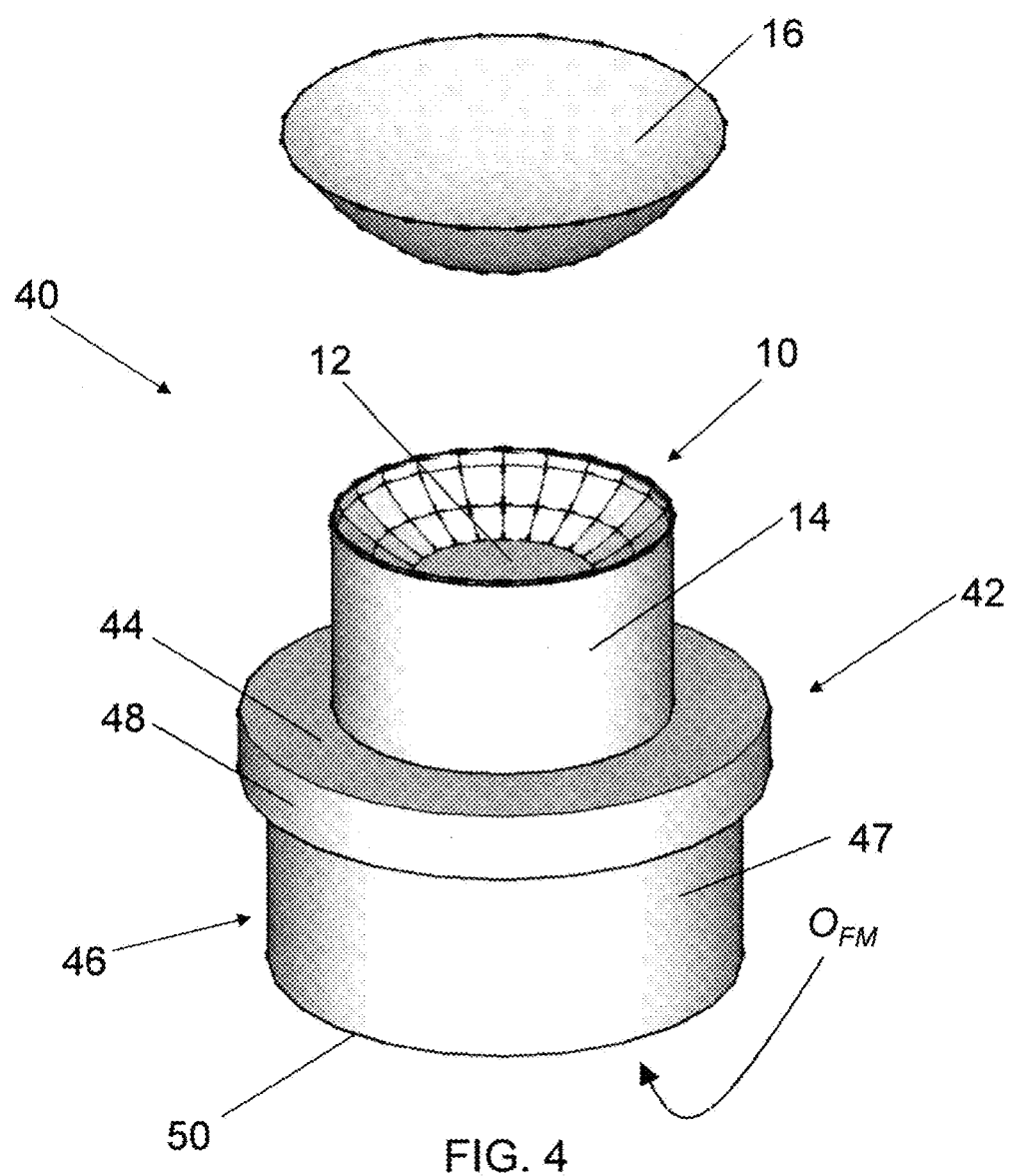
FIG. 4 is a perspective view of an embodiment of the LNSCUP™ lens aid of the present invention.

In further combining the superior lens support of the present invention with the LNSCUP™ lens aid 40 and the LNSAID System 80, as described herein, the insertion of the lens 16 is performed much more easily than any of the insertion methods previously used or described by the prior art. An embodiment of the LNSCUP™ lens aid 40 is shown in FIG. 4. In this embodiment, the LNSCUP™ lens aid 40 comprises the lens cup 10 and a podium 42 having a lens cup support 44 for the lens cup 10, a finger-mount 46, and a transition portion 48. The finger-mount 46 is formed by a cylindrical sidewall 47 that creates an opening. $O_{FM}$ at the base 50 of the podium 42. The LNSCUP™ lens aid 40 provides for a user to insert their middle longest finger or index finger into the opening $O_{FM}$ and maneuver the lens 16 to insert the lens 16 into their eye. In some embodiments, the LNSCUP™ lens aid 40, the lens cup 10 may be molded or be otherwise permanently affixed to the podium to provide for the LNSCUP™ lens aid 40 to be formed as a single piece entirely out of soft pliable medical grade material. In such embodiments, the LNSCUP™ lens aid 40 may be disposable and be discarded after any number of uses or when soiled.

In other embodiments, the lens cup 10 may be removable from the LNSCUP™ lens aid 40, as shown in FIG. 5A, where the lens cup 10 may slide over the lens cup support 44 of the podium 42. In other embodiments, the lens cup 10 may slide into the lens cup support 44, as shown in FIG. 5B. The same finger-mount podium 42 may therefore be used with a variety of lens cups 10 having of different diameters and dimensions. At the base 50 of the podium 42, as shown in FIG. 5B, the cylindrical sidewall 47 of the finger-mount 46 extends to a rim 54 forming the opening $O_{FM}$ that may have an internal diameter $D_{FM}$ of different dimensions to accommodate user's having different finger sizes. Through the selection of the proper size, the LNSCUP™ lens aid 40 will be wide enough and long enough to seat securely on the fingertip with a secure frictional fit so that when moving the finger towards the eye, the LNSCUP™ lens aid 40 will not loosen or tilt. The podium 42 may be made of soft or hard plastic, or hard closed cell foam and may be textured along the interior surface 56 of the finger-mount 46 to provide a secure frictional fit on the finger of the user.

Figure 6A:
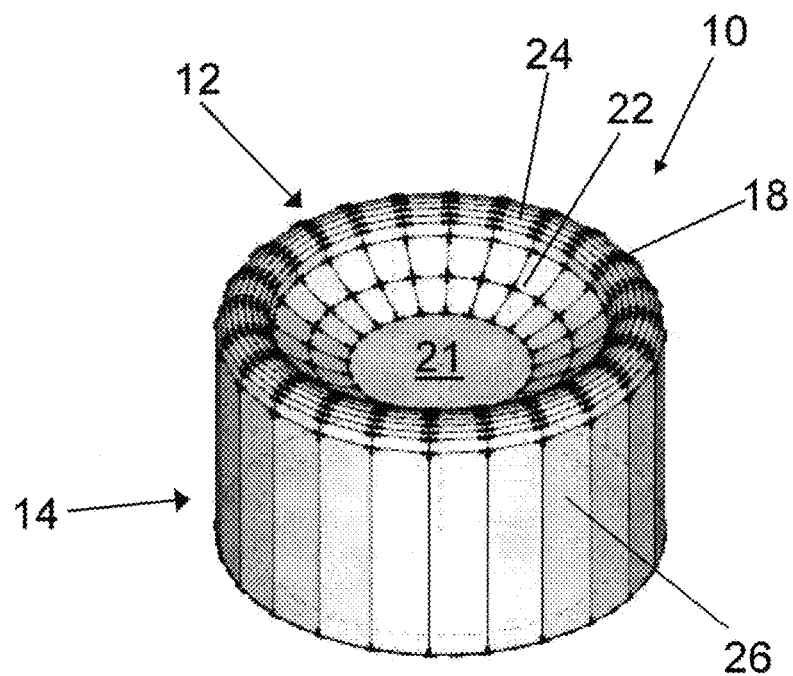
FIG. 6A is a top perspective view of a still further embodiment of the lens cup of the present invention.
Figure 6B:
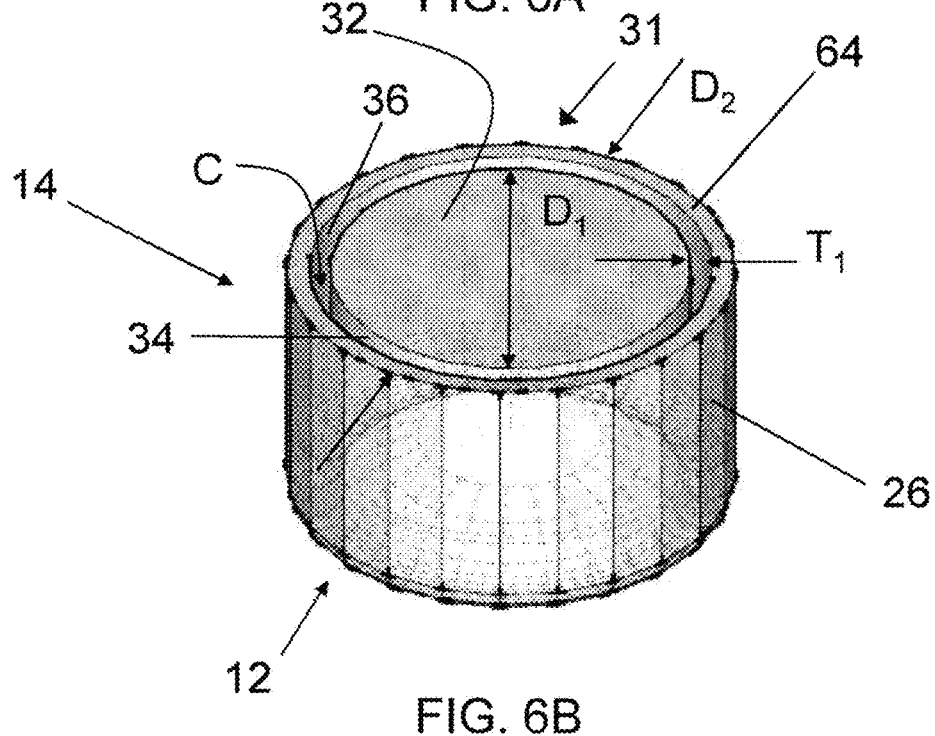
FIG. 6B is a bottom perspective view of the still further embodiment of the lens cup.

In an embodiment as shown in FIG. 6A, the lens cup 10 is of the same soft pliable material as previously described with a curved upper surface 12 that may have a small flat center portion 21, parabolic curvature along the mid-portion 22 and a rounded rim 24. The rim 24 may be continuously even and level or in some embodiments have smooth surfaced ridges 18 that may be formed and extend along the rim 24 of the lens cup 10. The ridges 18 may be formed as slight protrusions, nubs, or preferably as smoothly rounded curves that are raised slightly above the surface of the mid-portion 22 and rim 24 in order to support the lens 16. The ridges 18 are smooth ripples along the rim 24 without any creases or crevices that could collect and hold dirt and germs making cleaning difficult. The ridges 18 allow air to enter under the bottom surface 28 of the lens 16 and between the ridges 18 to prevent the lens 16 from adhering to the lens cup 10 through the possibility of suction. As shown in FIG. 6B, the bottom 31 of the lens cup 10 may have a flat lower surface 32 that provides for the lens cup 10 to sit level on any surface to assist a user in inserting a lens 16 if the lens cup 10 is used without the LNSCUP™ lens aid 40 or LNSAID™ System 80. The body 14 may have a cylindrical sidewall 26 that extends down from the upper surface 12 to the flat bottom 31. A channel C may be formed in the bottom 31 of the lens cup 10 to slide the lens cup 10 over the edge 43 of the tubular lens cup support portion 44 to secure the lens cup 10 to the podium 42, as shown in FIG. 5A. The channel C may be molded or be formed by removing material from a solid tubular piece of the soft medical grade material of the lens cup 10 so that a column with an exterior wall 34 is surrounded by an interior surface 36 of sidewall 26. The diameter $D_1$ of the column is therefore minimally smaller than the inside diameter of the lens cup support 44 of the podium 42 or of the diameter of a support tube 84 of the LNSAID™ System 80. The thickness $T_1$ of the channel C is minimally larger than the thickness of the cylindrical wall of the lens cup support 44 or support tube 84 as described herein. The body 14 of the lens cup 10 may be of any suitable diameter $D_2$ to extend the sidewall 26 to provide a soft pliable cushion along the top edge 43 and upper portion of the lens cup support 44 of the podium 42 or of the support tube 84. By using a channel C and sliding the lens cup 10 along the cylindrical wall 26, the lens cup 10 is securely affixed in place with the column maintaining a tight frictional fit and preventing the lens cup 10 from moving or tilting when the eye is pressed against the lens 16. This type of attachment for the lens cup 10 assures that the lens 16 can move slightly within the pliable top portion 12 of the lens cup 10, allowing minor exact final lens axis adjustments, while the lens cup 10 remains stationary to provide for the lens 16 to be properly located along the surface of the eye.

Figure 7A:
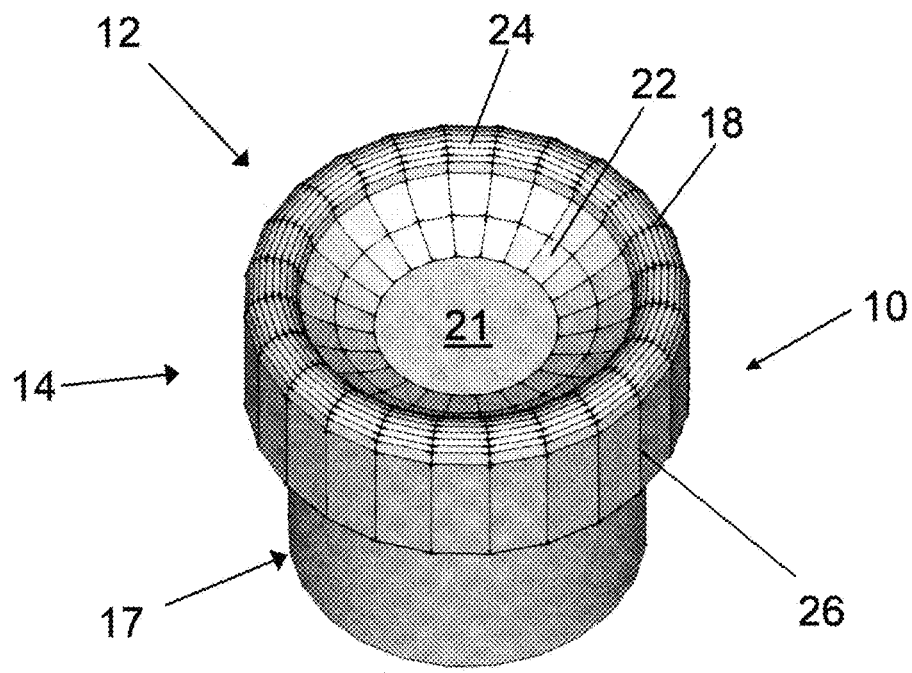
FIG. 7A is a top perspective view of a still further embodiment of the lens cup of the present invention.
Figure 7B:
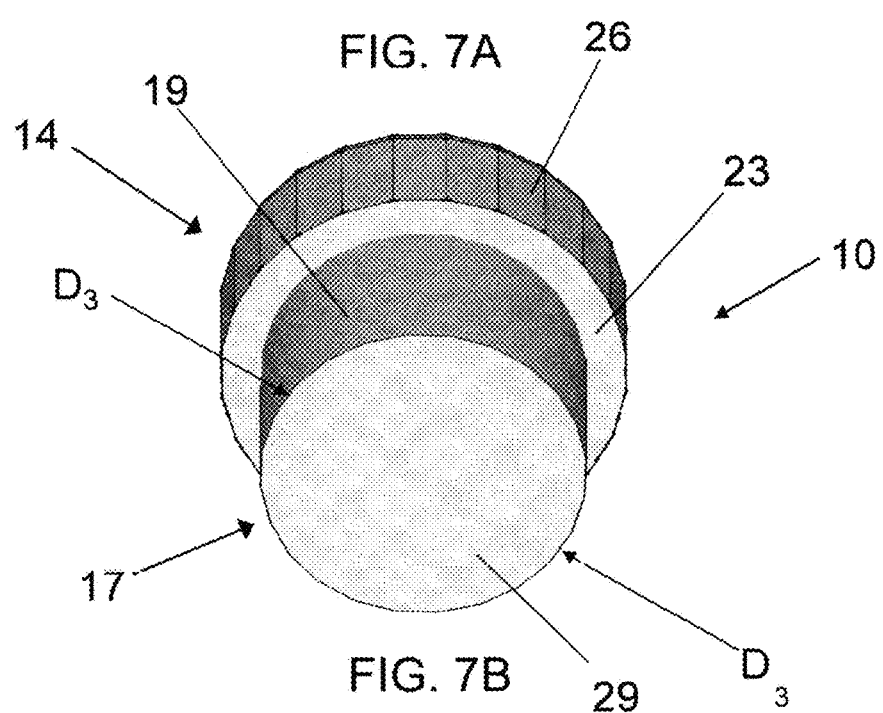
FIG. 7B is a bottom perspective view of the still further embodiment of the lens cup.

In other embodiments, the lens cup 10 is formed to easily insert and to be secure and stable on the podium 42 of the LNSCUP™ lens aid 40 as shown in FIG. 5B or on support tube 84 of the LNSAID™ System 80. The lens cup 10 is of the same soft pliable medical grade material with the upper surface 12 and may have a small flat center portion 21, where there may be a hole, a parabolic curvature in the mid-portion 22 and rounded rim 24 that is continuous and level. The lens cup 10 may also be provided with smoothly formed ripples or ridges 18 on the rim 24 of the upper surface 12 and a cylindrical wall 26 that forms a body 14. In this further embodiment, the lens cup 10 also has a base 17 that extends from the body 14, as shown in FIG. 7A. The base 17 may have a cylindrical sidewall 19 that extends a suitable distance from the body 14 to a flat bottom 29. The base 17 may act as a holder for a user to maneuver the lens cup 10 and insert a lens 16 into the eye without the aid of the LNSCUP™ lens aid 40 or the LNSAID™ System 80 but preferably the base 17 is of slightly smaller diameter $D_3$ than the tubular lens cup support 44 of the podium 42 or of the support tube 84 to be easily inserted and used with the LNSCUP™ lens aid 40 or the LNSAID™ System 80 to provide for optimal viewing to a mirror without obstruction. The extended length of base 17 secures the lens cup 10 with a tight frictional fit on the podium 42 or within the support tube 84. The cylindrical sidewall 26 of the body 14 may extend to any length and may in some embodiments extend only a minimal length from the rim 24 of the upper surface as shown in FIG. 5A. The lens cup 10 in such embodiments is simply removed from the podium 42 by extending a finger through the opening $O_{FM}$ and pushing the lens cup 10 or by grasping the exposed side walls and pulling the lens cup out to free it from the lens cup support 44. The body 14 may therefore be of a smaller diameter or be the same diameter as the base 17, or be preferably of a larger diameter to provide a surface 23 to rest on the edge 43 of the lens cup support 44 or edge 83 of the support tube 84. A longer length body 14 also provides for a user grip the cylindrical sidewalls 26 of the body 14 and push or pull the lens cup 10 to install or remove the lens cup from the LNSCUP™ lens aid 40 or the LNSAID™ System 80.

Figure 8:
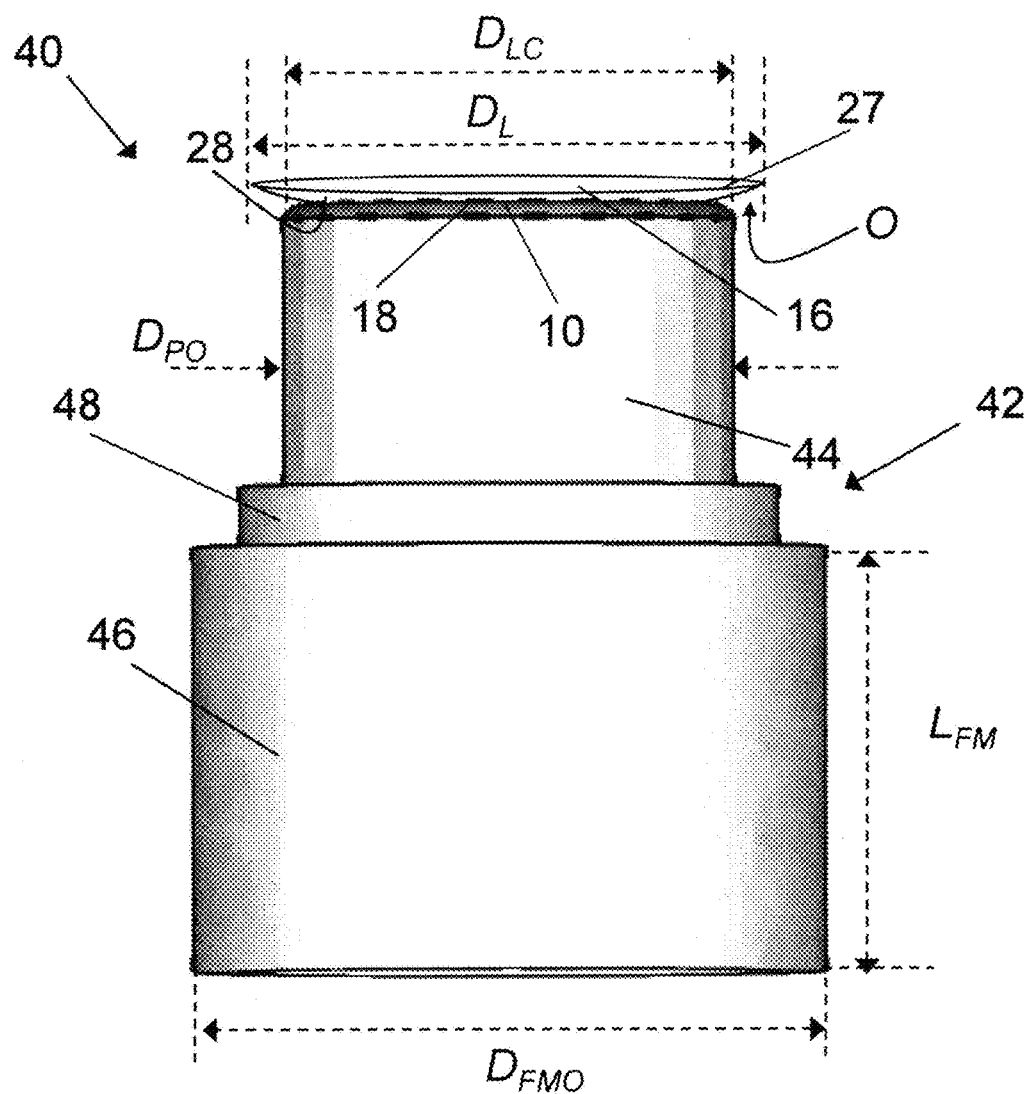
FIG. 8 is a side elevation view of an embodiment of the LNSCUP™ lens aid of the present invention.

In some embodiments, the outer diameter $D_3$ of the base 17, the outer diameter $D_2$ of the body 14 and the diameter $D_{LC}$ of the upper surface portion 12 of the lens cup 10 may all be of different lengths with the diameter $D_{LC}$ of the lens cup 10 being of any suitable diameter that is smaller than the diameter $D_L$ of any particular lens 16, as shown FIG. 8. The lens cup 10 may therefore be provided in different sizes for scleral and contact lenses of different diameters. For example, typical scleral lenses vary from 14.9 mm (0.587") to 24 mm (0.945") in diameter and typical soft lenses may vary from 14.2 mm (0.229") to 14.5 mm (0.571") in diameter. The upper portion 12 of the lens cup 10 may therefore have different diameters $D_{LC}$ and be available in multiple sizes such as small, medium, and large to accommodate scleral and contact lenses of different sizes. The diameter $D_2$ of the body 14 and/or base 17 may in some embodiments be a fixed diameter while the diameter $D_{LC}$ of the upper portion 12 is varied. The fixed diameter $D_2$ of the body 14 with in some embodiments a fixed diameter $D_3$ of the base 17 provides for different sizes of lens cups 10 to be used with a single size of podium 42 or support tube 84. As an example of the flexibility of these embodiments, some embodiments of the lens cup 10 may be formed with a minimal cylindrical wall 26 forming a shortened body 14 but provide an extended cylindrical wall 19 forming the base 17 to insert the base 17 of the lens cup 10 within the tubular lens cup support 44 or support tube 84 without the surrounding cylindrical sidewall 26 of the body 14. In these embodiments, the upper surface portion 12 of the lens cup 10 may be of a larger or smaller diameter $D_{LC}$ to extend to or beyond the outer diameter $D_{PO}$ of the podium 42 as shown in FIG. 8.

This important feature of the present invention of offering the lens cup 10 in different diameters, provides for the diameter $D_{LC}$ of the lens cup 10 to be smaller than the diameter of the lens 16 and create an overhang O of the lens 16, as shown in FIG. 8. In this manner, the lens cup 10 provides for the eye to compress against the lens 16 as the eyelids are held fully opened, and the overhang O provides for the eyelid to surround and capture the lens 16.

Embodiments of the LNSCUP™ lens aid 40 comprise the lens cup 10 and the podium 42. The podium 42 may be formed with an upper tubular lens cup support 44 to support the lens cup 10 and a finger-mount 46. The diameter $D_{PO}$ of the tubular lens cup support 44 may be the same as the diameter $D_{FM}$ of the finger-mount 46 but more preferably the tubular lens cup support 44 is of a fixed diameter $D_{PO}$ and of an adequate length to mate with the diameter and length of the body 14 and/or base 17 of the lens cup 10 so that the lens cup 10 may be inserted into, on or around the lens cup support 44. The diameter $D_{FM}$ of the finger-mount 46 may be larger or smaller in diameter than the tubular lens cup support 44 and preferably is offered in different diameters to accommodate users having different sized fingers. The length $L_{FM}$ of the finger-mount 46 of the podium 42 may also be in different lengths to accommodate finger tips of different lengths. By providing different diameters and lengths of the finger-mount 46 of the podium 42, the LNSCUP™ lens aid 40 may for example be offered in small, medium and large sizes.

Figure 9:
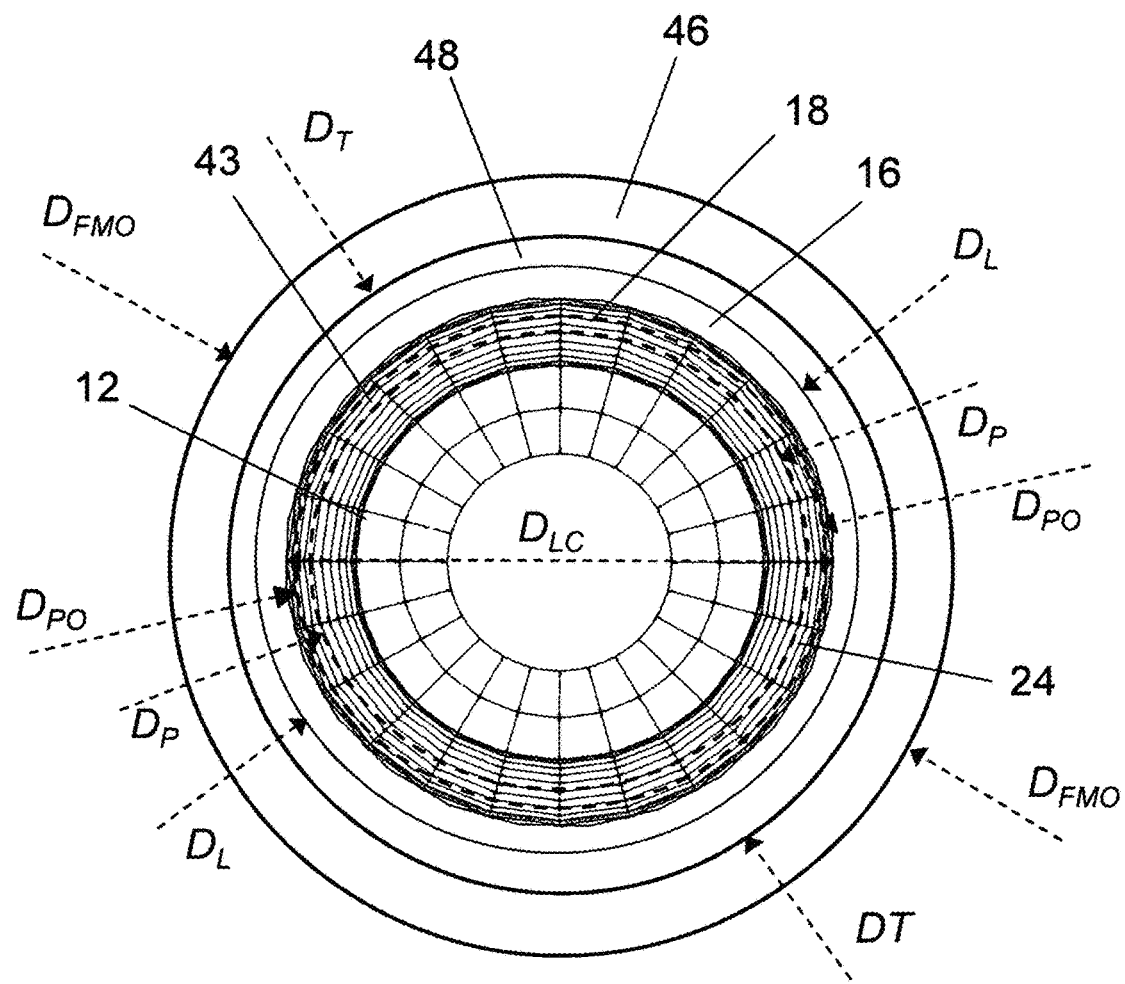
FIG. 9 is a top view of an embodiment of the LNSCUP™ lens aid of the present invention.

The podium 42 may have an intermediate transition portion 48 that may have one or more steps or be slanted or rounded to connect the different diameters of the tubular lens cup support 44 and finger-mount 46. In some embodiments, the podium 42 is hollow and the opening from the finger-mount 46 extends through the tubular lens cup support 44. In other embodiments, the transition portion 48 forms a barrier between the tubular lens cup support 44 and the finger-mount 46 openings to provide rigidity and strength to the podium 42. As shown in a top view in FIG. 9, the diameter $D_{LC}$ of the upper surface portion 12 of lens cup 10 may be larger than the inside diameter $D_P$ and/or the outside diameter $D_{PO}$ of the tubular lens cup support 44 to have the rim 24 of the lens cup 10 extend out over the upper edge 43 of the tubular lens cup support 44. The diameter $D_L$ of the lens 16 extends beyond the diameter $D_{LC}$ of the upper surface portion 12 of the lens cup 10 to create the overhang O. The diameter $D_T$ of the transition portion 48 may be larger than the outside diameter $D_{PO}$ of the tubular lens cup support 44 and smaller than the outside diameter $D_{FMO}$ of the finger-mount 46.

Figure 10:
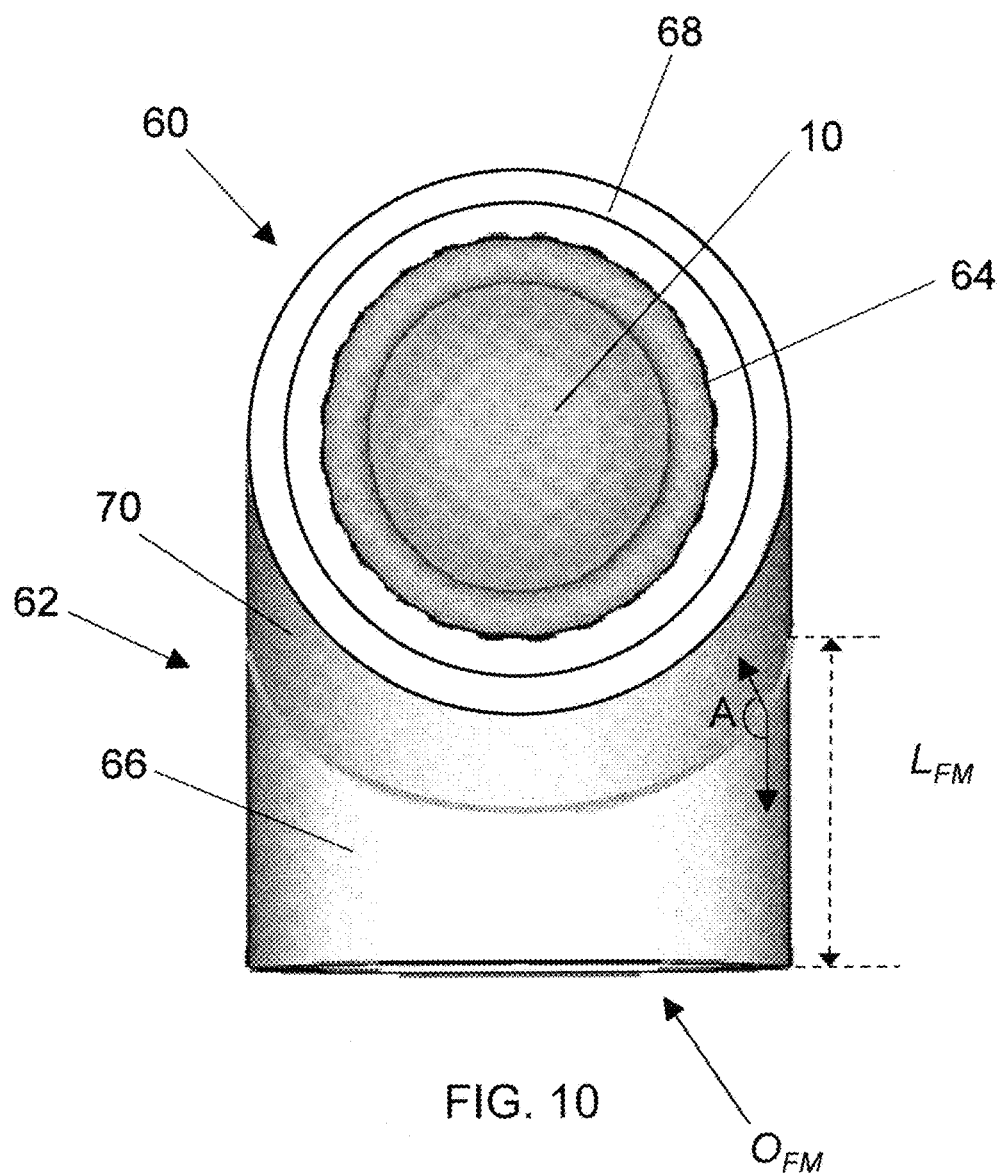
FIG. 10 is a perspective view of another embodiment of the LNSCUP™ lens aid of the present invention having an angular extension.
Figure 11A:
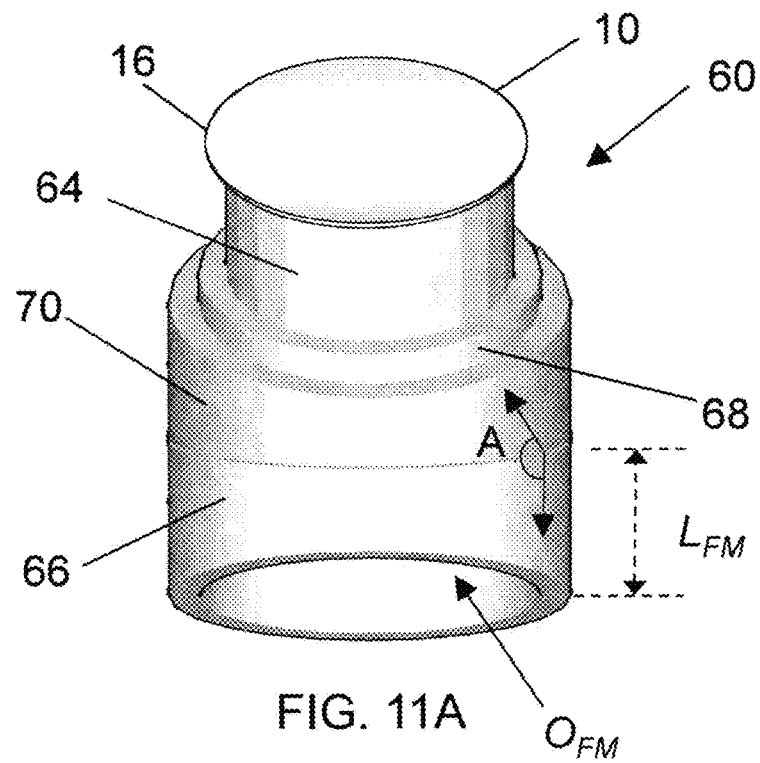
FIG. 11A is a top perspective view of the embodiment of the LNSCUP™ lens aid of the present invention of FIG. 10.
Figure 11B:
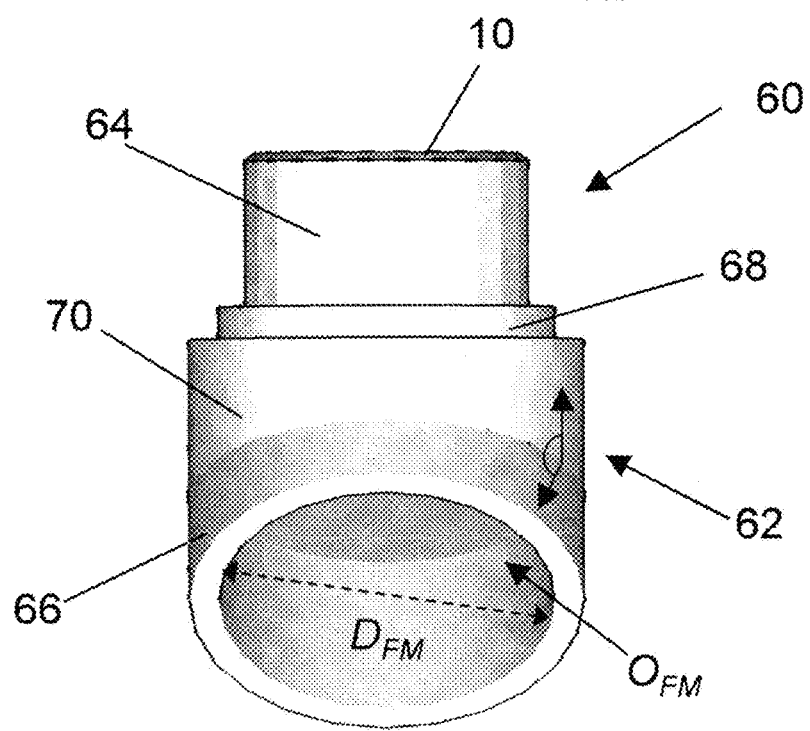
FIG. 11B is a bottom perspective view of the embodiment of the LNSCUP™ lens aid of the present invention of FIG. 10.
Figure 12:
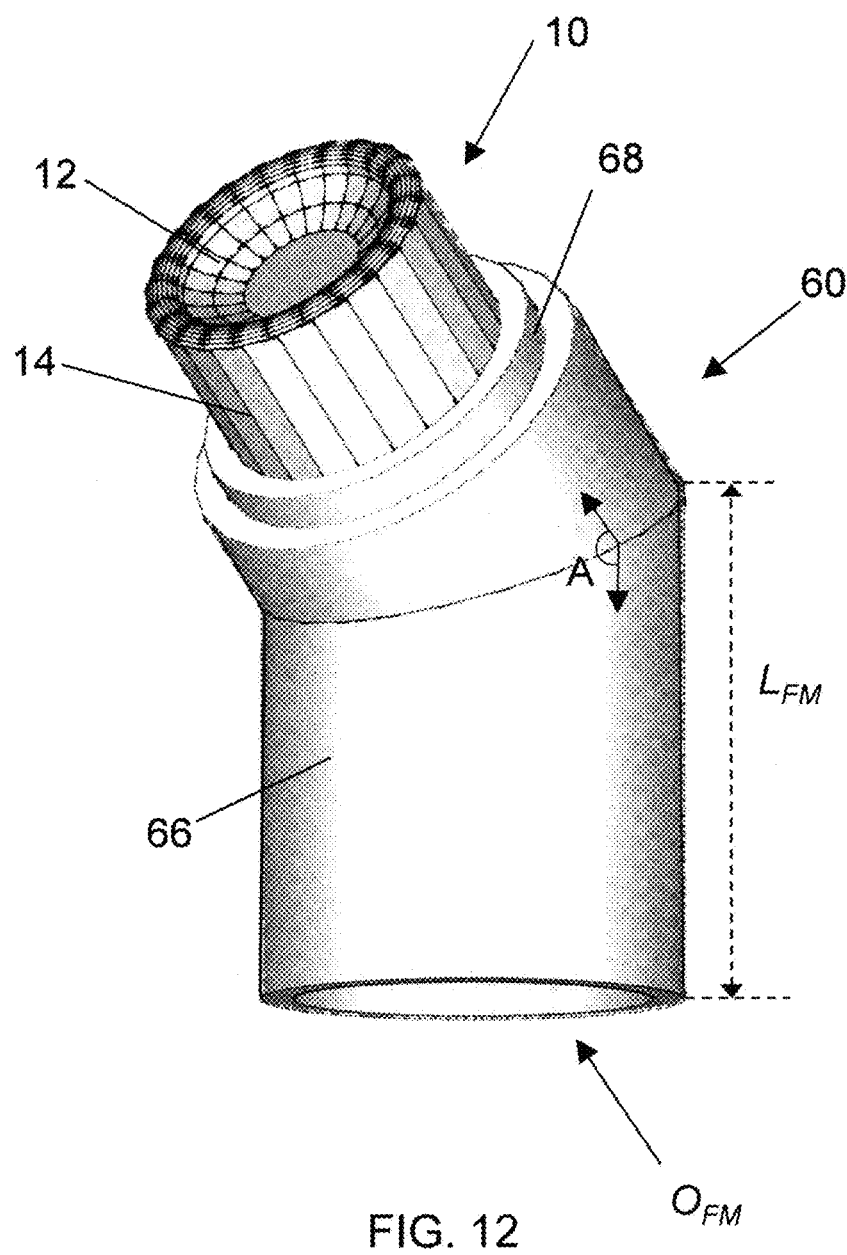
FIG. 12 is a perspective view of a further embodiment of the LNSCUP™ lens aid of the present invention having a lengthened finger-mount and an angular extension.
Figures 13A, 13B:
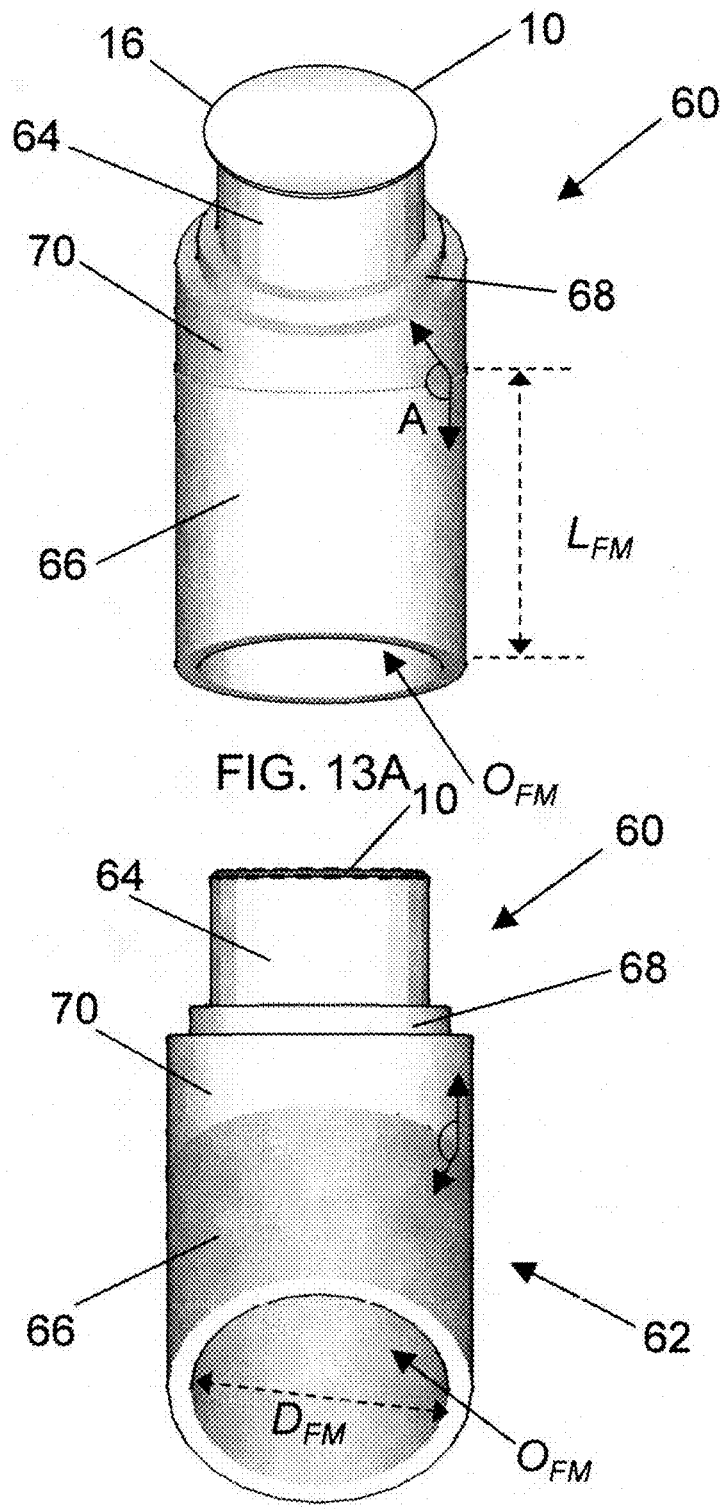
FIG. 13A is a top perspective view of the embodiment of the LNSCUP™ lens aid of the present invention of FIG. 12.
FIG. 13B is a bottom perspective view of the embodiment of the LNSCUP™ lens aid of the present invention of FIG. 12.

In a further embodiment, the LNSCUP™ lens aid 60 may have an angled podium 62 that provides for the lens cup 10 secured on the tubular support 64 to be directed toward the eye of the user and the opening $O_{FM}$ of the finger-mount 66 to be directed vertically, as shown in FIG. 10. An angular extension 70 is formed at an angle A in a range of between 120° and 150° and more preferably 135° to connect the transition portion 68 of the tubular support 64 to the finger-mount 66. In this way, the lens 16 is supported and is sufficiently secured on the soft pliable lens cup 10 at the angle A, as shown in FIG. 11A, and the user may simply hold their finger-tip vertically or at a gentle angle and preferably using a mirror, guide the lens 16 using LNSCUP™ lens aid 60 into their eye. The internal diameter $D_{FM}$ of the angled podium 62 as shown in FIG. 11B, may also be offered in different diameters to accommodate fingers of different sizes. The length $L_{FM}$ of the finger-mount 66 may also be of different sizes to accommodate different lengths of the tip of a user's finger. As shown in FIG. 12, in some embodiments, the finger-mount 66 may have an extended length $L_{FM}$ to accommodate a longer fingertip of some users and securely hold the LNSCUP™ lens aid 60 on the person's finger. With the angled podium 62 and finger-mount 66 held vertically or at a gentle angle with all fingers and hand out of view, the user may look forward or tilt their head slightly forward to align their eye more easily with the lens 16 and more easily insert the lens 16, as shown in FIG. 13A. The opening $O_{FM}$ of the angled podium 62 which may be of various diameters to accommodate different finger sizes is shown in FIG. 13B. The angled podium 62 of the LNSCUP™ lens aid 60 provides a unique pre-form bend feature to reduce the amount of dexterity needed and make it easier for a user to insert a lens 16.

Figure 14:
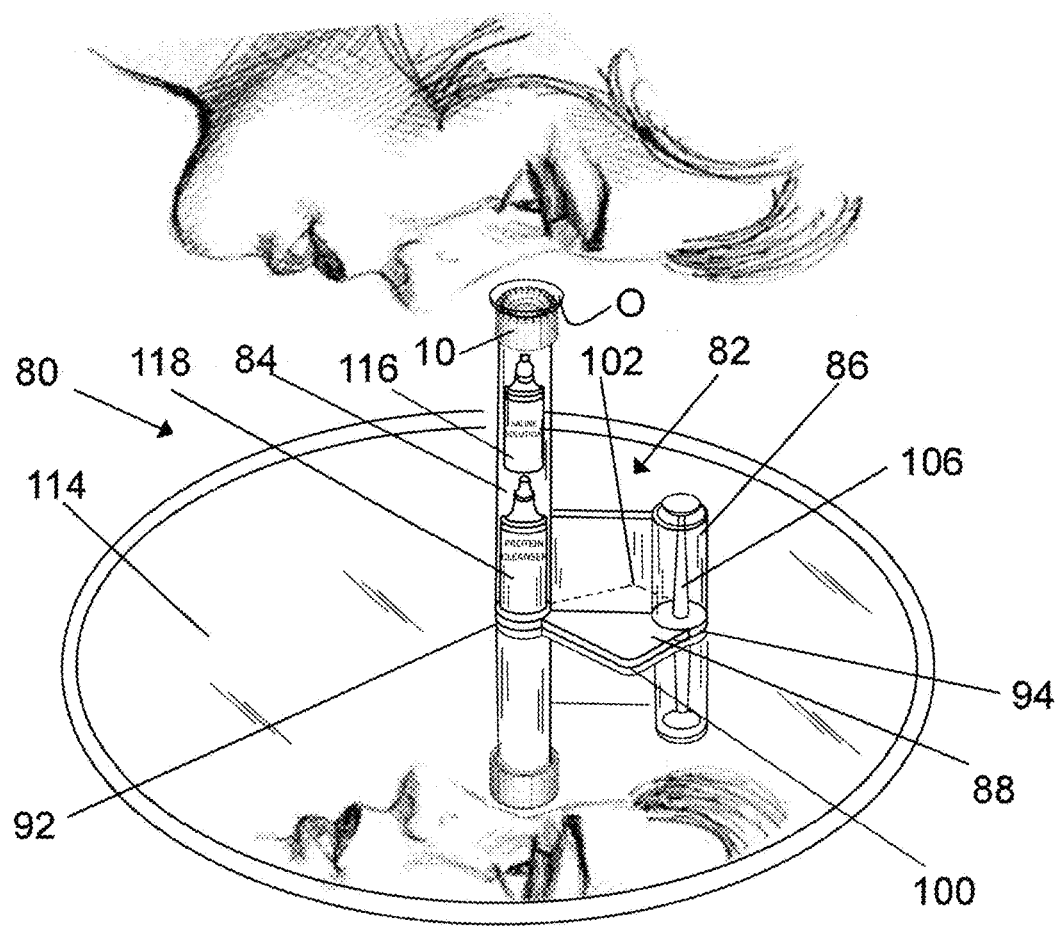
FIG. 14 is a perspective view of an embodiment of the LNSAID™ System or LNSLITE™ Kit that includes a mirror and showing the alignment of the eye with the lens supported on the lens cup that is supported on the lens cup podium of the present invention.

As shown in FIG. 14, the LNSAID™ System 80 provides for a lens 16 to be inserted into the eye in a hands-free manner which provides an insertion procedure that is much easier and requires less dexterity than the insertion procedures of the prior art. The LNSAID™ System 80 further provides the added advantage of a complete system or kit that has everything a user may need to both insert and remove a lens. The LNSAID™ System 80 comprises the lens cup 10 and a lens cup podium 82 having a support tube 84 and a storage tube 86 extending vertically from a platform 88. The support tube 84 and storage tube 86 provide for saline solution 116 and/or a protein cleaning solution 118 and a lens removal tool 106 to be portable within the LNSAID™ System 80 and be accessible to a user when needed. By using the reflection in a mirror 114, the user can look down along the support tube 84 by tilting their head forward to a horizontal position and then using both eyes and in particular the opposite eye than the one the lens 16 is being inserted into, guiding the eye onto the lens 16 situated on the lens cup 10.

In preparing for the insertion of the lens 16, the saline solution 116 and/or a protein cleaning solution 118 may remain inside of or be removed from the support tube 84 or storage tube 86. The lens cup 10 may be attached by sliding the body 14 of the lens cup 10 on to, around or preferably into the support tube 84. The lens cup 10 may be removably attached to the support tube 84 using a snap or frictional fit or other manner of fitting so that the lens cup 10 is stable and secure during the insertion process. The lens 16 to be inserted is positioned on top of the lens cup 10, then the lens cup 10 is filled with saline solution 116. The lens 16 is larger in diameter than the lens cup 10 creating the overhang O where the lens 16 extends beyond the lens cup 10. The lens 16 may be supported on the slightly raised smooth ridges 18 of the lens cup 10 to prevent possible slight suction from forming between the lens 16 and the lens cup 10 making it possibly a bit easier for the eyelids to grasp the lens 16. When inserting the lens 16, the user in a seated position leans forward to align their head using their neck muscles in a horizontal position thereby looking directly downward at the lens cup 10 and along the support tube 84 of the lens cup podium 82 which with the reflection in the mirror 114 provides a double full length view of the support tube 84 vertical axis allowing the user to more easily place their eye directly over the axis of the support tube 84 and align the lens 16 to their eye in preparation for insertion.

The LNSAID™ System 80 does not require the user to hold the lens cup podium 82 upright or only use one hand to maneuver the lens 16 with some possible difficulty to their eye as is common in the lens insertion procedures of the prior art. The user's hands are free to allow the user to use one or both hands to hold their eyelids open. Because scleral lenses are generally of larger diameters, it is very useful for a person to have two hands to get both eyelids very wide open and by using this method the user can firmly grasp the upper eyelid with one hand and the lower eyelid with a second hand and keep the eye from flinching to blink or close when inserting the lens 16. The user captures the lens 16 by surrounding the eyelids around the overhang O of the lens 16 on the lens cup 10. The soft flexible surface of the supporting lens cup 10 also provides a distinct advantage of allowing the lens 16 when pressed against the eye to slightly adjust its axis on and within the surface of the lens cup 10, and the adjustment made within the soft pliable material facilitates instant and exact and proper alignment of the lens 16 against the eye. Large misalignment or bubbles can cause blurriness and failure. The LNSAID™ System 80 reduces the risk of the failure of proper insertion with ideal informative viewing with no fingers in the way, and significantly improves the final exact axial alignment and positioning of the lens 16 onto the eye by the variably designed-in edge flexibility of the parabolic curves of the lens cup configuration. The LNSAID™ System 80 also removes the dexterity requirements of the one-handed prior art methods, by allowing the user to use both hands to open the eyelids very wide, reducing any risk of having an eyelash be captured under the lens while simultaneously providing a clear view in the mirror of the desired alignment.

Figure 15A:
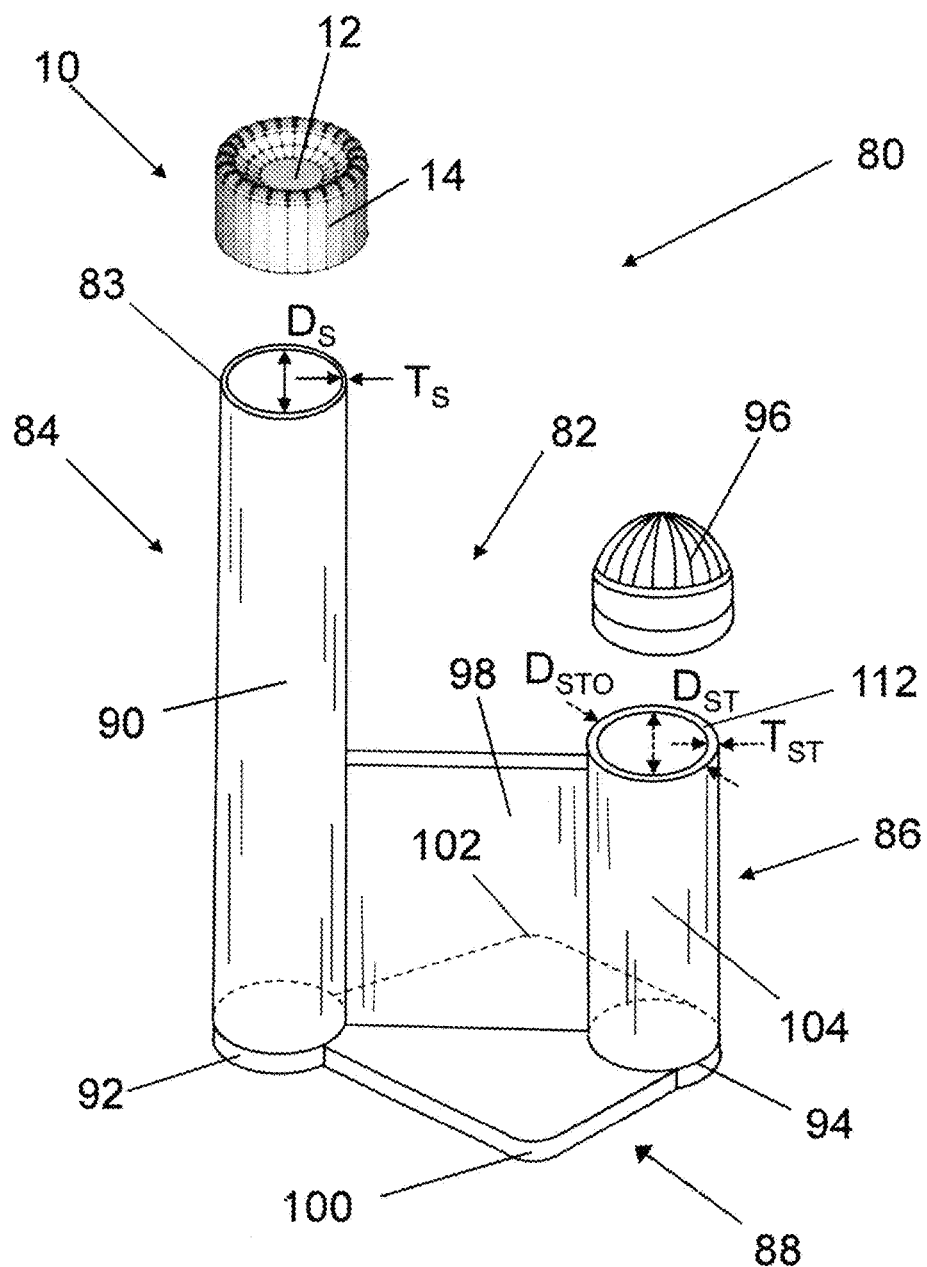
FIG. 15A is a perspective view indicating removable parts of an embodiment of the LNSAID™ System of the present invention.

The lens cup podium 82 of the LNSAID™ System 80 may be formed from a transparent material such as clear plastic to allow the user to see through the lens cup podium 82 to prevent any obstruction from the platform 88 and the support tube 84 when inserting the lens 16 into the eye and to be able to see the interior of the assembly for cleanliness and access to storage, and allow light to be directed up through it. The support tube 84 can be configured with the addition of a small hole in the base to allow for the user to view through the lens cup podium 82, down to a light source. In some embodiments, the LNSAID™ System 80 may be of an opaque, plastic of white or another color but preferably by using a clear material, the transmission of ambient light is obviously provided as an added benefit. A medical grade plastic and other medical grade materials may be chosen to produce the lens cup podium 82 of the LNSAID™ System 80. The lens cup podium 82 will be of an adequate weight and thickness, in embodiments as shown in FIG. 15A, a platform 88 of the lens cup podium 82 has rounded corners 92 and 94 under the support tube 84 and storage 86. The platform 88 extends out from the rounded corners 92 and 94 an adequate distance to provide sufficient mass and surface area in contact with the mirror 114 or top of a table to hold and maintain the lens cup podium 82 in a stable, upright position without requiring a user to hold the lens cup podium 82 upright with a hand. The opposing corners 100 and 102 extend out to form a somewhat diamond or square shaped base support in order to not obstruct very much of the view of 90 podium tube, and the user in using a mirror 114 and looking down the support tube 84 to align their eye with the lens 16. The weight and form of the platform 88 is to be sufficient so that a significant force would be required to tilt or tip the lens cup podium 82 meaning that the user could accidently bump or knock against the lens aid for example the support tube 84 and the lens cup podium 82 would not tip and the lens 16 within the lens cup 10 would not be dislodged. By having adequate weight and stability the user can free up both their hands to hold their upper and lower portions of the eyelid open when inserting the lens 16.

As shown in FIG. 15A, in some embodiments, the lens cup podium 82 may be molded as a single piece of plastic having a support tube 84 and a storage tube 86 that may be formed with and may be integrally formed or permanently affixed to a platform 88 where the material stiffness and pliability of its manufacture may vary according to the requirements of weight, dimensions and stability. The internal diameter $D_S$ of the support tube 84 and the thickness $T_S$ of the cylindrical sidewall 90 of the support tube 84 may be a fixed size to match a fixed size of the diameter $D_1$ and the thickness $T_1$ of channel C of the body 14 in certain embodiments of the lens cup 10. The fixed sizes of these dimensions of the body 14 and support tube 84 provide for the lens cup podium 82 to be used with lens cups 10 having different sized diameters for the upper surface portion 12 to accommodate different sized lenses 16. The lens cup 10 may be inserted preferably into, and also, on, or around the support tube or in preferred embodiments be temporarily fit, or permanently affixed to the support tube 84 using for example an adhesive or snap-in configuration.

Figure 15B:
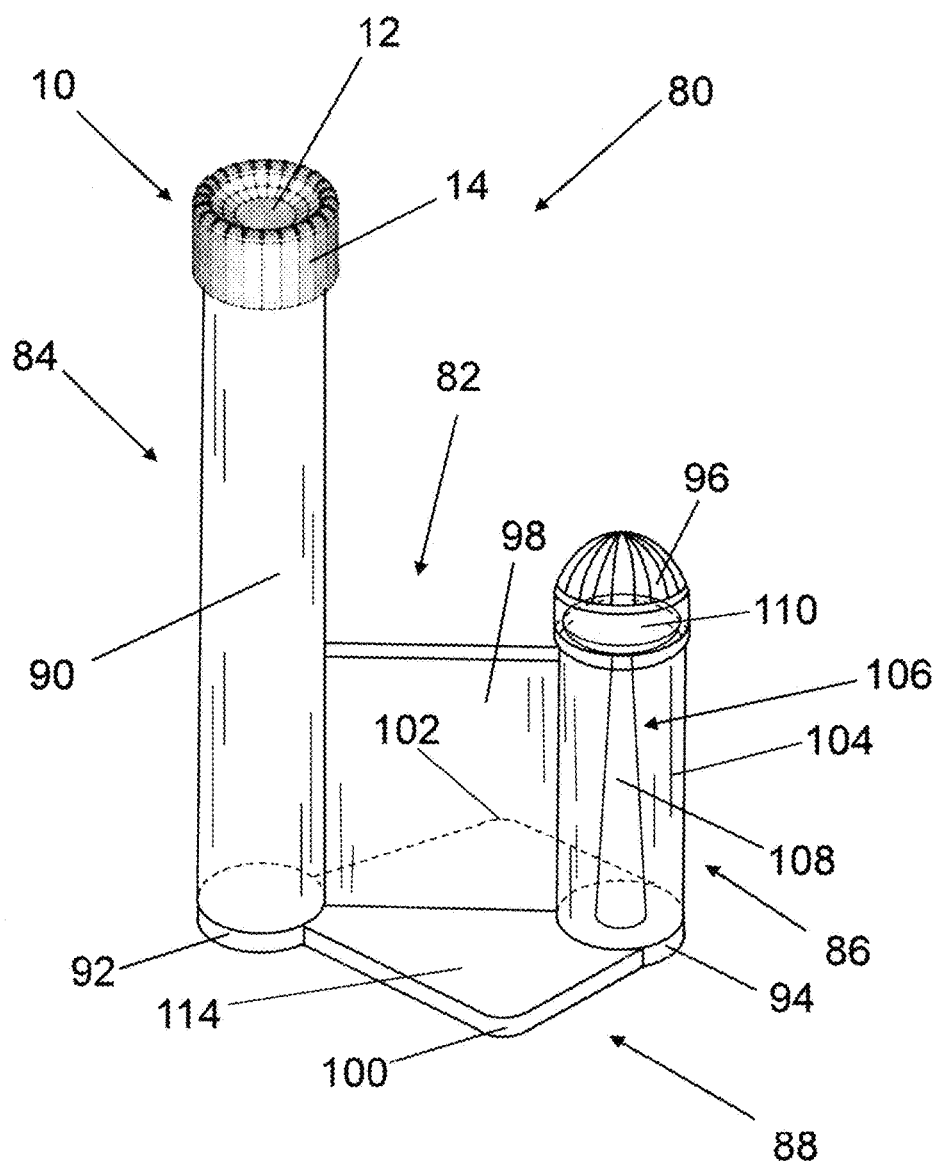
FIG. 15B is a perspective view of an embodiment of the LNSAID™ System of the present invention.

The storage tube or gripping tube 86 may extend from a rounded portion at the opposing corner 94 of the platform providing storage of items necessary to remove a lens 16, and a secure but easily removable storage cap 96 may be provided to seal the storage tube 86 to secure items. An important feature in some embodiments of the lens cup podium 82 of the LNSAID™ System 80 is having the storage tube 86 extend to a length from the platform 88 that is shorter than the length of the support tube 84. This provides for a clearance of the hand from the face should the user decide to use one hand to bring the entire LNSAID™ System 80 with the lens 16 sitting on the lens cup 10 up to the eye for insertion. In some embodiments, the diameter $D_{ST}$ and the thickness $T_{ST}$ of the cylindrical sidewall 104 of the storage tube 86 may be of the same dimension as the support tube 84. Although, the storage tube 86 may be of any adequate dimension to hold and secure items. One such item is a lens removal tool 106, as shown in FIG. 15B. In a preferred embodiment, the length of the storage tube 86 is less that the length of the shaft 108 of the lens removal tube 106 which provides for the cup 110 of the lens removal tool 106 to extend above the rim 112 of the storage tube 86 preventing the cup 110 from sticking to the cylindrical wall 104 of the storage tube 86 due to moisture from a cleaning solution, for example. Thus, the lens removal tool 106, may be easily grasped and pulled out of the storage tube 86 while not soiling the cup by the fingers, a desirable feature. In a preferred embodiment, the inside diameter $D_{ST}$ of the storage tube 86 is the same diameter to the cap of the lens removal tool 106 and is configured to fit flush outside and slide inside the storage tube to secure it in position. In other configurations, the cap 96 may be the smaller or larger than the outside diameter $D_{STO}$ of the storage tube 86.

A stabilizer brace 98 may extend between the support tube 84 and storage tube 86 to give added stability to the System 80. The stabilizer brace 98 may have two walls with an airspace between connected at the top with a LNSAID logo embossed on top. This stabilizing brace further provides a position for the user to easily grip by as little as two fingers and lift the LNSAID™ System 80 up for lens insertion or to carry or hold the lens cup podium 82 when installing or removing a lens cup 10 or the storage cap 96 from the storage tube 86. The lens cup 10 is removable so that it may be cleaned or in some embodiments, due to a different life cycle be disposable so that it may be replaced after each or a certain number of insertions or after a certain period of time as needed.

A top view of an embodiment of the lens cup in shown in FIG. 16A and a top view of the storage cap is shown in FIG. 16B. While in some embodiments, the storage tube cap 96 may preferably have a small flat portion on top of the cap 96 with a rounded surface below, so that it may rest vertically on a surface upside down. The rounded upper surface 120 and a stepped cylindrical mid-portion provides for the storage cap 96 to extend down inside into, and be flush with the surround of the storage tube 86 below, and enclose for example the lens removal tool 106. The cap 96 is to be of adequate dimension to extend into, and be flush on the outside of the storage tube 86 and may be snap fitted, screw fitted, frictionally fitted or otherwise removably attached to the storage tube 86.

In some embodiments, the LNSAID™ System 80 comprises a lens cup 10 and lens cup support stand or podium 82 having a support tube 84 and storage tube 86 that are permanently affixed to the platform 88. In other embodiments, the support tube 84 and storage tube 86 are removably attached and may be attached to the platform 88 using a rimmed connector 136 that provides for the tubes 84 and 86 to be inserted through, snapped into, slid around, be glued, heat welded or otherwise secured to the platform 88, as shown in FIG. 16C. The rimmed connectors 136 may be formed with the platform 88 through, for example, a plastic molding process and may provide a closure to the bottom of the tubes 84 and 86. Alternatively, the support tube 84 and storage tube 86 may be closed on one end and be connected to the platform 88 by inserting the end 138 of each tube through openings in the platform 88 to form a frictional fit and secure the support tube 84 and the storage tube 86 to the platform 88. The length Ls of the support tube 84 is between 5.08 cm (2 in) to 15.24 cm (6 in) and more preferably around 7.62 cm (3 in). The length $L_{ST}$ of the storage tube is between 2.54 cm (1 in) to 7.62 cm (3 in) and more preferably around 5.08 cm (2 in).

While the platform 88 may be in any shape, such as square, triangular, oval, circular, a four-sided square-like shape is preferred, with edges 148 that extend from the rounded corner 92 under the support tube 84 at an angle θ of 90° or less to enhance the view by the user along the vertical axis of the support tube 84, as shown in a top view of the platform 88 in FIG. 16D. By having the platform 88 in a four-sided square or in other embodiments, the podium tube 84 is connected at a corner, so that the podium tube and its flush base provide for a clear viewing angle around the platform 88 while looking down and the platform 88 does not obstruct very much of the view of the user in using a mirror 114 and looking down the support tube 84 to align their eye with the lens 16 supported on the lens cup 10. The platform 88 is of a heavy enough material and the two other opposing corners 100 and 102 extend a sufficient distance to provide proper support to hold the support tube 84 steady while the lens 16 is being inserted into the eye without the requirement that the lens cup podium 82 be held by the user's hand.

Figure 17A:
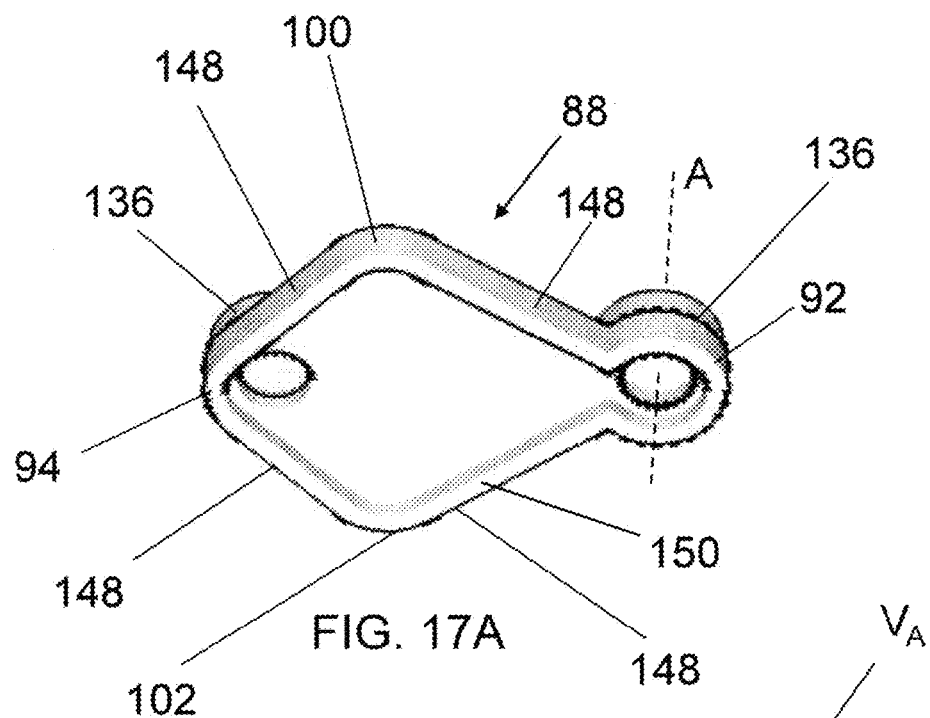
FIG. 17A is a bottom perspective view of an embodiment of the platform of the lens cup podium in an embodiment of the LNSAID™ System of the present invention.
Figure 17B:
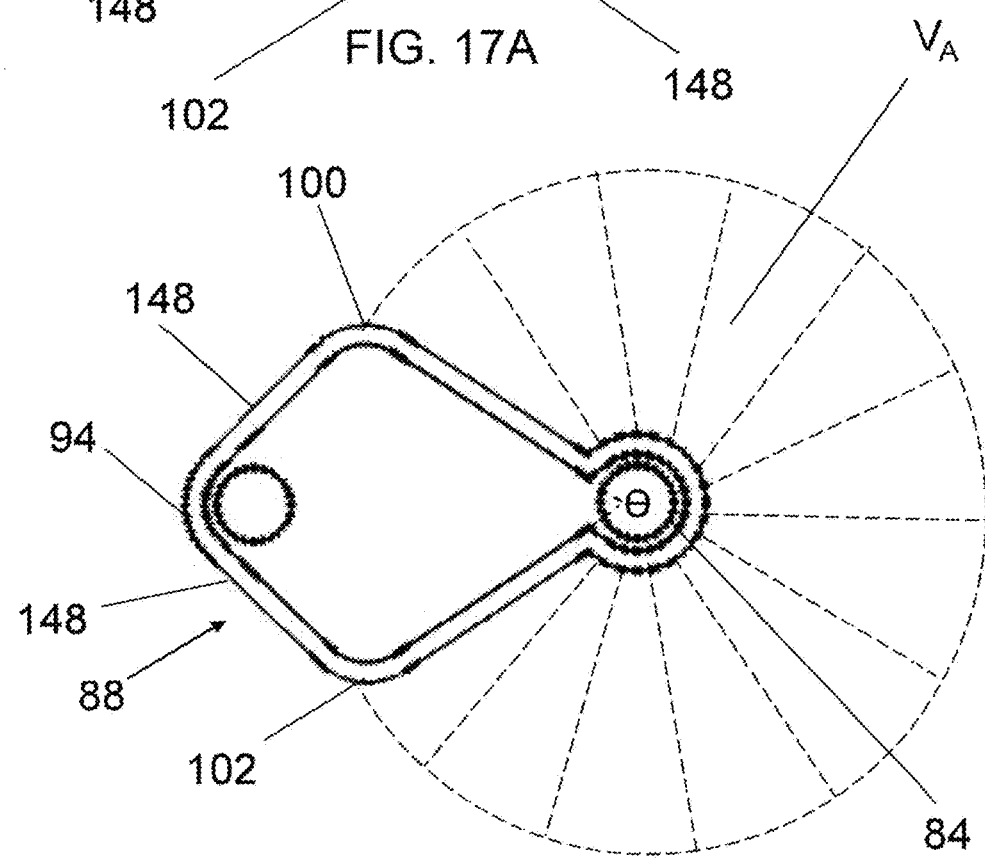
FIG. 17B is a bottom view of an embodiment of the platform of the lens cup podium in an embodiment of the LNSAID™ System of the present invention.
Figure 18A:
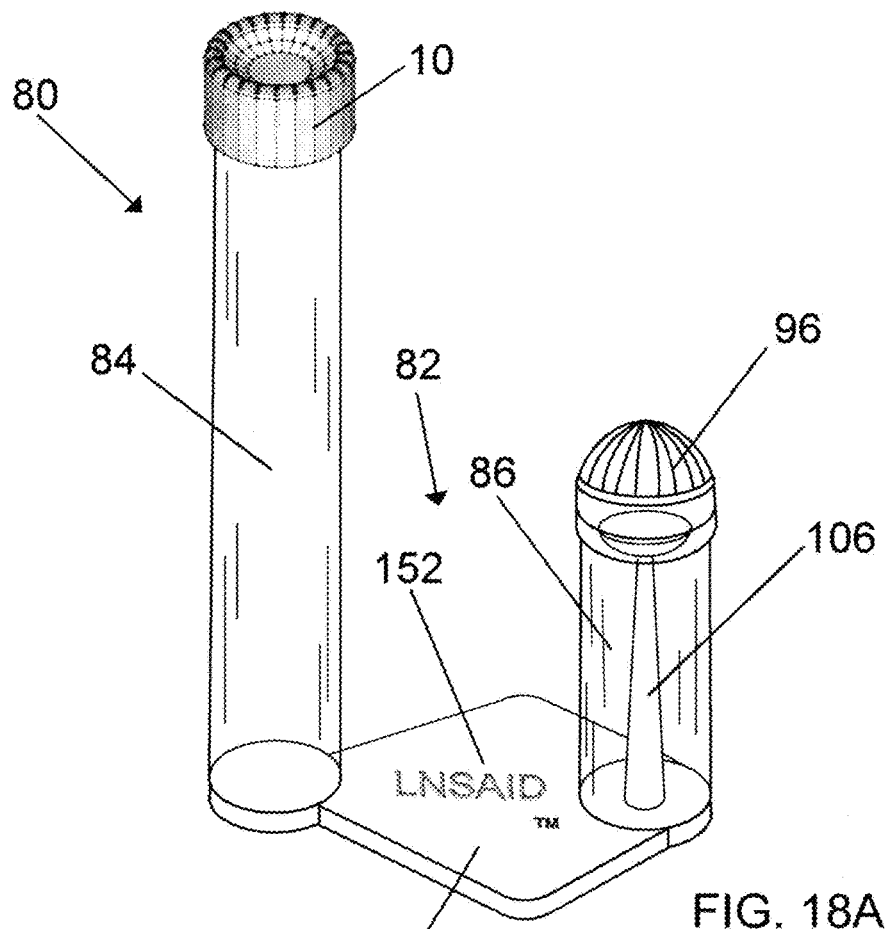
FIG. 18A is a perspective view of a further embodiment of the LNSAID™ System of the present invention.
Figure 18B:
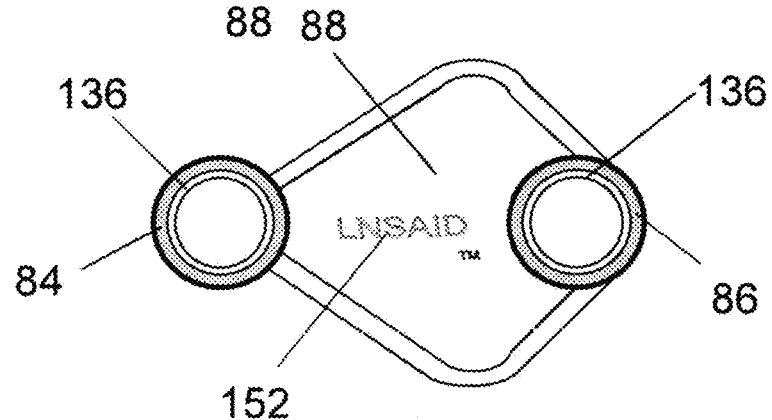
FIG. 18B is a top view of the further embodiment of the LNSAID™ System of FIG. 18A.

The bottom of the platform 88, as shown in FIGS. 17A and 17B, may be formed with an accurately flat made outer rim 150 to align the platform 88 evenly on a flat surface and prevent any tendency for it to rock or tip. The outer rim 150 also prevents scratches or damage to the surface of a mirror 114 or table top. As shown in FIG. 17B, in preferred embodiments the support tube 84 is narrow in structure or may in some embodiments be a rod instead of a tube and is affixed to a rounded corner 92 of the platform 88 with each edge 148 extending from the rounded corner 92 at 90° or an angle θ that is less than 90° providing a clear viewing area $V_A$ around the support tube 84 and down to the mirror revealing the desired axis A, as shown in FIG. 17A, that extends vertically from the platform through the center of the support tube 84 to align the lens 16 within the eye. The lens cup podium 82 of the LNSAID™ System 80 may have indicia 152 such as the name LNSAID™ for the system as shown in a perspective view in FIG. 18A and in a top view of the LNSAID™ System 80 in FIG. 18B. In some embodiments, the LNSAID™ System 80 may have only the support tube 84 and storage tube 86 attached to the platform 88 without a stabilizer brace 98, the platform 88 being of adequate weight and stability of construction maintain the support tube 84 in an upright position without the necessity of a user holding the lens cup podium 82 when inserting a lens 16 into their eye.

Figure 19:
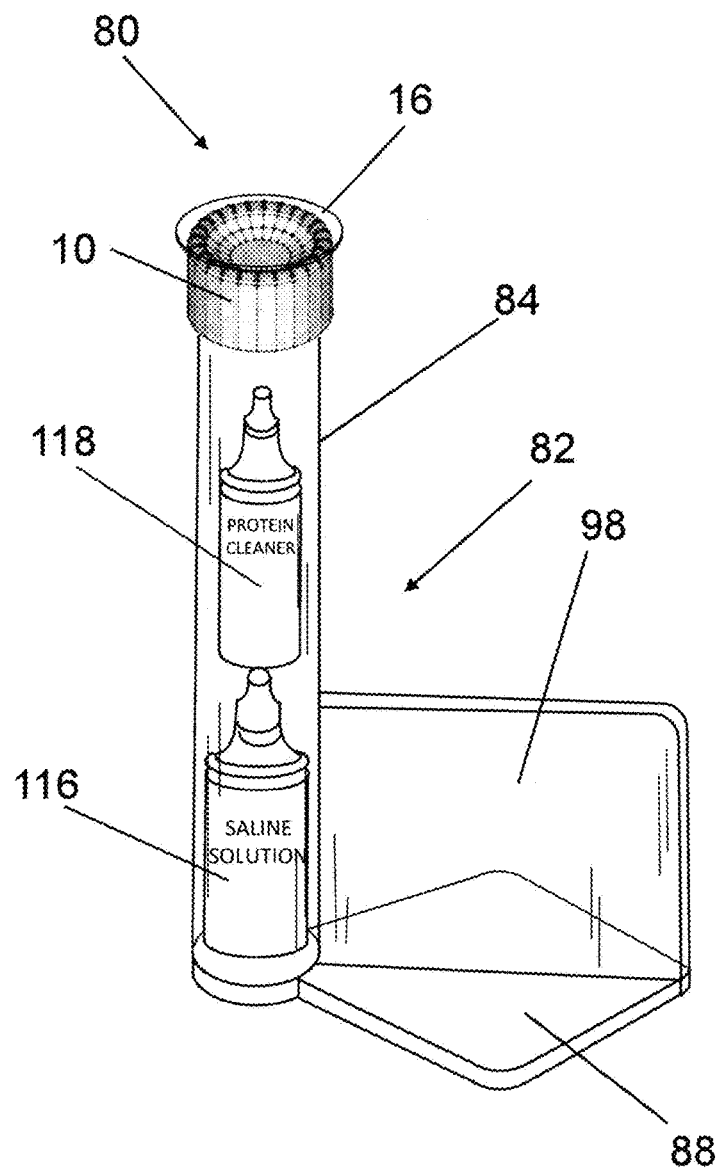
FIG. 19 is a perspective view of a still further embodiment of the LNSAID™ System of the present invention.
Figure 20:
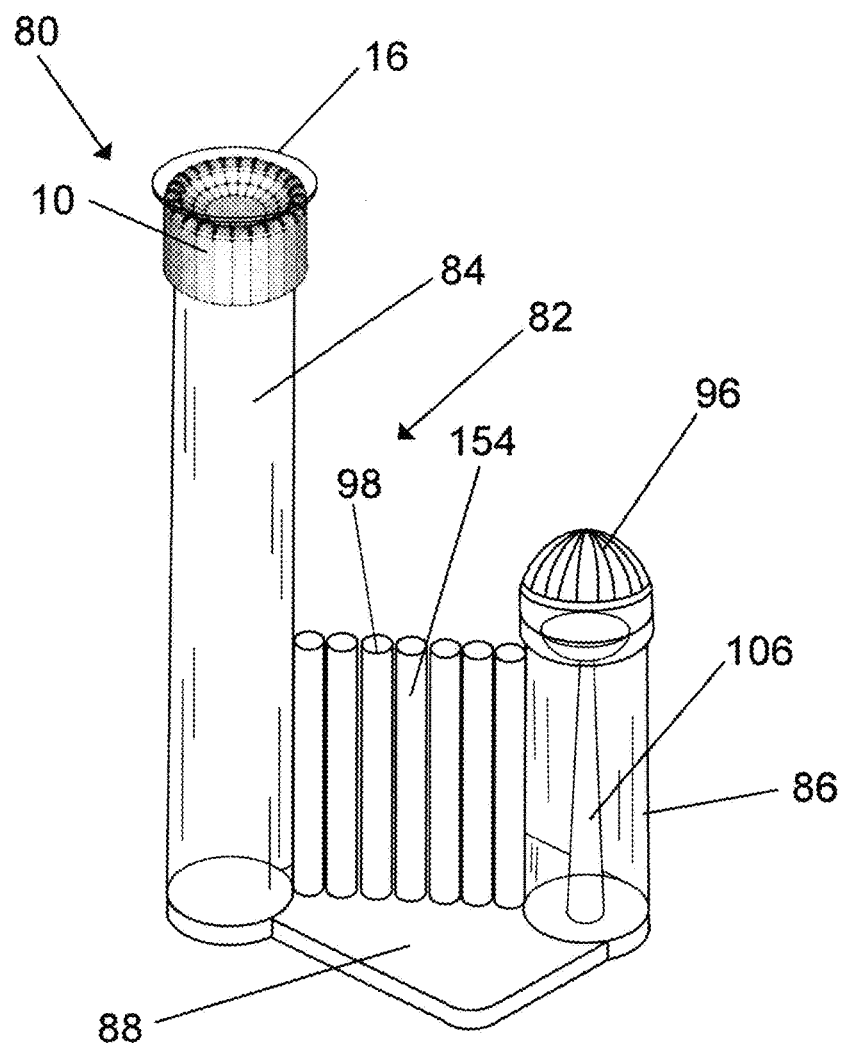
FIG. 20 is a perspective view of a still further embodiment of the LNSAID™ System of the present invention.
Figure 21:
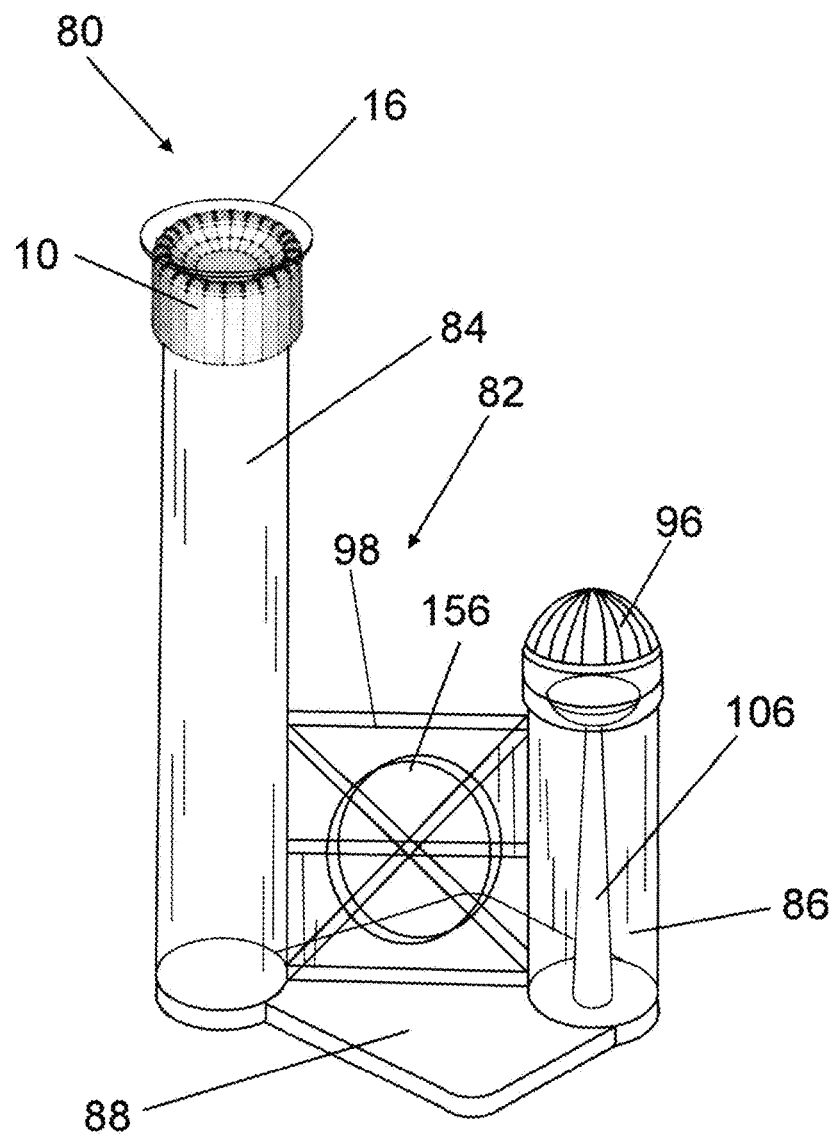
FIG. 21 is a perspective view of a still further embodiment of the LNSAID™ System of the present invention.
Figure 22A:
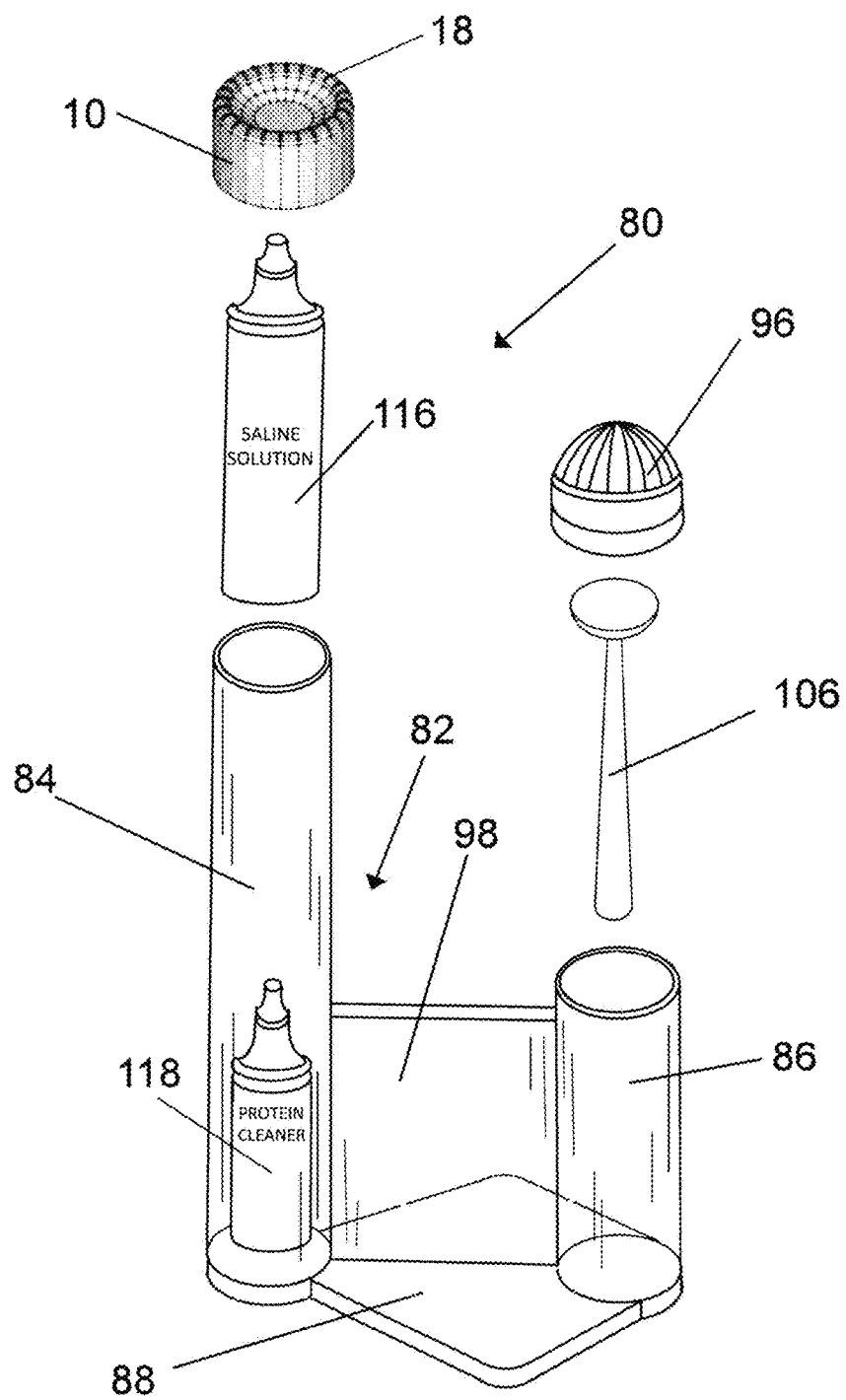
FIG. 22A is an exploded view of the LNSAID™ System of the present invention as a kit.
Figure 22B:
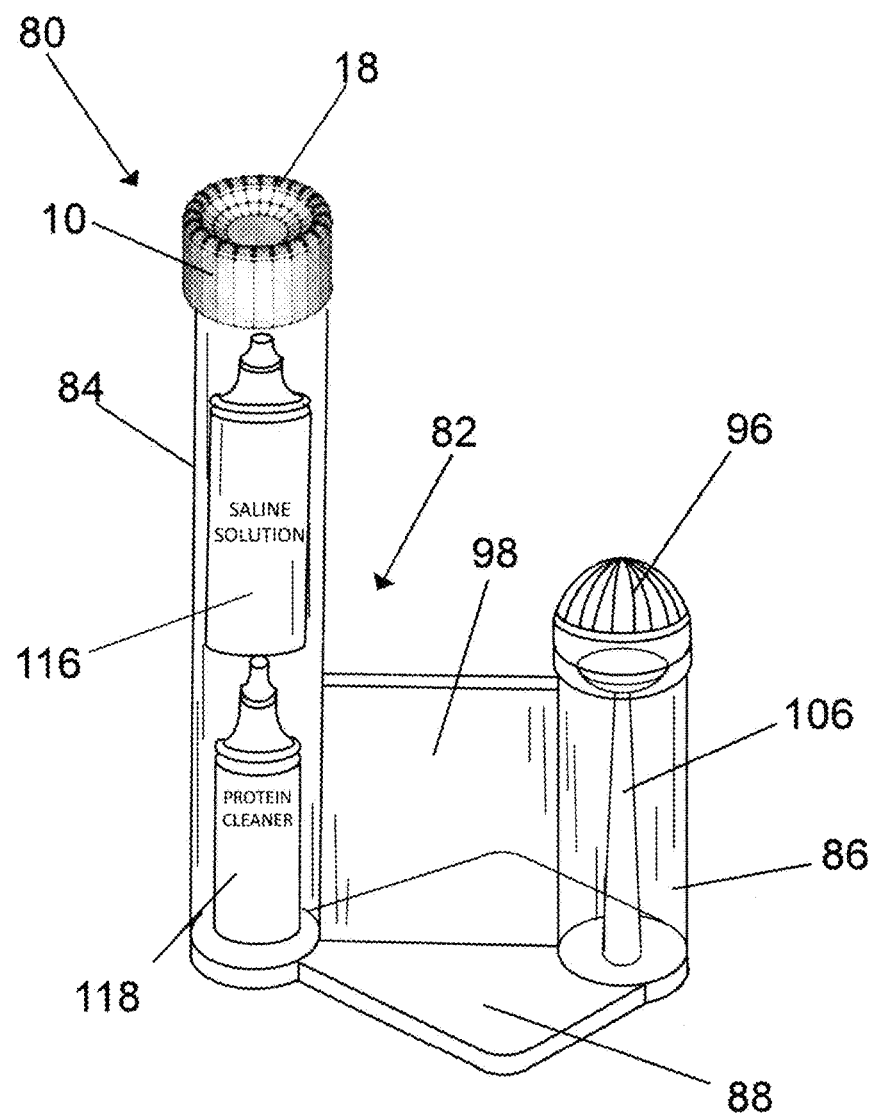
FIG. 22B is a perspective view of the LNSAID™ System of the present invention as a kit.

In further embodiments, the lens cup podium 82 of the LNSAID™ System 80 may have only a support tube 84 for the lens cup 10 and items such as saline solution 116 or protein cleaner 118 or other items may be stored within the support tube 84 as shown in FIG. 19. The LNSAID™ System 80 may have a stabilizer brace 98 to provide a handle and structural support to provide for the lens cup podium 82 to further stabilize the support tube 84 in an upright position, so that a user may insert the lens 16 within their eye without having to hold the lens cup podium 82 leaving both of their hands free to hold their eyelid open. In other embodiments, the stabilizer brace 98, as shown in FIGS. 20 and 21, may be of various designs to provide a tactile surface 154 for the user to easily grasp or include a decorative element 156, or other configurations to adequately and structurally support the lens cup podium 82 of the LNSAID™ System 80 in an upright position so that a user may insert a lens 16 into their eye without having to hold the lens cup podium 82. As shown in FIGS. 22A and 22B, the LNSAID™ System 80 provides a complete kit to have everything accessible for a user to insert and remove a lens from their eye. The LNSAID™ System 80 kit may include the lens cup 10, the lens cup podium 82, saline solution 116, protein cleanser 118, and a cap 96 to close the storage tube 86.

Figure 23:
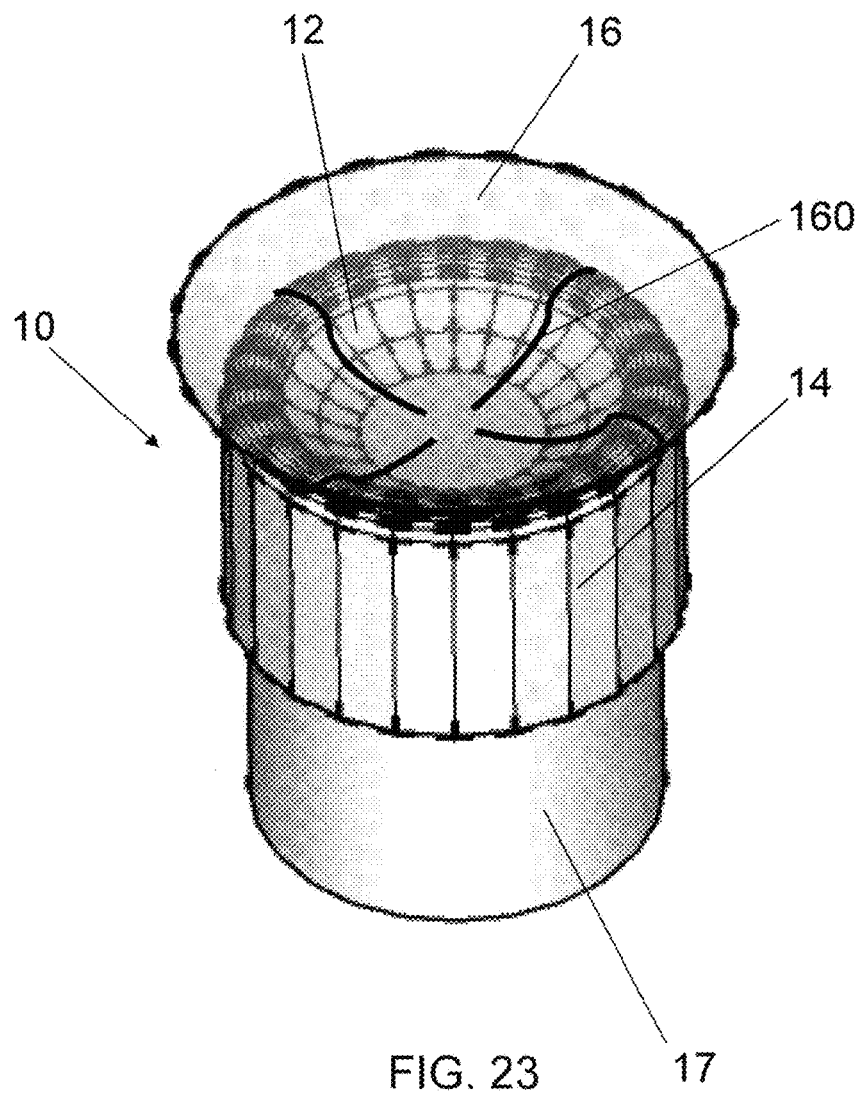
FIG. 23 is a top perspective view of a lens cup of the present invention having an orientation indicator useful for lens insertions that are not symmetrically round.
Figures 24A, 24B, 24C:
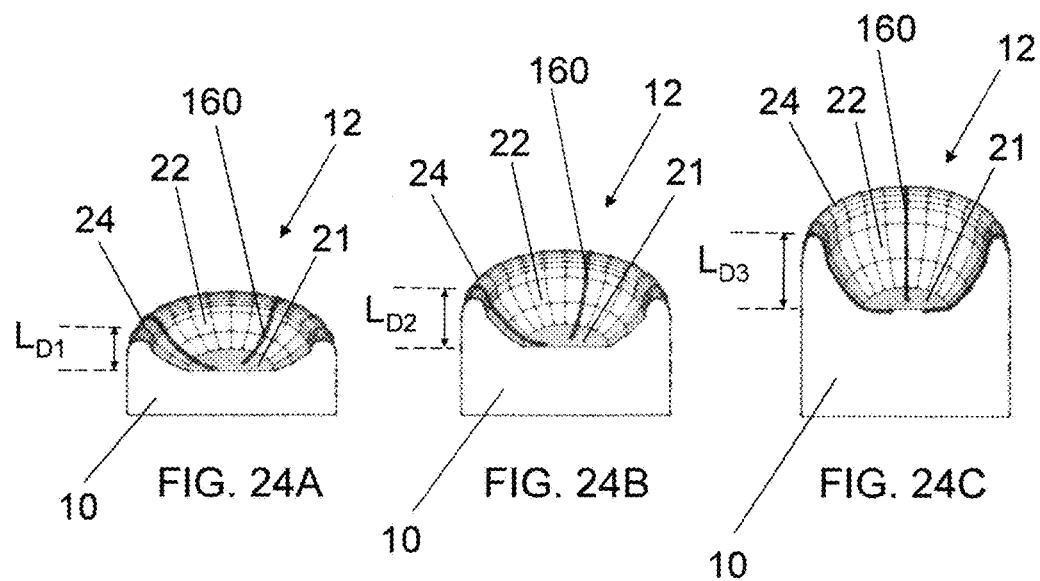
FIGS. 24A, 24B, and 24C are cross-sectional views of an orientation indicator on the lens cup to assist in properly positioning the eye over the lens where lenses are prescribed of different depths.
Figure 25:
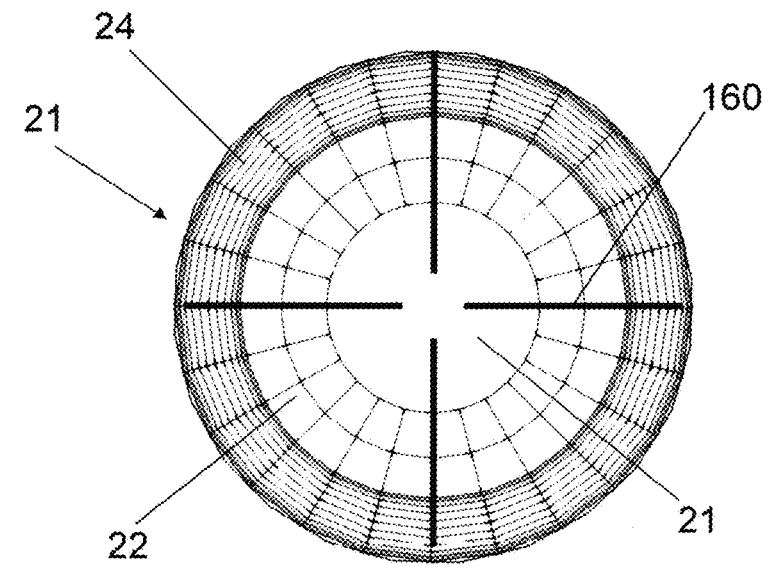
FIG. 25 is a top view of an embodiment of the lens cup with an orientation indicator.

In some embodiments of the lens cup 10, an extended base 17 is provided to insert the base 17 into the support tube 84 as described herein. The lens cup 10 in some embodiments may also be provided with an orientation indicator 160 such as using lines or dots drawn on or along the curvature of the lens cup 10 to assist the user in aligning the lens 16 with their eye as shown in FIG. 23. As shown in FIGS. 24A-24C, if the eye is not in proper alignment with the lens 16, the orientation indicator 160 appears as curved lines that provide for the user to identify the proper direction to move towards. If the orientation indicator 160 appears as curved lines that are off-center to one side, the user moves in the direction where the orientation indicator 160 will appear to be less curved. As the user moves further the orientation indicator 160 appears to be straighter and straighter lines and when the lines appear straight and perpendicular, as when viewed from directly above as shown in FIG. 25, the eye is properly aligned over the lens cup 10 and lens 16. A dot or two dots may be added on the top edge of one line to indicate left and right eye axis of orientation for insertion. The lens cup 10 may also be of different depths and curvatures to accommodate lenses 16 of different sizes and shapes as described herein. As shown in FIG. 24A, the length $L_{D1}$ from the center portion 21 to the rim 24 of the lens cup 10 may be of a shorter distance with a shallow curvature along the mid-portion 22. In another embodiment as shown in FIG. 24B, the length $L_{D2}$ from the center portion 21 to the rim 24 may be increased with a less shallow curvature along the mid-portion. In other embodiments as shown in FIG. 24C, the length $L_{D3}$ from the center portion 21 to the rim 24 may be substantially increased with a sharp transition along the mid-portion 22 creating a greater curvature and depth and preferably with all curvatures of a parabolic curve form within the upper surface 12 of the lens cup 10. Because lenses and particularly larger scleral lenses come in various sizes, curvatures and diameters, the embodiments of the lens cup 10 of the present invention will likely come in various depths and curvatures to provide for the proper lens cup 10 to be selected for any particular lens 16. The upper surface 12 of the lens cup 10 is formed very differently from the inclined or conically tapered cup or bowl shaped insertion tools of the prior art. The variably sized parabolic shaped lens cups provide a greater range of rigidity and flexibility where it is needed, and have stable thicker foundations in the central area of the upper surface 12 to hold the lens 16 level. More specifically, the mid-portion walls 22 are not straight, circular, convex or conical in shape but instead are formed as parabolic curves of various curvatures that extend increasingly out and upwards from the center portion 21 where a thin membrane or small or larger hole may be located to allow light to be seen by the person doing the insertion. The transition along the curved mid-portion walls 22 to the soft, pliable rim 24 provides the more appropriate variable stiffness desired with the foundation being stiff and the curved mid-portion walls 22 being increasingly more flexible as they approach the outer rim 24 of the lens cup 10. The rim 24 therefore will be more readily flexible and at the critical point of contact of the eye to the lens, more appropriately flex instantly so that as the eye imperfectly touches an edge of the lens 16, the rim 24 of the lens cup 10 compresses to specifically accommodate the minute adjustment needed in the positioning of the lens 16 to quickly seat the lens 16 uniformly within the eye, for the eyelids to close around and capture the lens 16 for rapid and successful insertion. This is a critically important feature that greatly assists in the process of properly inserting a large diameter scleral lens into the human eye.

Figure 26A:
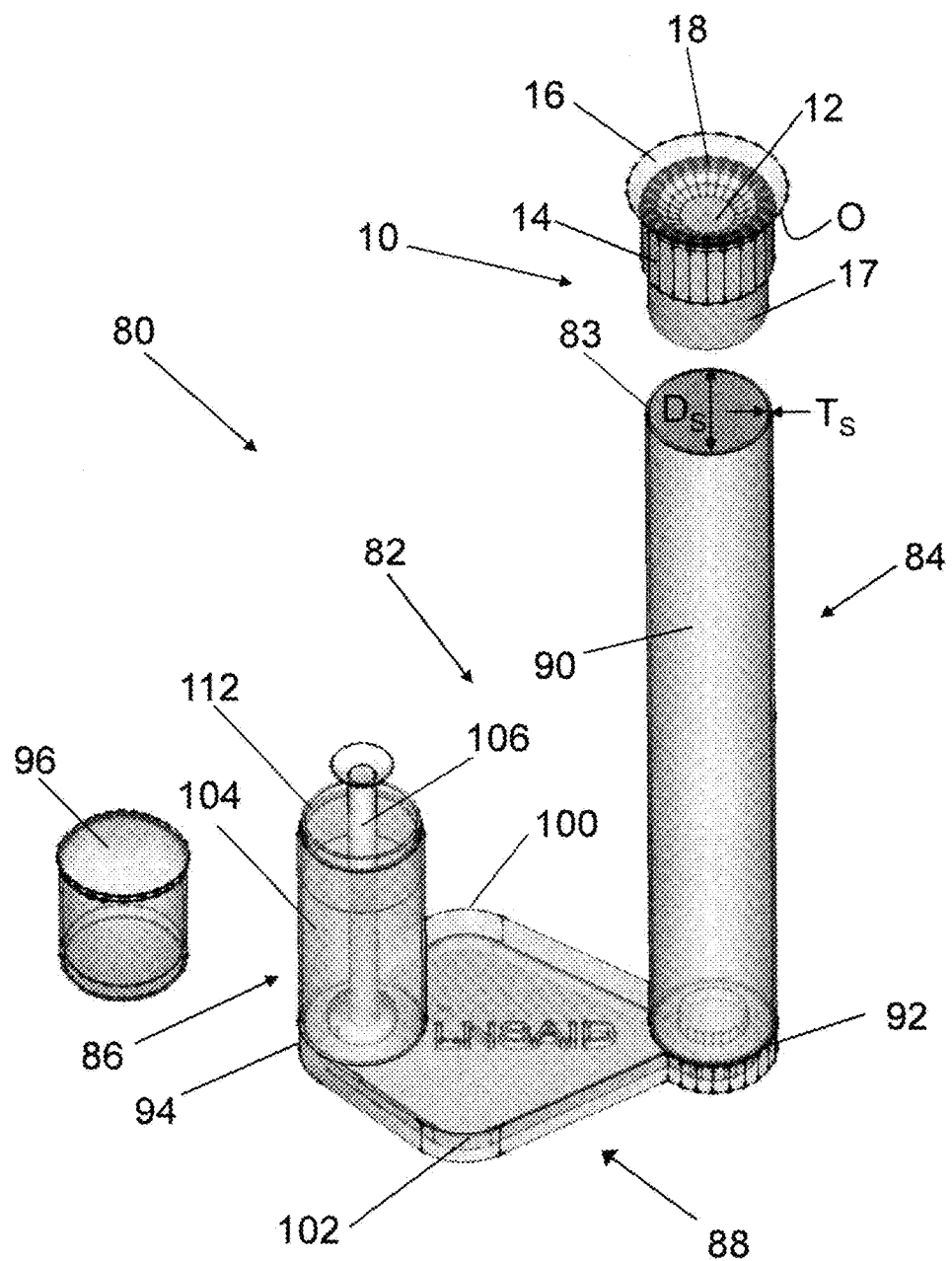
FIG. 26A is an exploded perspective view of another embodiment of the LNSAID™ System of the present invention with a lens removal tool.
Figure 26B:
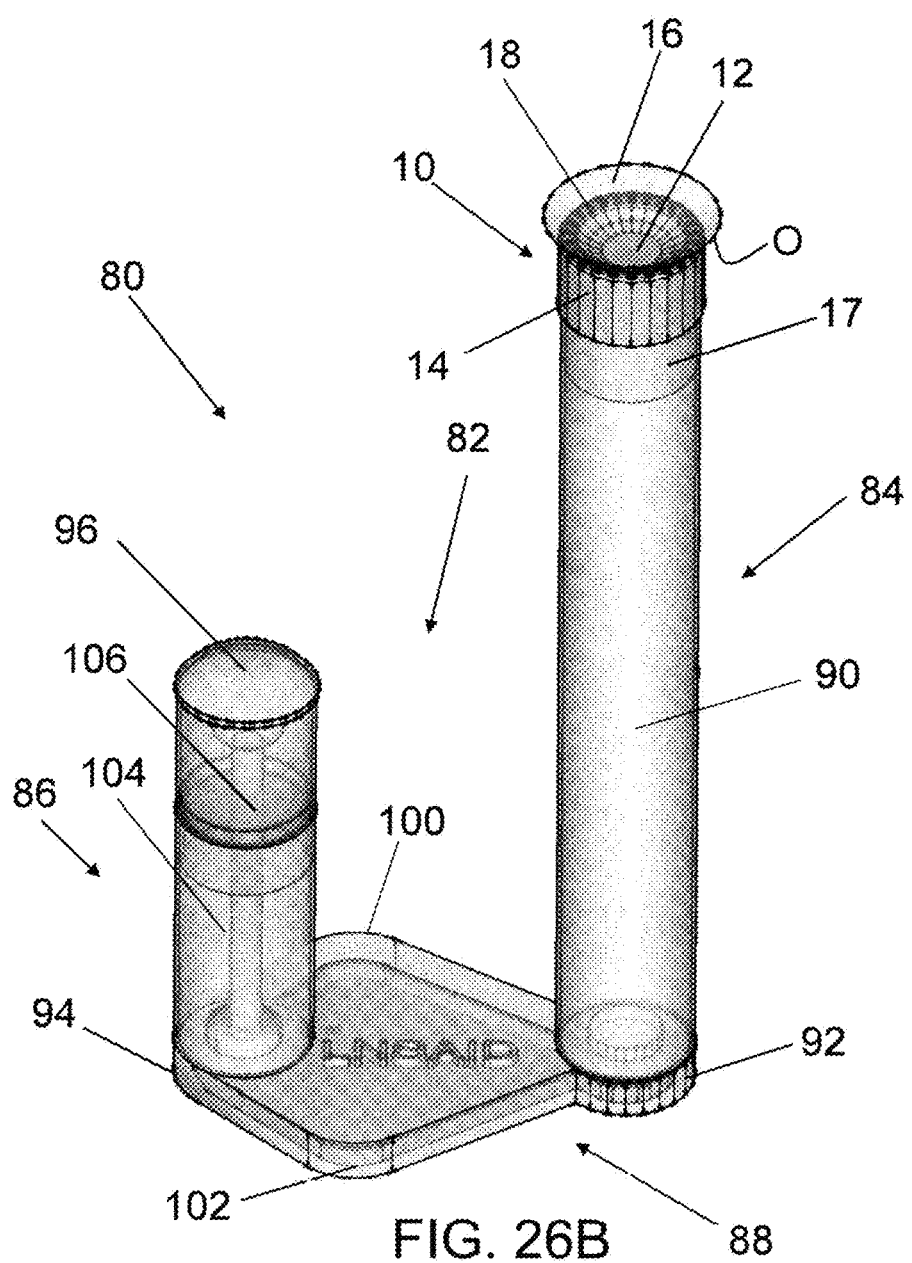
FIG. 26B is a perspective view of the LNSAID™ System of the present invention with a lens removal tool of FIG. 26A.
Figure 27B:
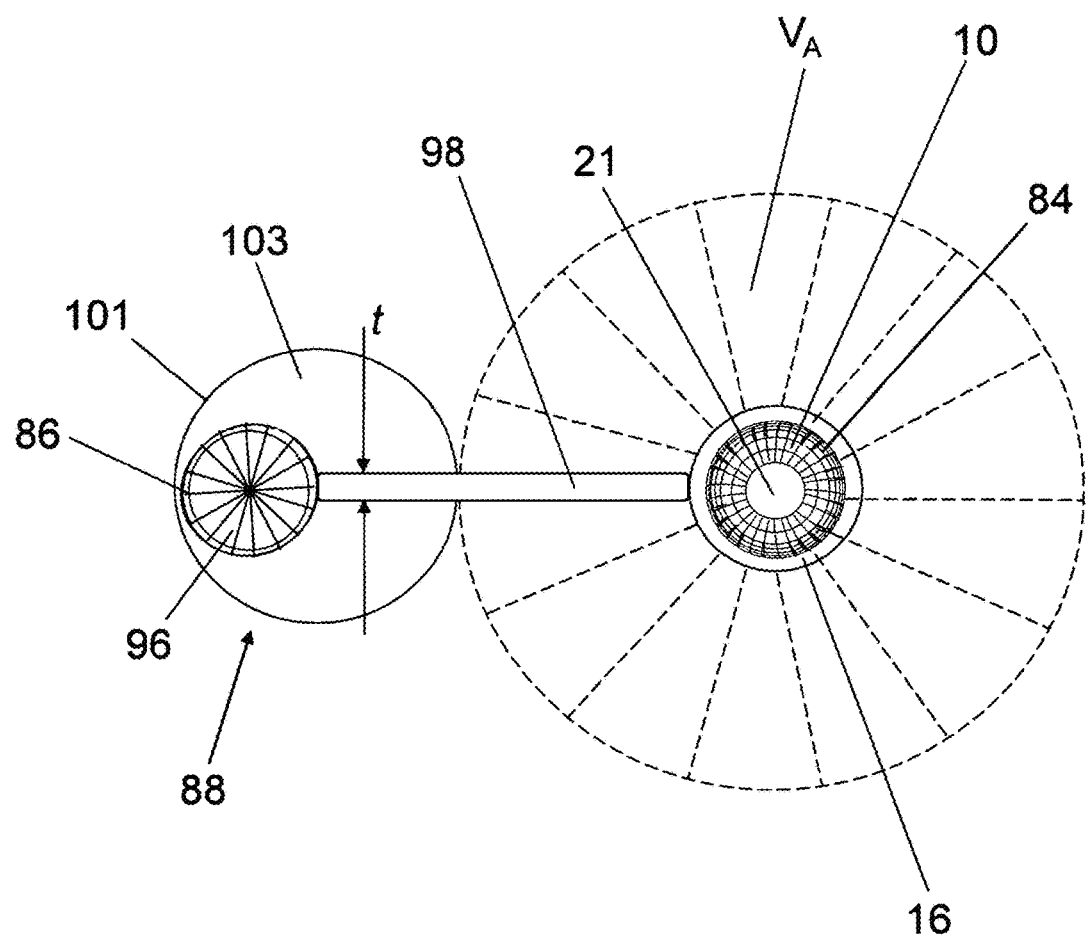
FIG. 27B is a bottom view of an embodiment of the platform of the lens cup podium in the further embodiment of the LNSAID™ System of FIG. 27A.

As shown in FIG. 26A, the extended base 17 of the lens cup 10 is of a diameter $D_3$ that is only slightly less than the inside diameter $D_S$ of the support tube 84. The body 14 of the lens cup 10 may have a diameter $D_2$ that is larger than the diameter $D_S$ of the support tube 84 to provide for the body 14 to rest on the rim 83 of the support tube 84 and prevent the lens cup 10 being inserted completely into the support tube 84. The lens cup 10 may be securely affixed to the support tube 84 using a tight frictional fit. The body 14 provides a region for the user to grip and easily pull on and remove the lens cup 10 from the support tube 84 for cleaning or replacement. As shown in FIG. 26B, when inserted the supple material, structural shape, and overall design of the lens cup 10 provides a unique and reliable method of inserting and adjusting a lens 16 for proper alignment within the eye. In further embodiments of the present invention as shown in FIG. 27A, the storage tube 86 may extend from a platform 88 that is circular in shape. In embodiments of the platform 88 having a smooth circular edge 101 and flat upper surface 103 and being of sufficient weight, diameter and thickness to hold the lens cup podium 82 stable. A stabilizer brace 98 extends from the storage tube 86 and is affixed to the support tube 84 that may have a circular base 105 of the same or a smaller diameter as the support tube 84. In FIG. 27B, by having the support tube 84 be held vertically using the stabilizer brace 98 and be supported on the base 103 of a similar or smaller diameter a clear viewing area $V_A$ is provided for a user to view along the support tube 84 and down to the mirror 114 revealing the desired double length axis along the centerline of the support tube 84, to align the lens 16 within the eye. The viewing area $V_A$ is just short of 360° with only the thickness t of the stabilizer brace 98 interrupting the view, when viewed from the top, blocking the view to the mirror 114. The stabilizer brace 98 may therefore be of any adequate thickness to hold the support tube 84 in a vertical position and provide as desired by the user a hands-free method of inserting the lens 16 with the least interrupted view. In some embodiments, the lens cup 10 may have a hole to a light source below or a thin membrane that can glow from the light coming from below at the central portion 21 to also assist a user with the exact alignment of the eye on the lens 16. The sturdy and stable platform 88 and in some embodiments the stabilizer brace 98 maintains the support tube 84 of the lens cup podium 82 in an upright extended position requiring substantial force to tip or dislodge the lens 16 from the lens cup 10 so that a user may much more easily than methods of the prior art, insert the lens 16 by using two hands to hold the eyelid open not only with just one hand, while having a clear view down to the mirror revealing the desired axis to be obtained without any significant visual blockage.

The lens cup podium 82 of the LNSAID™ System 80 preferably is of a transparent material to allow the user to look directly through the platform 88 and using both of their eyes and especially the non-insertion eye, navigate properly to the best alignment and place their eye on the lens 16 being held by the lens cup 10. The soft, supple material of the lens cup 10 compresses and the lens 16 instantly and smoothly adjusts to make the exact position be in proper axis within the eye. Using two hands to hold the eyelids open and focusing only on maneuvering the head downwards using the neck muscles to align the eye on the lens 16 with the help of a mirror 114 greatly reduces any opportunity to be in the wrong position or bump or drop the lens 16. The lens cup 10 provides an overhang O to make grasping the lens 16 with the eyelids easy and in some embodiments, smooth ridges 18 to prevent any possibility of slight suction and allowing the lens 16 to more easily be pulled away from the lens cup 10 and be captured. The LNSAID™ System 80 makes it much easier and more comfortable to insert the lens 16 within the eye in a much different manner than the procedures of the prior art. This prior art requires methods such as using only the fingertip or fingertips of one hand to try to accurately maneuver a lens 16 without tipping or bumping the lens 16 against the eye, face or another object and thereby dropping the lens 16. A good view to a mirror is also obstructed b fingers. Methods for insertion of the prior art also commonly require holding the eyelids with only one hand and trying to prevent blinking or flinching of the eyelids as the lens 16 is drawn close to the eye, and then holding the lens 16 within the eye long enough to align the lens 16 in a proper position to then release the eyelids and capture the lens 16 without having a single eyelash be caught behind the lens 16. Any misalignment or eyelash behind the lens requires repeating the process of insertion, perhaps several times.

The LNSAID™ System 80 of the present invention provides very important advantages over the prior art including a distinctive lens cup 10 that prevents misalignment or possible damage to the eye by providing for critical minor final adjustment of the lens axis within the eye. The LNSAID™ System 80 further provides, a degree of softness that significantly reduces injury and the most critical feature, that of a clear view down the support tube 84 to a mirror 114 for revealing the desired axis to the fullest view, a twice as long view down the length of the support tube 84, without obstruction by a wide support base allowing for use of both hands to more fully open the eyelids at the moment of lens insertion. The soft pliable lens cup 10 may also provide smooth ridges that substantially eliminates the possibility of any suction that might occur. The smooth ridges do not have creases or crevices that would be difficult to clean and are formed along the outer edge of the lens cup 10 where the lens 16 is supported. The soft supple antibacterial, medical grade material of the lens cup 10 also provides a higher amount of safety to the eye of the user and a personal precision fit of the lens 16 unlike lens insertion tools of the prior art especially for scleral lens with their larger diameters. Note that if the lens 16 is dropped, it will not be sent off angularly, it will drop on the mirror 114 and not be so easily lost, much differently than a wide rounded support base of the prior art that will likely project a dropping lens laterally, away and possibly onto the floor. The LNSAID™ System 80 further removes the added patience and dexterity required to insert the lens 16 by use of procedures of the prior art, especially for the disabled or older people. Thus, the LNSAID™ System 80 will further make a user more comfortable in inserting a larger scleral lens 16 repeatedly which may be very advantageous to have a user become more accustomed to continue and keep using their scleral lens that may provide added benefits in improving their vision. The LNSAID™ System 80 further provides the added advantages of a complete system or kit that has everything a user may need to clean, add saline, insert and remove a lens.

To further assist in making the insertion of a scleral lens more manageable other embodiments of the LNSAID™ System provide an extended tapered applicator 170 that may be held and be more easily maneuvered by a user to insert the lens 16 in the eye. As shown in FIG. 28A, an embodiment of the lens cup tapered applicator 170 comprises an upper lens cup portion 172, an indented, curved mid-section 174, and a tapered conical base 176. The upper lens cup portion 172 has an interior surface 178 that may be of any depth to accommodate lenses 16 of various shapes, sizes and dimensions, and even non-symmetrical shapes. In order to support a lens 16 along the rim 180 of the lens cup applicator 170, the lens cup portion 172 is uniquely formed to accommodate a shallower or deeper depth to encompass the curvature of a lens 16 and particularly of scleral lenses that have larger diameters and wider ranges of curvature. As shown in cross-section in FIG. 28B, the curvature of the interior side surface 181 is uniquely formed as a parabolic curve that extends increasingly out and upwards from a stiffer interior central portion 183 that may have a thin membrane, small hole or larger hole to a more flexible outer rim 180. By forming the curvature of the lens cup portion 172 as a parabolic curve that consists of a single bend and two lines going off to an infinite distance, the interior surfaces 181 of the lens cup are not in parallel and therefore forces as the eye presses against the lens 16, deflect the rim 180 outward allowing for greater compression and the proper adjustment of the axis of the lens 16. The outer rim 180 is more easily flexed in a way that is very different from cup or bowl shaped lens cups of the prior art. The base of the parabolic curve within the center portion 183 is more rigid and has greater stiffness providing stable support to hold the lens 16 in the lens cup 172.

In embodiments of the lens cup, the rim 180 may be rounded from the interior side surface 181 to an outer edge 182 which is the mating joint in a mold, thereby providing for the lens 16 to be supported on the rounded surface of the rim 180 and not on the edge 182. The edge 182 is a flash point where inner and outer molds have been separated during the molding process. Commonly in lens cups of the prior art, the flash point is the resting point and may be formed with imperfections or crevices, bumps or indents, where dirt and germs can collect. The rounded rim 180 and outer flash point at the edge 182 moves this possible source of dirt and germs away from the lens and eye. As shown in FIG. 28C, along the rim 180, the lens cup portion 172 may have just one smooth continuous surface all around, or include smooth radial ripples or ridges 184 that can substantially reduce suction between the lens 16 and lens cup 172 that may occur at the moment when the eyelids grasp the scleral lens. These ridges 184 are formed without creases or crevices and are smooth in all transitions preventing dirt or germs from being trapped for easier cleaning.

The outer walls 186 of the lens cup portion 172 are formed as a parabolic shaped partial hemisphere and at a different curvature than the curvature of the interior parabolic curved surfaces 181 to accommodate the desired greater stiffness toward the foundation at the central portion 183 of the lens cup 172. The difference in curvature between the interior surface 181 and exterior walls 186 creates a thickened portion along the central portion 183 where there may be a hole or thin membrane to allow light. From the central portion 183, the walls 186 become progressively thinner as they extend to the rim 180 in an appropriate way to accommodate proper increasing flexion induced by pressure from the eye's instant contact with the scleral lens which is usually at one part of the lens first, then progresses till full surround contact of the lens is made within the eye. These outer walls 186 smoothly transition parabolically to the mid-section 174 that extends as a smooth parabolic curvature 188 inward and then outward forming a gripping portion where a user may securely hold the lens cup applicator 170 to add saline solution and place and remove the lens 16 within the upper portion lens cup 172. The user may then if they prefer, maneuver the applicator 170 to their eye to insert the lens 16. In some embodiments, as shown in a cross-sectional view of the lens cup applicator 170 in FIG. 28B, angled interior walls 190 accommodate the focused direction of light or just ambient light and light from a powered light source up and through a hole 192 in the lens cup 172 to indicate the center of the lens cup 172 and lens 16 and provide for a user to more easily center their eye over the illuminated central point. In embodiments of the lens cup applicator 170, a hole 192 that is of a very small diameter is provided for light to be in a direct line as it shines through the hole 192 pinpointing the location of the center of the lens cup 172. The hole 192 is formed through the central portion 183 and may be of any desired diameter. By angling the interior walls 190 inward from the bottom 194 of the base 176 up through the mid-section 174 to the central portion 183, a ledge portion 196 can be formed. A top view of the lens cup applicator 170 and central portion 183 is shown in FIG. 28D and a bottom view of the lens cup applicator 170 and ledge 196 is shown in FIG. 28E.

Figure 29:
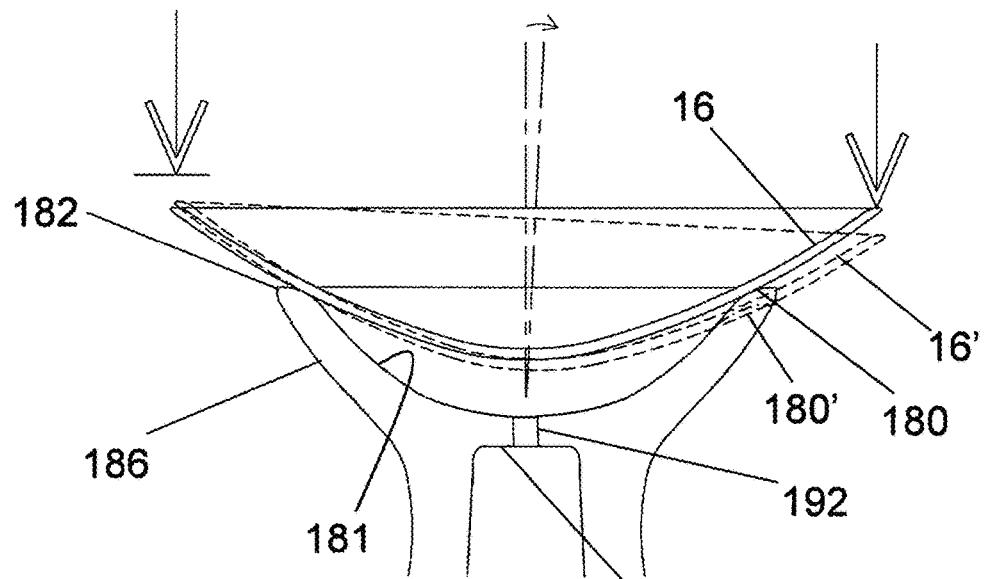
FIG. 29 is a cross-sectional view of an embodiment of a lens cup in an embodiment of the present invention.

An important feature of the lens cup 172 is how it accommodates the reality of scleral lens insertion by being more flexible at its outer rim 180. The thickness of the central portion 183 provides rigidity and stiffness at the foundation of the upper portion lens cup 172. The parabolic curve of the interior surface 181 and the differently shaped parabolic curve of the outer walls 186 allows transition in stiffness from the foundation along the central portion 183 to the rim 180 as the outer walls 186 become thinner and lose some of their inherent stiffness. By providing a stiff foundation a lens 16 will be well supported on the lens cup 172 and by reducing the stiffness progressively along the walls 186, rim 180 and outer edge 182, the lens cup 172 will be flexible at the critical point as the eye is pressed against the lens 16, on the rim 180 which will immediately allow it to conform, to allow for a small but critical movement of the lens 16 to perfectly align for example a scleral lens within the eye. The parabolic curved shaped interior surfaces 181 also become more flexible as this final force is continually applied from the eye pressing against the lens 16 to make complete contact and full surround contact to the sclera of the eye when using a scleral lens. This is the moment between success and failure, as most failures will likely occur by not making this full surround contact. As shown by the large arrows in FIG. 29, the interior surface 181 and rim 180 are spread outward more easily providing more flexibility than a force applied along an edge of a lens cup having less designed in progressive flexibility in its structure. In the bowl shaped designs of the prior art, a vertical force is applied against a circular vertical wall compressing the wall to a point of possible non-uniform deformation that would not easily and readily flex properly outward, as compared to the flexing parabolic shaped curve surfaces 181 of the lens cup 172. This outward flexing provides for the lens 16' shown in dotted lines to make a slight but critically important adjustment to rotate the lens 16 on its axis along the flexible rim 180 under the slightest eye pressure. The flexing of the rim 180 quickly accommodates for the slightest pressure brought down by the eye that initially contacts the saline and while squeezing out most of saline contacts a single point on the lens 16. As the eye is brought down further the rim 180 flexes outward rotating the lens 16 on its axis. Because of the specific flexibility of the rim 180 of the lens cup 172, continued descent is allowed and the lens 16 fully surrounds and rapidly makes contact with the sclera and is properly positioned within the eye. As shown in dotted lines the position of the lens 16 is properly and immediately adjusted within the eye. The small arrow and dashed lines of the moving lens 16' shows the rotation of flex as the lens 16 is correctly positioned in the eye. Lens cups of the prior art are also commonly of a single hard rigid material and thickness and fail to provide any or enough flexibility for the desired near instantaneous adjustment that is needed to properly position the lens 16 within the eye. Various embodiments of differently configured parabolic curvature of the interior surfaces 181 and outer walls 186 are within the scope of the present invention to provide the needed transition in stiffness from a rigid base at the central portion to the enhanced flexibility along the rim. This critical progressive more flexible feature in the lens cup 172 is intended to be covered within these embodiments. Importantly, failure of successful insertion is often related to not making a successful insertion simply by not having the capability to rotate the axis of the lens 16 within the lens cup enough to make the full surround contact of the lens and eye complete. The parabolic curvature feature and the clear view without obstruction to the podium tube in a mirror are important aspects that lead to success in the insertion process and are critical to include in the proper instruction in the use of the LNSAID System to accomplish this.

Figure 30:
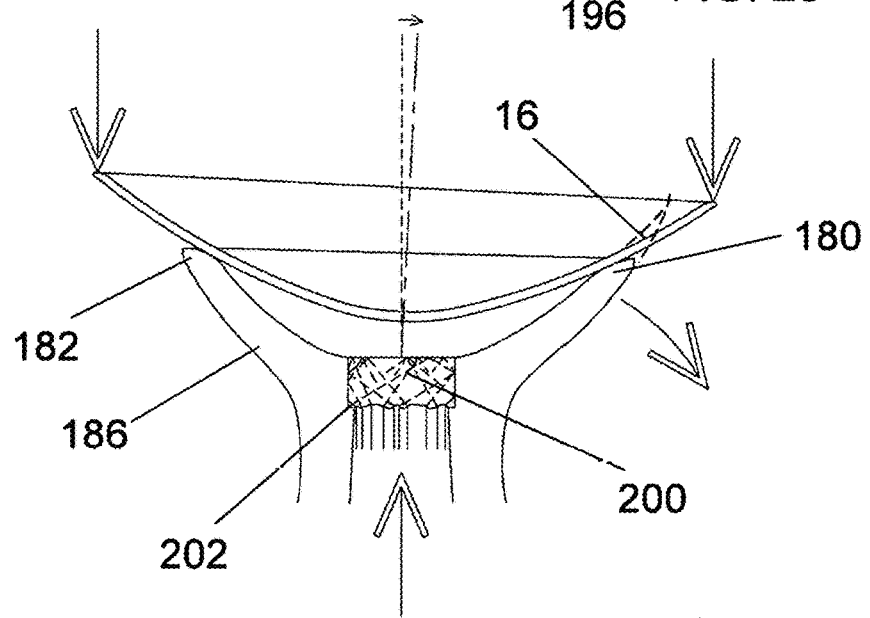
FIG. 30 is a cross-sectional view of a further embodiment of a lens cup in an embodiment of the present invention.

As shown in FIG. 30, in some embodiments the ledge 196 may have a glass or plastic light filter 200 that is supported on a shelf 202 that is formed as the hole 192 at the top of the angled interior walls 190. The rigid light filter 200 is configured to scatter light geometrically at its base, to cause the lens to glow with light via random or designed pattern configurations at the bottom only. The light filter 200 also helps to provides stiffness at the foundation of the lens cup 172. The rim 180 and parabolic curvature of the surfaces 181 and outer walls 186 provide the unique enhanced edge flexibility feature that assists in properly adjusting the exact position of the lens 16 in the eye quickly. As shown in FIG. 31, the light filter 200 may be inserted from the top of the lens cup applicator 170 to be positioned on the shelf 202 and be secured using a waterproof non-toxic humanly safe adhesive to prevent the filter 200 from falling out. The light filter 200 may be formed at its bottom only with irregular surfaces, a pyramid shaped surface or random markings at its bottom to scatter light such as by configuration or etching to cause light shown scattering in angular lines in the inset FIG. 31A to be scattered in multiple directions intentionally, shown as dashed lines through the filter 20 to soften and reduce spot brightness of a concentrated light beam and to just glow in the target area for a more comfortable insertion process. In some embodiments, the filter 200 may be colored to further diffuse and reduce a bright white light to a glow even though it is aligned directly with the eye as the lens 16 is inserted. The filter 200 may be of any width and diameter and be chosen based on the size and amount of softening of the light and the color desired. Particularly, for a user with one eye, a medical condition or poor vision in one or both eyes, the filter 200 of a sufficient diameter may be preferred to the small opening 192 to provide a softer glow of light and a large enough target that can be seen to indicate the center of the upper lens cup portion 172 of the lens cup applicator 170. A top view of the lens cup applicator 170 with filter 200 is shown in FIG. 31B and a cross-sectional view with the filter 200 installed and anchored on the shelf 202 formed at the top of the angled interior walls 190 is shown in FIG. 31C. A bottom view of the lens cup applicator is shown in FIG. 31D and a perspective view is shown in FIG. 31E with light scattering in multiple directions is shown to soften the brightness, or make it glow, while still providing a clear indication of the central portion of the lens cup 172 to facilitate easy positioning of the eye to capture the scleral lens 16.

As shown in FIG. 31E, the exterior walls 198 of the conical base 176 are angled outward from the bottom 194 up and to the mid-portion curvature 188 that then smoothly curves inward, providing an easy comfortable grasping area and then outward to the outer walls 186 of the upper portion lens cup 172. The outward taper and conical slope of the exterior walls 198 provides for the lens cup applicator 170 to be accurately positioned and held firmly into the podium support tube 84 by gravity and/or by configuration of a snap-fit, frictional-fit or use of compatible adhesive. As shown in FIG. 32A, the conical slope of the exterior walls 198 provide for embodiments of the lens cup applicator 170 to mate and be aligned within a further embodiment of the support tube 84 having a taper 204. The taper 204 has been formed starting from the top 206 of the support tube 84 and extending at the same angle as the tapered exterior walls 198 of the conical base 176. The lens cup applicator 170 may be inserted using only a minimal amount of force and/or be dropped-in or slid into and be secure in the support podium tube 84 with its matching conical shape, as shown in FIG. 32B. The tapered exterior walls 198 also evenly center the lens cup applicator 170 to hold the upper lens cup portion 172 in a stable horizontal position to help keep the lens 16 from falling out of the lens cup 172. While the exterior walls 208 may be vertical, the interior and exterior walls 210 of the support tube 84 may be highly polished to further enhance directing light up and through the support tube 84 and through the small opening 192 or the filter 200 in the lens cup applicator 170. Alternatively, the fingers can also hold the conical base 176 for hand-held insertion.

As shown in FIG. 33, in an embodiment of the LNSAID™ Kit System 80 of the present invention, a kit may be provided comprising the lens aid applicator 170, a lens cup podium 82 having a podium support tube 84 and a storage tube 86 extending vertically from a platform 88. Additionally, the LNSAID™ Kit may also include a mirror 114 and the mirror may also include a built-in light source 214. The light source 214 comprises a housing 216, a power switch 218, a power source 220 such as replaceable batteries, a wire connection 222 from the power switch 218 to a lamp 224. The powered light source 214 is preferably small and compact to be contained, enclosed, affixed or positioned near the bottom portion of the mirrors glass top surface 240 that serves as the front facing waterproof surface of the mirror 240 because saline will be intentionally spilled on it at every scleral lens insertion. The power switch 218 may be accessible near or within a handle 228 of the mirror 114 to turn the light on and off as needed by push button preferably. The handle 228 may have a mounting bracket 230 to attach the handle 228 to the mirror 114. No holes are drilled through the glass; rather, the mirror surface on the bottom of the glass is cleaned of its reflective material thus keeping the top surface waterproof to the electrical equipment below. Saline will always spill onto the mirror surface with each insertion as it is displaced in the lens cup with the eye replacing it and squeezing out most of the saline as a natural process of lens insertion, but not all saline is spilled, as some is wanted to stay naturally between the eye and scleral lens. This is at the heart of the scleral lens beneficial quality, having the ability to correct one's vision using saline optically between the damage of the eye and the scleral lens, making the damage disappear optically. The saline is mounded up in the scleral lens to also ensure that no bubbles will be captured between the eye and scleral lens when the insertion is performed correctly. The mirror 114 can direct a power light source straight up through the mirror and glass 114, and continues up through the support tube 84, and through the lens cup applicator 170 to assist in aligning the eye with the center of the lens cup 172 and lens 16. The light source point 232 is preferably at a position offset from the center of the mirror 114 to place the eye so that the lens 16 will be inserted closer to one edge of the mirror 114 allowing the arranging of the position of the mirror 114 to provide for a greater area for viewing through to the reflection of the user's insertion eye while looking along the podium support tube 84 using one's other eye. For the insertion of a lens 16 in the left eye, the mirror 114 is positioned on a table with the light source point 232 offset from the center of the mirror 114 to the left and for the insertion of a lens into the left eye. For insertion of the lens 16 in the right eye, the mirror 114 is rotated to the right on a table with the light source point 232 offset from the center of the mirror 114 to the right.

As shown in FIG. 34 the powered light source 214 is affixed to the underside of the mirror 114 and is enclosed with a protective cover with the light source on/off switch housing 216 extending partially out from the edge of the mirror frame 226 to provide access for power switch 218 to connect to the wiring, removable batteries and a light source, all below the mirror glass surface. The power switch 218 may have a push button 234 or other controller connected by a shaft 236 to the power switch 218 to the power source 220 and lamp 224. The power source 220 may be two CR 2032 Lithium batteries that lay flat within the housing 216 making them replaceable. The mirror rim 238 that surrounds the mirror frame 226 is watertight, and holds the mirror glass 240 rigidly sealed in place. The mirror frame 226 may fully cover all or a portion of the rear of the mirror glass 240 and with the light source housing 216 support the mirror 114 and keep the mirror 114 level on a flat surface to keep the lens cup podium stable 82 on the surface of the mirror 114 above any spilled liquid. The wire 222 extends from the switch 218 and housing 216 to the power source and lamp 224 below and may be shielded within the housing 216 and frame 226 preventing an electrical connection from being exposed to any moisture. The lamp 224 is positioned below the mirror 114 directly under the light source point 232. The lamp 224 is preferably a small light emitting diode (LED) that may be chosen to have the proper color and brightness to provide enough light to shine up through the mirror 114, the support tube 84 as indicated with arrows and the lens cup applicator 170. As shown in the inset in FIG. 34A, the support tube 84 may be formed of clear flat or even concave plastic or preferably with a convex lens 242 at its base 244 to help focus ambient light or the light being emitted from the lamp 224 to prevent scatter and purposely focus light to the opening 192 in the lens cup or filter 200 within the lens cup applicator 170.

Figure 37:
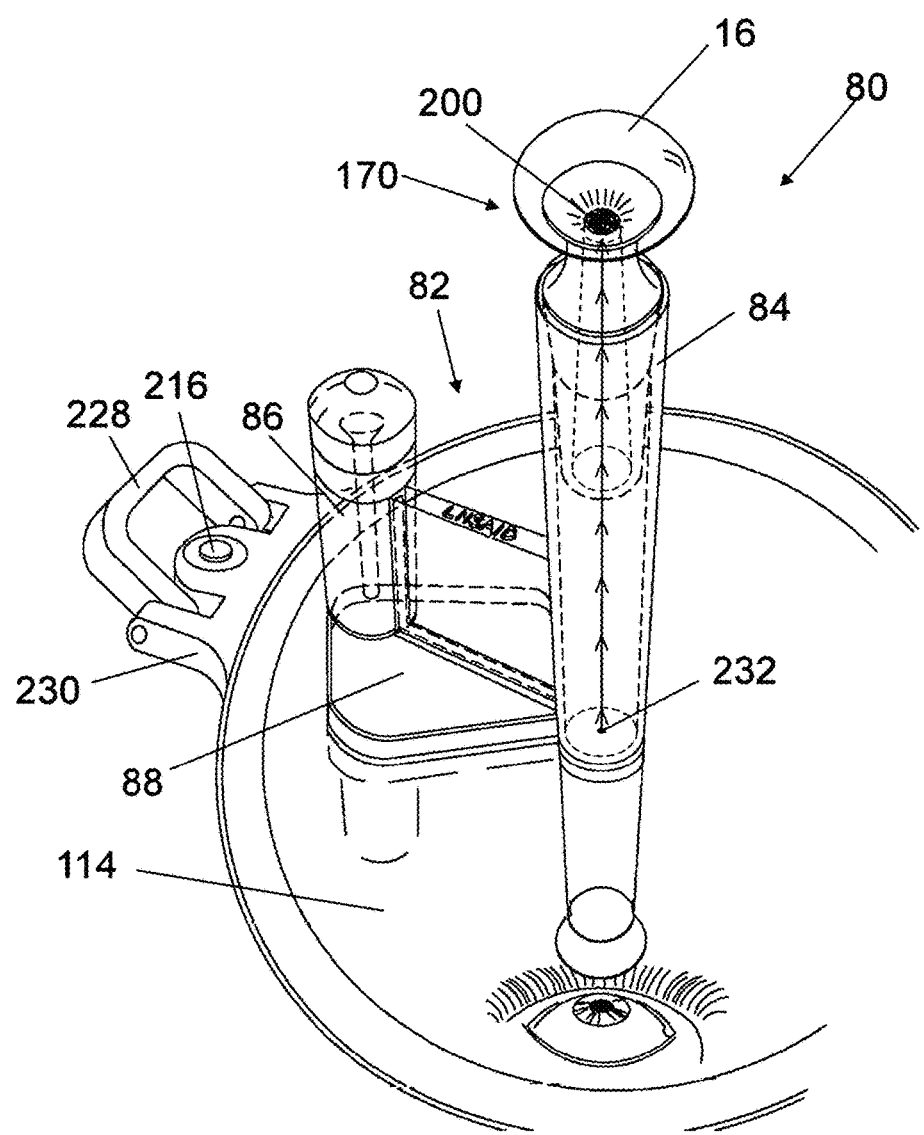
FIG. 37 is a perspective view of an embodiment of the LNSAID System of the present invention with a mirror and powered light source.

As shown in FIG. 35, the lens cup podium 82 may be aligned on the mirrored surface at the light source point 232 at any angle with respect to the handle 228 to accommodate the most comfortable position for a user to insert the lens 16. In other embodiments, as shown in FIG. 36 and in the inset in FIG. 36A, the base 244 may be formed with a convex lens on the top and bottom of the clear base of the podium tube 84 that directs light by focusing light to a focal point through the center of the lens cup applicator 170 above. In another embodiment as shown in FIG. 36B, the base 244 may be provided with a convex lens 246 just on top to direct and focus ambient light or light from the light source 214 to the support tube 84 and have the light be redirected through the center of the lens cup applicator 170. As shown in FIG. 37, light shown as a series of arrows is focused directly up and through the light source point 232 in the surface of the mirror 114, through the support tube 84 to assist a user in aligning their eye directly over the center of the lens 16 and lens cup 172 for a more reliable lens insertion into the eye, especially important if the patient has only one eye. In some embodiments, a towel (not shown) with stitched built-in turned up edges may simply be under or be removably affixed to the edges of the mirror 114 to extend out and around the mirror 114 to help capture a falling scleral lens more safely.

An important additional feature of the lens cup applicator 170 is the capability to be used as just a hand applicator, to perform a hand-held insertion of the lens 16. A hands-free insertion of the lens 16 is critically based on the preferences of the user. In a further embodiment, as a hand applicator, the lens cup applicator 170 has a distinct advantage over applicators of the prior art by aiding in the insertion of a scleral lens 16 into the eye by finger activated physical raising of the lens 16 off of the upper portion lens cup 172 at the appropriate time during insertion. As shown in FIG. 38A, by having a thin flexible membrane 201 and by having separate locations 1 and 2 along the applicator 170, a user may first cover the bottom 194 then squeeze or place a finger over the hole of the base 194 to close it. Then at 179 below location 1, quickly squeeze along this mid-section 179 to pressurize the air trapped inside and subsequently force the membrane 201 to move up pushing the lens 16 up into the eye for insertion aid, where the eyelids are then released to capture the lens. The membrane 201 is shown in a raised position in FIG. 38B. The pressure may also be decreased to draw the membrane 201 down and into the lens cup applicator 170 to create suction in the air in the lens cup 172 and draw the lens 16 towards the lens cup 172 to aid in lens removal. As shown in FIG. 38C, to decrease pressure the user slowly squeezes at location 1 first to force air out, then seal the bottom opening with a fingertip at location 2 and then release the pressure quickly at location 1 of the lens cup applicator 170 to create a bit of suction to pull the membrane down 201 grabbing and pulling the lens at the same time and bring it into the lens cup applicator 170 as shown in FIG. 38D.

As shown in FIG. 38A, the further embodiment of the lens applicator 170 is formed with an upper portion lens cup 172, a curved walled mid-section 174, and a base 176 that is divided into an angled section 177 having conically angled exterior walls 198 and a cylindrical section 179 that can have a step portion 181 that provides for the lens cup applicator 170 to be seated along a ledge 207 provided within a further embodiment of the support tube 84. As shown in FIG. 39A, the ledge 207 is at a depth from the top 206 of the support tube 84 to provide for an edge 183 formed at the bottom of the mid-section 174 to sit and be supported on the top 206 of the support tube 84. The support tube 84 is provided with straight vertical walls 205 along this portion to provide a frictional fit along the straight exterior wall surfaces of the cylindrical section 179 of the base 176. With this further embodiment, the lens cup applicator 170 may be slid into the support tube 84 and be securely seated against the ledge 207 to provide stable and level alignment of the lens cup 172. The upper portion lens cup 172 has a similar rigid foundation around the membrane 201 which can be so thin in cross section as to allow light to cause it to glow as a center position indicator to the patient. The unique flexibility feature of the present invention can assist in centering by glowing with a light source and in properly helping the adjustment of the eye position over the lens 16 to be inserted in the eye.

Although specific embodiments of the invention have been disclosed herein in detail, it is to be understood that this is for purposes of illustration. This disclosure is not to be construed as limiting the scope of the invention, since the described embodiments may be changed in details as will become apparent to those skilled in the art in order to adapt the design of the LNSAID™ System 80 of the present invention to particular applications, without departing from the scope of the present invention and the following claims and equivalents of the claimed elements.

What is claimed is:

1. A lens insertion aid, comprising:
a lens cup of a pliable material having a parabolic curvature configured to flex to adjust the axis of the lens at the immediate point of contact of a lens with the eye to correctly align the position of the lens within the eye as the eye is brought against the lens and is captured by the eyelids;
the lens cup comprising:
an opening through a central portion at a base of the parabolic curvature;
a filter sealing the opening in the central portion, the filter having etching configured to scatter light and glow from ambient light or from light from a powered light source.

2. The lens insertion aid of claim 1 wherein the pliable material of the lens cup is from a group consisting of antibacterial, antimicrobial, soft, pliable type plastic, polymer, silicone, and other medical grade material, with soft durometer qualities.

3. The lens insertion aid of claim 1 comprising greater stiffness at the base of the parabolic curvature that transitions to greater flexibility at the top of the parabolic curvature to rapidly flex to rotate the lens on its axis to have the lens make complete contact and full surround contact to the sclera of the eye when using a scleral lens.

4. The lens insertion aid of claim 3 wherein the lens cup comprising:
a rim at the top of the parabolic curvature configured to flex; and
the central portion at the base of the parabolic curvature configured to be rigid.

5. The lens insertion aid of claim 4 wherein the lens cup comprising:
interior surfaces of one parabolic curvature; and
exterior walls of a different parabolic curvature, the exterior walls configured to decrease in stiffness and increase in flexibility from the central portion to the rim of the lens cup.

6. The lens insertion aid of claim 1 wherein the opening through the central portion of the lens cup having tapered walls.

7. The lens insertion aid of claim 1 wherein a membrane seals the opening in the central portion, the membrane configured to flex up or down and glow from ambient light or from light from a powered light source.

8. The lens insertion aid of claim 1 wherein the rim of the lens cup comprising smooth rounded ridges that do not have crevices or creases.

9. The lens insertion aid of claim 1 wherein the lens cup is disposable.

10. The lens insertion aid of claim 1 wherein the lens cup comprising an upper portion having the parabolic curvature and the base, the upper portion configured to have a diameter that is less than the diameter of a lens to provide an overhang to assist the eyelids in more easily capturing the lens.

11. The lens insertion aid of claim 10 wherein the base having a diameter that is smaller than the diameter of a support tube, the base configured for attachment to a support tube for hands-free insertion of a lens.

12. The lens insertion aid of claim 11 wherein the base of the lens cup comprising a conical slope and the support tube comprising a conical taper formed at the top of the support tube.

13. A lens insertion system, comprising:
a support tube of a transparent material and having a convex lens in its base to focus light through the support tube to a lens cup;
a lens cup removably attached to the support tube;
a platform; and
the lens insertion system configured for hands-free insertion of a lens within the eye allowing for the eyelids to be opened using one or both hands for easier insertion of the lens;
a mirror;
a powered light source enclosed within the mirror with light from the light source passing through the glass of the mirror through a hole in the reflective material of the mirror.

14. The lens insertion system of claim 13 wherein a corner of the platform extends at an angle that is 90 degrees or less and the support tube is attached to the corner of the platform providing for a user to place the platform on a mirror and have a double length clear view down and around a large portion of the vertical axis of the support tube using one or both eyes to properly align the eye over the lens.

15. The lens insertion system of claim 13 wherein the platform having a circular shape that extends around the support tube providing a viewing area of up to 358 degrees for a user to place the lens insertion system on a mirror and have a double length clear view down into a mirror of the vertical axis of the support tube using one or both eyes to properly align the eye over the lens.

16. The lens insertion system of claim 13, comprising:
a storage tube.

17. The lens insertion system of claim 13, comprising:
one of at least a lens removal tool, saline solution, and protein cleanser.

18. The lens insertion system of claim 13, comprising:
a stabilizer brace.

* * * * *